US006475744B1

(12) United States Patent
Reppert et al.

(10) Patent No.: US 6,475,744 B1
(45) Date of Patent: Nov. 5, 2002

(54) METHODS FOR IDENTIFYING COMPOUNDS WHICH MODULATE CIRCADIAN RHYTHM

(75) Inventors: Steven M. Reppert, Newton, MA (US); David R. Weaver, Londonderry, NH (US); Mark Zylka, Pasadena, CA (US); Xiaowei Jin, Boston, MA (US); Kazuhiko Kume, Belmont, MA (US); Sriram Sathyanarayanan, Somerville, MA (US); Lauren Shearman, Jamaica Plain, MA (US)

(73) Assignee: The General Hospital Corporation, Boston, MA (US)

( * ) Notice: Subject to any disclaimer, the term of this patent is extended or adjusted under 35 U.S.C. 154(b) by 23 days.

(21) Appl. No.: 09/618,425

(22) Filed: Jul. 18, 2000

Related U.S. Application Data

(60) Provisional application No. 60/203,005, filed on May 10, 2000, and provisional application No. 60/145,363, filed on Jul. 22, 1999.

(51) Int. Cl.$^7$ .............................................. G01N 33/53
(52) U.S. Cl. ....................................................... 435/7.1
(58) Field of Search ......................................... 435/7.1

(56) References Cited

U.S. PATENT DOCUMENTS

| | | |
|---|---|---|
| 5,194,614 A | 3/1993 | Andrieux et al. |
| 5,240,919 A | 8/1993 | Yous et al. |
| 5,276,051 A | 1/1994 | Lesieur et al. |
| 5,328,470 A | 7/1994 | Nabel et al. |
| 5,464,872 A | 11/1995 | Langlois et al. |

FOREIGN PATENT DOCUMENTS

| | | |
|---|---|---|
| WO | WO 88/06630 | 9/1988 |
| WO | WO 95/35320 | 12/1995 |

OTHER PUBLICATIONS

Albarracin et al., "Isolation and Characterrization of the 5'–Flanking Region of the Mouse Gonadotropin–Releasing Hormone Recpetor Gene," *Endocrinology* 135:2300–2306, 1994.

Albrecht et al., "A Differential Respsonse of Two Putative Mammalian Circadian Regulators, mper1 and mper2, to Light," *Cell*, 91:1055–1064, 1997.

Allada et al., "A Mutant Drosophila Homolog of Mammalian Clock Disrupts Circadian Rhythms and Transcription of period and timeless," *Cell*, 93:791–804, 1998.

Altschul et al., "Basic Local Alignment Search Tool," *J. Mol. Biol.*, 215:403–410, 1990.

Altschul et al., "Gapped Blast and Psi–Blast: a new generation of protein database search programs," *Nucleic Acids Research*, 25:3389–3402, 1997.

Bagnara et al., "Endocrinology of the Amphibian Pineal," *Am. Zoologist*, 10:201–216, 1970.

Balsalobre et al., "A Serum Shock Induces Circadian Gene Expression in Mammalian Tissue Culture Cells," *Cell*, 93:929–937, 1998.

Bartness et al., "Mammalian pineal melatonin: A clock for all seasons," *Experientia*, 45:939–945, 1989.

Bittman et al., "The Distribution of Melatonin Binding Sites in Neuroendocrine Tissues of the Ewe," *Biology of Reproduction*, (1990) 43:986–993.

Carlson et al., "Melation Signal Transduction in Hamster Brain: Inhibition of Adenylyl Cyclase by a Pertussis Toxin–Sensitive G Protein," *Endocrinology*, 125:2670–2676, 1989.

Ceriani et al., "Light–Dependent Sequestration of Timeless by Cryptochrome," *Science*, 285:553–556, 1999.

Cole et al., "The EVB–Hybridoma Technique And Its Application To Human Lung Cancer," *Monoclonal Antibodies and Cancer Therapy*, 77–96, 1985.

Chomeczbski et al., "Single–Step Method of RNA Isolation by Acid Guandinium Thiocyanate–Phenol–Chloroform Extraction," *Anal. Biochem*, 162:156–159, 1987.

Cullen et al., "Use of Eukaryotic Expression Technology in the Functional Analysis of Cloned Genes," *Methods Enzymol.*, 152:684–704, 1987.

Darlington et al., "Closing the Circadian Loop: Clock–Induced Transcription of Its Own Inhibitors per and tim," *Science*, 280:1599–1603, 1998.

de Wet et al., "Firefly Luciferase Gene: Structure and Expression in Mammalian Cells," *Mol. Cell. Biol.*, 7:725–737, 1987.

Dubocovich et al., "Use of 2–[$^{125}$I] iodomelatonin to characterizs melatonin binding sites in chicken retina, " *Proc. Natl. Acad. Sci. USA*, 84:3916–3920, 1987.

Duarnit et al., "2–Bromomelatonin: Synthesis and Characterization of a Potent Melatonin Agonist," *Life Sci.*, 51:479–485, 1992.

Ebisawa et al., "Expression Cloning of a High–Affinity Melatonin Receptor From Xenopus Dermal Melanophores," *Proc. Natl. Acad. Sci. USA*, 9:6133–6137, 1994.

Field et al., "Analysis of Clock Proteins in Mouse SCN Demonstrates Phylogenetic Divergence of the Circadian Clockwork and Resetting Mechanisms," *Neuron*, 25:436–447, 2000.

Friedman et al., "Cellular Promotors Incorporated into the Adenovirus Genome: Cell Specificity of Albumin and Immunoglobulin Expression,"*Mol. and Cell Bio.* 6:3791–3797, 1986.

(List continued on next page.)

Primary Examiner—Karen Cochrane Carlson
(74) *Attorney, Agent, or Firm*—Fish & Richardson P.C.

(57) ABSTRACT

The invention is based, in part, on the discovery that the CRY proteins and the PER2 protein function as important modulators of mammalian circadian rhythm. The invention includes methods of modulating the circadian rhythm and identifying compounds that modulate the circadian rhythm.

33 Claims, 15 Drawing Sheets

OTHER PUBLICATIONS

Gekakis et al., "Isolation of timeless by PER protein interaction: Defective Interaction Between timeless Protein and Long–Period Mutant PER$^L$," *Science*, 270:811–815, 1995.
Gekakis et al., "Role of the Clock Protein in the Mammalian Circadian Mechanism," *Science*, 280:1564–1569, 1998.
GenBank Accession No. AB000777, Kobayashi et al., "Characterization of photolyase/blue–light receptor homologs in mouse and human cells," Nov. 21, 1998.
GenBank Accession No. AB003433, Kobayashi et al., "Characterization of photolyase/blue–light receptor homologs in mouse and human cells," Nov. 21, 1998.
GenBank Accession No. AB105203, Ikeda, "Direct Submission," Oct. 21, 1999.
GenBank Accession No. AF156987, Kume et al., "Direct Submission," Aug. 2, 1999.
GenBank Accession No. AF050182, Zylka et al., "Direct Submission," Jun. 27, 1998.
GenBank Accession No. AF071506, Zylka et al., "Direct Submission," Nov. 28, 1998.
GenBank Accession No. AF000998, King et al., "Positional cloning of the mouse circadian clock gene," 1997.
Glossop et al., "Interlocked Feedback Loops Within the Drosophila Circadian Oscillator," *Science*, 286:766–768, 1999.
Gordon, "Transgenic Animals," *International Review of Cytology*, 115:171–229, 1989.
Griffin et al., "Light–Independent Role of CRY1 and CRY2 in the Mammalian Circadian Clock, " *Sicence*, 286:768–771, 1999.
Hahn et al., "Yeast TATA–binding protein TFIID binds to TATA elements with both consensus and non–consensus DNA sequences," *Proc. Natl. Acad. Sci. USA*, 86:5718–5722, 1989.
Hammang et al., "Immortalized Retinal Neurons Derived from SV40 T–Antigen–Induced Tumors in Transgenic Mice," *Neuron*, 4:775–782, 1990.
Hao et al., "A Circadian Enhancer Mediates PER–Dependent mRNA Cycling in *Drosophila melanogaster,*" *Mol. and Cell Bio.*, 17:3687–3693, 1997.
Heckert et al., "Structural Organization of the Follicle–Stimulating Hormone Receptor Gene," *Mol. Endocrinology*, 6:70–80, 1992.
Hogenesch et al., "The basic–helix–loop–helix–PAS orphan MOP3 forms transcriptionally active complexes with circadian and hypoxia factors," *Proc. Natl. Acad. Sci. USA*, 95:5474–5479, 1998.
Honma et al., "Cicadian Oscillation of BMAL1, a Partner of a Mammalian Clock Gene Clock, in Rat Suprachiasmatic Nucleus," *Biochem. and Biophys. Res. Comm.*, 250:83–87, 1998.
Ikeda et al., "cDNA Cloning and Tissue–Specific Expression of a Novel Basic Helix–Loop–Helix/PAS Protein (BMAL1) and Identification of Alternatively Spliced Variants with Alternative Translation Initiation Site Usage," *Biochem. and Biophys. Res. Comm.*, 233:258–264, 1997.
Ikuyama et al., "Characterization of the 5'–Flanking Region of the Rat Thyrotropin Receptor Gene," *Mol. Endocrinology*, 6:793–804, 1992.
Ishiura et al., "Expression of Gene Cluster kaiABC as a Circadian Feedback Process in Cyanobacteria," *Science*, 281:1519–1523, 1998.
Jackson et al., "Do the Poly(A) Tail and 3' Untranslated Region Control mRNA Translation?," *Cell*, 62:15–24, 1990.

Jin et al., "Molecular Mechanism Regulating Rhythmic Output from the Suprachiasmatic Circadian Clock," *Cell*, 96:57–68, 1999.
Karne et al., "Cloning and Characterization of an Endothelin–3 Specific Receptor (ETcReceptor) from *Xenopus laevis* Dermal Melanophores," *J. Biol. Chem.*, 268:19126–19133, 1993.
Karlin et al., "Methods for assessing the statistical significance of molecular sequence features by using general scoring schemes," *Proceedings of the National Academy of Sciences of USA*, 87:2264–2268, 1990.
Karlin et al., "Applications and statistics for multiple high–scoring segments in molecular sequences," *Proc. Natl. Acad. Sci. USA*, 90:5873–5877, 1993.
Karsch et al., "Neuroendocrine Basis of Seasonal Reproduction," *Recent Prog. Horm. Res.*, 40:185–232, 1984.
King et al., "Positional Cloning of the Mouse Circadian Clock Gene," *Cell*, 89:641–653, 1997.
Kloss et al., "The Drosophila Clock Gene double–time Encodes a Protein Closely Related to Human Casein Kinase 1∈," *Cell*, 94:97–107, 1998.
Kobayashi et al., "Characterization of photolyase/blue–light receptor homologs in mouse and human cells," *Nucleic Acids Research*, 26:5086–5092, 1998.
Köhler et al., "Continuous cultures of fused cells secreting antibody of predefined specificity," *Nature*, 256:495–497, 1975.
Kozak, "An analysis of 5'–noncoding sequences for 699 vertebrate message RNAs," *Nucleic Acids Res.*, 15:8125–8148, 1987.
Kozbor et al., "The production of monoclonal antibodies from human lymphocytes", *Immunology Today*, 4:72–79, 1983.
Kraft et al., "Chronobiology and Chronotherapy in Medicine," *Disease–A–Month*, 61:501–576, 1995.
Kramer et al., "Oligonucleotide–Directed Construction of Mutations via Gapped Duplex DNA," *Methods in Enzymology*, 154:350–367, 1997.
Kume et al., "mCRY1 and mCRY2 are Essential Components of the Negative Limb of the Circadian Clock Feedback Loop," *Cell*, 98:193–205, 1999.
Kyte et al., "A Simple Method for Displaying the Hydropathic Character of a Protein," *J. Mol. Biol.* 157:105–132, 1982.
Laitinen et al., "Characterization of Melatonin Receptors in the Rat Suprachiasmatic Nuclei: Modulation of Affinity with Cations and Guanine Nucleotides," *Endocrinology* 126:2110–2115, 1990.
Lee et al., "The Drosophila Clock Protein Undergoes Daily Rhythms in Abundance, Phosphorylation, and Interactions with PER–TIM Complex", *Neuron*, 21:857–867, 1998.
Levrero et al., "Defective and nondefective adenovirus vectors for expressing foreign genes in vitro and in vivo", *Gene*, 101:195–202, 1991.
Lisziewicz et al., "Combination Gene Therapy: Synergistic Inhibition of Human Immunodeficiency Virus Tat and Rev Functions by a Single RNA Molecule", *Human Gene Therapy*, 11:807–815, 2000.
Liu et al., "Cellular Construction of a Circadian Clock: Period Determination in the Suprachiasmatic Nuclei", *Cell*, 91:855–860, 1997.
Lyon et al., "Mouse Genome," *Continuation of Mouse Newletter*, 93:1:23:38–39, 1995.

Mahle, et al., "Desensitization of the Melatonin–Mediated Functional Response in RT2–2 Retinal Neuronal Cells," *24th Annual Meeting Soc. Neuroscience*, Miami, FL, 535, 1994 (Abstract).

Miller et al., "Redesign of Retrovirus Package Cell Lines To Avoid Recombination Leading to Helper Virus Production," *Mol. and Cell. Bio.* 6:2895–2902, 1986.

Morgan et al., "Guanine Nucleotides Regulate the Affinity of Melatonin Receptors on the Ovine Pars tuberalis," *Neuroendocrinology*, 50:359–362, 1989.

Morgan et al., "Both Pertussis Toxin–Sensitive and Insensitive G–Proteins Link Melatonin Receptor to Inhibition of Adenylate Cyclase in the Ovine Pars Tuberalis," *J. Neuroendocrinol.* 2:773–776, 1990.

Munson et al., "Ligand: A Versatile Computerized Approached for Characterization of Ligand–Binding Systems," *Anal. Biochem.* 107:220–239, 1980.

Okamura et al., "Photic Induction of mPer1 and mPer2 in Cry–Deficient Mice Lacking a Biological Clock," *Science*, 286:2531–2534, 1999.

Oishi et al., "Rhythmic Expression of BMAL1 mRNA Is Altered in Clock Mutant Mice: Differential Regulation in the Suprachiasmatic Nucleus and Peripheral Tissues," *Biochemical and Biophysical research Communications*, 268: 164–171, 2000.

Price et al., "double–time Is a Novel Drosophila Clock Gene that Regulates Period protein Accumulation," *Cell*, 94:83–95, 1998.

Reeck et al., "Homology in proteins and nucleic acids: a terminology muddle and a way out of it," *Cell*, 50:667, 1987.

Reppert et al., "Putative Melatonin Receptors in a Human Biological Clock," *Science* 242:78–81, 1988.

Reppert et al., "Molecular Cloning and Characterization of a Rat $A_1$—Adenosine Receptor that is Widely Expressed in Brain and Spinal Cord," *Mol. Endocrinol.* 5:1037–1048, 1991.

Reppert et al., "Cloning and Characterization of a Mammalian Melatonin Receptor That Mediates Reproductive and Circadian responses," *Neuron* 13: 1177–1185, 1994.

Reppert et al. "Melatonin Receptors Are for the Birds: Molecular Analysis of Two Receptor Subtypes Differentially Expressed in Chick Brain," *Neuron* 15:1003–1015, 1995.

Reppert et al. "Melatonin receptors step into the light: cloning and classification of subtypes," *Trends in Pharmacological Sciences* 17:100–102, 1996.

Reppert et al., "Strikes Gold: Cloning of a Mammalian Clock Gene," *Cell*, 89:1–4, 1997.

Reppert, "A Clockwork Explosion," *Neuron*, 21:1–4, 1988.

Reppert et al., "Putative Melatonin Receptors in a Human Biological Clock," *Science* 242:78–81, 1988.

Rivkees et al., "Guanine nucleotide–binding protein regulation of melatonin receptors in lizard brain," *Proc. Natl. Acad. Sci. USA* 86:3882–3886, 1989.

Roca et al., "Structure, Characterization, and Expression of the Gene Encoding The Mouse $Mel_{1a}$ Melatonin Receptor," *Endocrinology* 137:3469–3477, 1996.

Rosenthal "Identification of Regulatory Elements of Cloned Genes with Functional Assays," *Methods Enzymol.* 152:704–720, 1987.

Rozen et al., "Structure, characterization, and expression of the rat oxytocin receptor gene," *Proc. Natl. Acad. Sci. USA* 92:200–204, 1995.

Rutila et al., "Cycle Is a Second bHLH–PAS Clock Protein Essential for Circadian Rhythmicity and Transcription of Drosophila period and timeless," *Cell*, 93:805–814, 1998.

Sachs, "Messenger RNA Degradation in Eukaryotes," *Cell* 74:413–421, 1993.

Saez et al., "Regulation of Nuclear Entry of the Drosophila Clock Proteins Period and Timeless", *Neuron*, 17:911–920, 1996.

Sangoram et al., Mammalian Circadian Autoregulatory Loop: A Timeless Ortholog and mPer1 Interact and Negatively Regulate . . . *Neuron* 21:1101–1113, 1998.

Sakamoto et al., "Multitissue Circadian Expression of Rat period Homolog (rPer2) mRNA Is Goverend by the Mammalian Circadian Clock, the Suprachiasmatic Nucleus in the Brain", *The Journal of Biological Chemistry*, 273:27039–27041, 1998.

Schaffer et al., "The late elongated nypocotyl Mutation of Arabidopsis Disrupts Circadian Rhythms and the Photoperiodic Control of Flowering," *Cell*, 93:1219–1229, 1998.

Shearman et al., "Two period Homologs: Circadian Expression and Photic Regulation in the Suprachiasmatic Nuclei," *Neuron*, 19:1261–1269, 1997.

Shearman et al., "Expression of Basic Helizx–Loop–Helix/Pas Geners in the Mouse Suprachiasmatic Nucleus," *Neuroscience*, 89:387–397, 1999.

Shearman et al., "Interacting Molecular Loops in the Mammalian Circadian Clock," *Science*, 288:1013–1019, 2000.

Silver et al., "Multiple regulatory elements result in regional specificity in circadian rhythms of neuropeptide expression in mouse SCN," *NeuroReport*, 10:3165–3174, 1999.

Singer et al., "A wide variety of DNA sequences can functionally replace a yeast TATA element for transcriptional activatyion," *Genes and Development*, 4:636–645, 1990.

Slaugenhaupt et al., "Mapping of the Gene for the Mel1a—Melatonin Receptor to Human Chromosome 4 (MTNR1A) and Mouse Chromosome 8 (Mtnr1a)," *Genomics*, 27:355–357, 1995.

Smith et al., "Single–step purification of polypeptides expressed in *Escherichia coli* as fusions with glutathione S–transferase," *Gene*, 67:31–40, 1988.

Sun et al., "RIGUI, a Putative Mammalian Ortholog of the . . . " *Cell*, 90:1003–1011, 1997.

Takumi et al., "A new mammalian period gene predominantly expressed in the suprachiasmatic nucleus," *Genes to Cells*, 3:167–176, 1998.

Takumi et al., "mouse SCN and OVLT," *The EMBO Journal*, 17:4753–4759, 1998.

Tei et al., "Circadian oscillation of a mammalian homologue of the Drosophila period gene," *Nature*, 389:512–516, 1997.

Thresher et al., "Role of Mouse Cryptochrome Blue–Light Photorecptor in Circadian Photoresponses," *Science*, 282:1490–1494, 1998.

Treacy et al., "I–POU: a POU–domain protein that inhibits neuron–specific gene activation," *Nature*, 350:577–584, 1991.

Tsai–Morris et al. "Structural Organization of the Rat Luteinizing Hormone (LH) Receptor Gene," *J. Biol. Chem.* 266:11355–11359, 1991.

Valerio et al., "Retrovirus–mediated gene transfer into embryonal carcinoma and hemopoietic stem cells: expression from a hybrid long terminal repeat," *Gene*, 84:419–427, 1989.

van der Host et al., "Mammalian Cry1 and Cry2 are essential for maintenance of circadian rhythms," *Nature*, 398:627–630, 1999.

Vaněček "Melatonin Binding Sites," *J. Neurochem.*, 51:1436–1440, 1998.

Vitaterna et al., "Differential regulation of mammalian Period genes and circadian rhythmicity by cryptochromes 1 and 2," *PNAS*, 96:12114–12119, 1999.

Vitaterna et al., "Mutagenesis and Mapping of a Mouse Gene, Clock, Essential for Circadian Behavior," *Science*, 264:719–725, 1994.

Wang et al., "Constitutive Expression of the Circadian Clock Associated (CCA1) Gene Disrupts Circadian Rhythms and Supresses Its Own Expression," *Cell*, 93:1207–1217, 1998.

Weaver et al., "Localization of Melatonin Receptors in Mammalian Brain," Suprachiasmatic Nucleus: the Mind's Clock, Klein, D.C., Moore, R.Y, and Reppert, S.M., eds. New York: Oxford Univ. Press; 289–308. 1991.

Weaver et al., "Localization and Characterization Melatonin Receptors in Rodent Brain by in vitro Autoradiography," *J. of Neuroscience* 9(7): 2581–2590, 1989.

Weaver, "The Suprachiasmatic Nucleus: A 25-Year Retrospective," *Journal of Biological rhythms*, 13:100–112, 1998.

Welsh et al. "Individual Neurons Dissociated from Rat Suprachiasmatic Nucleus Express Independently Phased Circadian Firing Rhythms," *Neuron*, 14:697–706, 1995.

Wobbe et al., "Yeast and Human TATA–Binding Proteins Have Nearly Identical DNA Sequence Requirements for Transcription In Vitro," *Mol. Cell. Biol.* 10:3859–3867, 1990.

Yu et al., "Characterization of Three Splice Variants and Genomic Organization of the Mouse BMAL1 Gene," *Biochemical and Biophysical Research Communications*, 260:760–767, 1999.

Zheng et al., "The mPer2 gene encodes a functional component of the mammalian circadian clock." *Nature*, 400:169–173, 1999.

Zylka et al., "Three Period Homologs in Mammals: Differential Light Responses in the Suprachiasmatic Circadian Clock and Oscillating Transcripts Outside of Brain," *Neuron*, 20:1103–1110, 1998.

Zylka et al., "Molecular Analysis or Mammalian Timeless," *Neuron*, 21:1115–1122, 1998.

|  | INTRACELLULAR LOCALIZATION | TRANSCRIPTIONAL INHIBITION |
|---|---|---|
| mCRY1 — V5 | NUCLEAR | + |
| mCRY1 — HA | NUCLEAR | + |
| HA — mCRY1 | NUCLEAR | + |
| HA — mCRY1 — V5 | NUCLEAR | + |
| mCRY1 — EGFP | DIFFUSE | − |
| EGFP — mCRY1 | DIFFUSE | − |
| EGFP — mCRY1 | CYTOPLASMIC | N.D. |
| EGFP | DIFFUSE | − |
| mCRY2 — HA | NUCLEAR | + |

FIG. 4

| | |
|---|---|
| 1 | ctcagccgag tggcgggaaa ggctgcgacc ccgcacctca gggcctcagg ctctgcgagg |
| 61 | cttcagagga ctcgcggaga gcggtcccgt aggcctcacc ctctccgtcc accatctcta |
| 121 | ctgcccgctc tgctggttgg gcctctggtg tatggacttg tacatgatga actgtgaact |
| 181 | tctagccacg tgtagcgccc ttgggtactt ggaaggaggg acttaccaca aggagccgga |
| 241 | ttgcctggag agtgtgaagg atttgatccg atacctgagg cacgaggatg agacccgaga |
| 301 | tgtgcggcag cagctgggag ctgcacagat cctgcagagc gacctcctgc caatcctcac |
| 361 | gcagcatcgc caggacaagc ctctcttcga tgccgtgatc aggctgatgg taaatttgac |
| 421 | acagccagcc ttgctctgtt ttggcagcgt gcctaaggac tccagtgtac ggcaccattt |
| 481 | tctgcaggtt ctaacgtacc tgcaagccta caaagaggcc tttgccagtg agaaggcatt |
| 541 | tggagtcctc agcgagacct tgtatgaatt gctacagctg ggctgggagg atcggcaaga |
| 601 | agaagacaac ttgctgatcg agcggatcct tctgctggtc agaaatattc tccatgtccc |
| 661 | ggccaacctt gagcaggaga agagtatcga tgatgatgcc agcatccacg accgtctcct |
| 721 | ttgggcaatt caccctcagtg gcatggacga cttgctcctc ttcctgtcca gctcatccgc |
| 781 | cgagcagcag tggagcctcc atgtgctgga gatcatctcc ctcatgttcc gagaccagac |
| 841 | ccctgagcag ctagcgggag tagggcaggg acgcttggct caggagcgaa gcacggatgt |
| 901 | ggcagaattg gaggtgctgc gccaacggga gatggcggag aagagagctc gggccctcca |
| 961 | gcgaggaaac aggcactctc gatttggggg ctcctacatt gtccagggt tgaaatctat |
| 1021 | tggggagaag gatgtcgtct ttcacaaagg ccttcacaat ctccagaact acagctcaga |
| 1081 | tctgggaaag cagcccagga gggtgcccaa gcgtcgtcag gctgcccagg agctgtctgt |
| 1141 | ccatcgccgc tctgtcctga atgtgagact cttcctcaga gacttctgct ctgagttcct |
| 1201 | ggagaactgc tacaacccgc tcatgggcgc ggtcaaggat catctgcttc gggagagagc |
| 1261 | gcagcagcat gacgagactt actacatgtg ggcaatggct ttcttcatgg ccttcaaccg |
| 1321 | agctgccacc ttccgccccg gccttgtttc tgagaccctc agtatccgta cctttcactt |
| 1381 | tgtggagcag aacctcacca actactacga tgatgatgctg acagaccgca aggaggccgc |
| 1441 | ctcctgggcg cgcaggatgc acctggccct gaaggcctac caggagctgc tggccacggt |
| 1501 | gaacgagatg gacatgtgcc cagatgaggc tgttagggag agcagtcgta tcatcaaaaa |
| 1561 | caacattttc tatatgatgg agtaccgaga actattcctg gcgctctttc gaaagtttga |
| 1621 | tgagagatac catccacgct cattccttcg agacctggtg gaaaccaccc acctcttcct |
| 1681 | caaaatgttg gagcgctttt gccggagccg cgggaacctg atggtgcaga acaaaagaaa |
| 1741 | aagaggaaa agaaaaaga aggttcagga ccagggtgtt gcttttctcac aaagccccgg |
| 1801 | ggagctggag gccatgtggc cagccctggc agagcagctg ctgcagtgtg cccaggaccc |
| 1861 | tgagctcagt gtggaccccg tcgttccctt tgatgcggcc tcagaggtgc cagtggagga |
| 1921 | gcagcgggta gaagccatgg tgaggatcca agactgcctt acggctggcc aggccccgca |
| 1981 | agccctggcc ctcctgcggt ctgcccggga agtgtggcct gaaggaaatg cgtttggctc |
| 2041 | tccagtcatt tccccagggg aagaaatgca gttgctgaaa caaatcctct ccacgcccct |
| 2101 | tccccggcag caggagccag aagaaggaga tgcagaggag gaagaggaag aggaggagga |
| 2161 | agaggagtta caggtggtcc aggtgtcaga gaaggagttt aacttctgg aatacctgaa |
| 2221 | acgcttcgca tcctcaacca tcgtgcgggc ctacgtgctt ctcctgcgga gctacaggca |
| 2281 | gaacagtgct cacaccaacc actgcatcgc caagatgctg caccggctgg cccatggcct |

FIG. 6A

```
2341   ggggatggaa gccctgcttt tccagctgtc cctgttctgc ctcttcaatc ggctgcttag
2401   tgacccagct gctgcggcct acaaagagct agtgactttt gccaaataca tcattggcaa
2461   gttctttgcg ttggctgccg tgaaccagaa agcgtttgtg gagctgctat tctggaagaa
2521   caccgcagtg gttcgggaaa tgacccaggg atatggctcc ctcgacagtg ggtcttccag
2581   ccacagagct cctctgtgga gccctgagga agaggcccag cttcaggaac tatacctcgc
2641   ccacaaggat gtggaaggtc aagatgtagt ggaaaccata ttggcgcacc tgaaagtcgt
2701   tcctcgaaca cgcaagcagg tcatccacca cctggtccgg atgggcctgg ccgacagcgt
2761   caaggagttc cagaagagga agggacccca gattgtcttg tggacggagg accaggagct
2821   ggagttacag cggctctttg aggagttccg ggactctgat gatgttcttg gtcaaatcat
2881   gaagaatatc acagccaaac gttcacgggc tcgagtagtg gacaaactgt tggccctggg
2941   gttggtgtct gagcggaggc agctatacaa gaaacggaga aagaagctgg cgccttcttg
3001   catgcagaat ggagaaaagt ccccgagaga cccctggcag gaagatccgg aagaggaaga
3061   cgaacacttg ccagaggacg aaagtgaaga tgaggagagt gaggaaggct tgccatcagg
3121   acagggtcag ggcagctcat ctctctctgc tgaaaacctc ggtgagagcc ttcgtcagga
3181   aggcctctct gctcccctcc tgtggctcca gagctccctg atccgagcag caaatgaccg
3241   agaagaggat ggctgctccc aggcaatccc tctggtgcct ctgacagagg aaaatgagga
3301   agcaatggag aacgaacagt ttcagcatct gctacgcaag ctagggatcc ggccgcccag
3361   ctcagggcag gaaaccttct ggagaattcc agccaaactg agctccaccc agcttcggag
3421   ggtggctgct tctttgagtc agcaagaaaa cgaggaggaa agggaagagg agccagagcc
3481   aggagtcccc ggagagcagg gtcccagtga ggagcaccgg acagaagccc tgagagccct
3541   tctgtcagcc cgtaagagga aagcaggcct ggggcctaca gaagaggagg ccactgggga
3601   ggaagaatgg aactcagcgc ccaagaagcg gcaactgctg gacagcgacg aagaggaaga
3661   tgatgagggg aggaggcaag cagtgtcggg aacgccaaga gtccacagga gaaacggtt
3721   tcagattgag gatgaggatg actgaaagcc agatgtgttt gaccgatgtg agttggaggc
3781   acaaaagcta ctttgcctg cgttggaagc aatcttctct acattgacag cccaggaatt
3841   ttaggcagca gtgttgggtg gagtctttgc ggtcagtcct tgccccaggt tcatcagcgt
3901   gcacagccgg tctctgggtc cgtctcgtag caaatgaaga gtggcgaaag gttcaaggtg
3961   gcttgtcctc ctctaaggac tgcgtcttgg cttctgacgg ggagctttat aacccagcac
4021   ggttgttcat tctgtcctca caaagcactg gattgctccc atttctttc ttcatccca
4081   ggacacatga ttgaacccgt ttctacagtt gagggagagc tgggatgcac cactctcaag
4141   ctgacaagca tccctgattt gtgtttcata ttaaatgtgt acaattaaca gttgctcatc
4201   tcagagcggc cagccagcca tctgttgtgt cttcggaaga acttttaaga gtaaaattaa
4261   aagacatgtc ctgaactgag cttggtagtg tgagctaatc ccatcgtgtg ggagacagag
4321   gcaagagaat tgccatgagg gagaggaaag agtcatatag ccctacgcgt gggccaataa
4381   atgtaattta aaaaatcagc ttgataataa atataatttt taaa
```

FIG. 6B

MDLYMMNCELLATCSALGYLEGGTYHKEPDCLESVKDLIRYLRH
EDETRDVRQQLGAAQILQSDLLPILTQHRQDKPLFDAVIRLMVNLTQPALLCFGSVPK
DSSVRHHFLQVLTYLQAYKEAFASEKAFGVLSETLYELLQLGWEDRQEEDNLLIERIL
LLVRNILHVPANLEQEKSIDDDASIHDRLLWAIHLSGMDDLLLFLSSSSAEQQWSLHV
LEIISLMFRDQTPEQLAGVQGRLAQERSTDVAELEVLRQREMAEKRARALQRGNRHS
RFGGSYTVQGLKSIGEKDVVFHKGLHNLQNYSSDLGKQPRRVPKRRQAAQELSVHRRS
VLNVRLFLRDFCSEFLENCYNPLMGAVKDHLLRERAQQHDETYYMWAMAFFMAFNRAA
TFRPGLVSETLSIRTFHFVEQNLTNYYEMMLTDRKEAASWARRMHLALKAYQELLATV
NEMDMCPDEAVRESSRIIKNNIFYMMEYRELFLALFRKFDERYHPRSFLRDLVETTHL
FLKMLERFCRSRGNLMVQNKRKKRKKKKVQDQGVAFSQSPGELEAMWPALAEQLLQC
AQDPELSVDPVVPFDAASEVPVEEQRVEAMVRIQDCLTAGQAPQALALLRSAREVWPE
GNAFGSPVISPGEEMQLLKQILSTPLPRQQEPEEGDAEEEEEEEEEEELQVVQVSEKE
FNFLEYLKRFASSTTVRAYVLLLRSYRQNSAHTNHCIAKMLHRLAHGLGMEALLFQLS
LFCLFNRLLSDPAAAAYKELVTFAKYIIGKFFALAAVNQKAFVELLFWKNTAVVREMT
QGYGSLDSGSSSHRAPLWSPEEEAQLQELYLAHKDVEGQDVVETILAHLKVVPRTRKQ
VIHHLVRMGLADSVKEFQKRKGTQIVLWTEDQELELQRLFEEFRDSDDVLGQIMKNIT
AKRSRARVVDKLLALGLVSERRQLYKKRRKKLAPSCMQNGEKSPRDPWQEDPEEEDEH
LPEDESEDEESEEGLPSGQGQGSSSLSAENLGESLRQEGLSAPLLWLQSSLIRAANDR
EEDGCSQAIPLVPLTEENEEAMENEQFQHLLRKLGIRPPSSGQETFWRIPAKLSSTQL
RRVAASLSQQENEEEREEEPEPGVPGEQGPSEEHRTEALRALLSARKRKAGLGPTEEE
ATGEEEWNSAPKKRQLLDSDEEEDDEGRRQAVSGTPRVHRKKRFQIEDEDD

FIG. 7

AAGCTGAGCATNAAGGAGACTCTGCCAGGATGGATGAGCTGNGNACTCTTGTTTCCAGAC
AATGTAGCCACCATTGACGTCAATGTAAGCGAGGAAACAAAAGGCCCTTTGGGTGTGTGC
AGGGTGCAGCTTGGCCCAGCTCTGCTCAGTGTTTGTGTGTGTTGGGGAGTGTGGTGAGGT
GTCAGTGTCAGAGGAACCAGAGGTGCTGCCCTGCCCCCTGCAGTGTGAGTCAACATCTGG
CTTCCCAGGGCTTCTTTGGAAAGGGCTGCTGAAATGAACTTAGTCTCTGCCCCCATCTGC
ATCTGANGAATTGCATGCCTGTCCTGCCAGGCAGACAGAAAGAAGTAGCTCCCACACGGA
ATTCTTGAATGTGGGTTAGCCGGCTGTGTACACCAGCAGCTCAGTTTGTTAGCAGACTTC
TGTTGCTAATGTTTGCCTCCTTTCCATTCCTGGTTCCTAGGACACCCCAGGGGAAGATTC
AGAGTAGTGGATGCTACTAGGCTTCAAGTTCCCTGGCAATGACAAATGACCTTTTTACCC
TTGGAAGACGTGACAAGCTTGCCTTCTCCATCACACCTTGCATGAGTCTTTAGGTTGTTC
TCTGTCAGCCTCAAACCCGCTCCGAGGAAACTTCTACTCCCTCCTTTGACCCTTTGGACA
GGAGCCTGAACGCTTTAGTAGGCTTCCAGACAGTGCTCTTGAAAGAACCAAATAGCTTCA
ACCAAGGTTCCACAGGGGCAGGGCTGTCCTATCACTGGAGGAGTACCCTCCCCTGACTAG
CTAGTGTCTGTAGCTTCCACTTCAGAAWAGCCCTGMTGTTCCAGATGCACACCCCCGCTT
CCATAGTTCCTGTAAGGTTAATAAACTACACCACCGCATTTGGTTAAGCTTCCCTGTAGA
ACGTCAGTCTTCTCTCCCTATGTGATTGAGGGCAGGAAGAAATCACTTCTTTCCTTTGTA
TCTCTGCACGGCAATTATGACCTTATTTCCTGAATCAACACTAACTAGCAAGACGCAGTT
TCAGAAACAAGAAAGGCTAAGTGGGAGTTTTGTGCTTTGGCCCATCTGGAATGACGGTCA
GCCTGGGGGGCCTGTCCTAGGGTCACCCAGCCTGTCCTGGGAAGGTGCTCAGCAGCAGAT
CCAGAGGGGCCGTCCTATTTGTCCTCAAGCGTCTCGCCATGAATGAATGAGAGGGGAAAT
GAATGAACTGGGCTGGATGAGCGAAAGGTGTCAGCAGAGAGCATTCTCGGTCCTTCGGAT
TACCGAGGCTGGTCACGTCGTCGCAGGTGATAGGCCGGGGGCCCTG-TCTCTGCCGGCTG
TGAGTTGCGCAGCGGCCAAGCACCATTCCCCGCGCCGCAGTGGTACGCGCCACTCCGGG
GCTGCACGAGCGGGCCACCGCCGTGCCAGGTGAATGGAAGTCCCGCAGGCCGGAAGTGGA
CGAGCCTACTCGCCCGGGCGCGGGGGGCGCAAGAGCGCGCAGCATCTTCATTGAGGAAC
CCGGGCGGCGAACATGGAGTTCCATGTGCGTCTTATGTAAAGAGAGCGACGGGCGTCTCC
ACCAATTGACGAGCGTAGCTCTCAGGTTCCGCCCCGCCAGTATGCAAATGAGGTGGCACT
CCGACCAATGGCGCGCGCAGGGCGGGCTCAGCGCGCGCGGTCACGTTTTTCCACTATGT
GACAGCGGAGGGCGACGCGGCGGCAGCGGCGCTAACTAGTG (SEQ ID NO:3)

FIG. 8

|  | −mCRY1 | | | +mCRY1 | | |
|---|---|---|---|---|---|---|
|  | C | B | N | C | B | N |
| mPER2 1-1257 | 67 | 33 | 0 | 0 | 2 | 98 |
| mPER2 1-337 | 9 | 89 | 2 | 9 | 91 | 0 |
| mPER2 338-1257 | 84 | 8 | 8 | 12 | 3 | 85 |
| mPER2 BRDM1 | 100 | 0 | 0 | 9 | 81 | 10 |

FIG. 13

METHODS FOR IDENTIFYING COMPOUNDS WHICH MODULATE CIRCADIAN RHYTHM

CROSS REFERENCE TO RELATED APPLICATIONS

This application claims priority from U.S. Provisional Application Ser. No. 60/203,005 filed May 10, 2000, and U.S. Provisional Application Serial No. 60/145,363, filed Jul. 22, 1999, these applications are incorporated herein by reference in their entirety.

FIELD OF THE INVENTION

The field of the invention relates to the regulation of circadian rhythms.

BACKGROUND OF THE INVENTION

Circadian rhythms in mammals are regulated by a master clock located in the suprachiasmatic nucleus (SCN) of the brain (Klein et al., Suprachiasmatic nucleus: The Mind's Clock, Oxford University Press, New York, 1991; Reppert and Weaver, Cell 89:487–490, 1997). Environmental light-dark cycles entrain the SCN clock to the 24-hr day via direct and indirect retinal projections. The timekeeping capability of the SCN is expressed at the level of single neurons (Welsh et al., Neuron 14:697–706, 1995).

The SCN clock mechanism is cell-autonomous, possibly based on transcriptional and translational negative feedback loops (Reppert, Neuron 21:1–4, 1998). Precedent for such a mechanism has been described for circadian clocks in the fly Drosophila melanogaster.

In the fly, autoregulatory transcriptional loops occur in which protein products of clock genes periodically enter the nucleus to suppress their own transcription. This feedback loop involves dynamic regulation of the clock genes period (per) and timeless (Tim). As the levels of PER and TIM rise, they are phosphorylated, form heterodimers, and are then translocated to the nucleus where they negatively regulate their own transcription (Saez and Young, Neuron 17:1–920, 1996; Darlington et al., Science 280:1599–1603, 1998). Negative transcriptional regulation appears to involve interference with drosophila CLOCK:drosophila dBMAL-1 (dCLOCK:dBMAL-1) and may be mediated by direct interaction of PER and TIM with dCLOCK. dCLOCK and dBMAL-1 are positive factors which drive Per and Tim transcriptional activation by binding to CACGTG E-box enhancers in the promoters of Per and Tim (Allada et al., Cell 93:791–804, 1998; Rutila et al., Cell 93:805–814, 1998; Darlington et al., supra; Hao et al., Mol. Cell Biol. 17:3687–3693, 1997). The temporal phosphorylation of PER provides at least part of the time delay between transcription and PER-TIM negative feedback necessary to sustain a 24-hr molecular oscillation in drosophila (Price et al., Cell 94:83–95, 1998).

SUMMARY OF THE INVENTION

The invention is based, in part, on the discovery that the core clockwork in the SCN is comprised of interacting feedback loops. It was discovered that cryptochrome (CRY) proteins are critical players in the negative limb of the mammalian clock feedback loop and Period 2 (PER2) protein is a critical regulator of the Bmal-1 loop. The CRY proteins and PER2 protein therefore function as important modulators of mammalian circadian rhythm.

It was discovered that mammalian CRY proteins can translocate from the cytoplasm to the nucleus of a cell and inhibit CLOCK:BMAL-1 induced transcription. It was also discovered that CRY proteins can homodimerize or heterodimerize with other circadian proteins. The ability of CRY to heterodimerize with other proteins provides a mechanism whereby CRY can modulate the activity of other circadian proteins. For example, mouse CRY proteins can function as dimeric and potentially trimeric partners for mouse PER proteins; these interactions lead to the nuclear translocation of PER. Once in the nucleus, PER can inhibit CLOCK:BMAL-1 induced transcription. In addition, it was discovered that mouse CRY can form heterodimeric complexes with mouse TIM. The interaction of TIM with CRY may have a role in modulating the negative feedback of mouse PER and/or mouse CRY rhythms. Thus, the compounds which can disrupt the interaction of CRY with itself and other circadian proteins can be used to reset the circadian clock.

In addition, it was discovered that PER2 positively regulates transcription of the Bmal-1 gene. The ability of PER2 to positively regulate the transcription of Bmal-1 indicates that PER2 controls the rhythmic regulation of Bmal-1. The availability of BMAL-1 is critical for restarting the circadian clock loop. When BMAL-1 is available, it heterodimerizes with CLOCK, thereby driving the transcription of Per genes (e.g., in the mouse(m), mPER1–3) and Cryptochrome genes (e.g., mouse mCry1 and mCry2). Compounds which can disrupt the ability of PER2 to positively activate Bmal-1, or compounds which can modulate transcription of Bmal-1, can be used to reset the circadian clock.

Accordingly, the invention includes a method for identifying a compound which binds to a mammalian CRY protein. The method, which is useful as a quick initial screen for CRY agonists and antagonists, includes contacting the CRY protein with a test compound and determining whether the latter binds to the CRY protein. Binding by the test compound to the CRY protein indicates that the test compound is a CRY protein binding compound. For ease of detection, the test compound can be labeled, e.g., radiolabeled. The CRY protein can any mammalian CRY protein such as a CRY from a mouse, rat, rabbit, goat, horse, cow, pig, dog, cat, sheep, pig, non-human, primate, or human. In particular, the CRY protein is a mouse CRY1 or CRY2 or human CRY1 or CRY2.

The method may further include contacting the test compound with: a CRY protein in the presence of a PER protein; a CRY protein in the presence of a TIM protein; a CRY protein in the presence of a CLOCK:BMAL-1 complex; or a CRY protein in the presence of a BMAL-1 protein; and determining whether the test compound disrupts the association of the CRY protein with the PER, TIM, CLOCK:BMAL-1, or BMAL-1 protein, as the case may be; wherein a decrease in the association in the presence of the test compound compared to the association in the absence of the test compound indicates that the test compound disrupts the association of the CRY protein with the indicated binding partner. The PER protein can any mammalian PER protein such as mouse, rat, rabbit, goat, horse, cow, pig, dog, cat or human. For example, the PER protein may be mouse or human PER1, PER2 or PER3.

The method can further include contacting the test compound with the first CRY protein in the presence of a second CRY protein and determining whether the test compound disrupts the association of the first CRY protein with the second CRY protein, wherein the second CRY protein has an amino acid sequence the same as or different than the first CRY protein, and wherein a decrease in the association in the presence of the test compound compared to the association in the absence of the test compound indicates that the test compound disrupts the association of the first CRY protein and the second CRY protein. The first and second CRY proteins can be any mammalian CRY protein such as a CRY from a mouse, rat, rabbit, goat, horse, cow, pig, dog, cat, sheep, non-human, primate or human. For example, each CRY protein can be a mouse or human CRY1 or CRY2 and the second CRY protein is a mouse CRY1 or CRY2.

The method can further include providing a cell or cell-free system which includes a CRY protein, a CLOCK:BMAL-1 complex, and a DNA comprising an E-box operatively linked to a reporter gene. The method includes introducing the test compound into the cell or cell-free system and assaying for transcription of the reporter gene, wherein an increase in transcription in the presence of the compound compared to transcription in the absence of the compound indicates that the compound blocks CRY-induced inhibition of CLOCK:BMAL-1-mediated transcription in a cell. The cell can be any cell type, such as a cultured mammalian cell, e.g., a NIH3T3 cell, a COS7 cell, or a clock neuron. The reporter gene can be a gene that encodes a detectable marker, e.g., luciferase.

The invention further includes a method for identifying a compound which disrupts the association of a CRY protein and a second protein or protein complex, which can be any of the following: a PER protein, a TIM protein, a BMAL-1 protein, a second CRY protein, or a CLOCK:BMAL-1 complex. The method includes contacting a test compound with the CRY protein in the presence of the second protein (or protein complex) and determining whether the test compound disrupts the association of the CRY protein and the second protein (or protein complex), wherein a decrease in the association in the presence of the test compound compared to the association in the absence of the test compound indicates that the test compound disrupts the association of the CRY protein and the second protein. The first and second CRY proteins can be any mammalian CRY protein such as a CRY protein from a mouse, rat, rabbit, goat, horse, cow, sheep, pig, dog, cat, non-human primate or human, e.g., a mouse or human CRY1 or CRY2. The PER protein can be any mammalian PER protein as described above, e.g., a mouse PER1, PER2 or PER3. The TIM protein can be any mammalian TIM protein as described above, e.g., a mouse or human TIM protein. The CLOCK and the BMAL-1 proteins can be any mammalian CLOCK and BMAL-1 proteins as described above, particularly mouse or human.

Also within the invention is a method for identifying a compound that blocks CRY-induced inhibition of CLOCK:BMAL-1 transcription in a cell. The method includes providing a cell comprising a CRY protein, a CLOCK:BMAL-1 complex, and a DNA comprising an E-box operatively linked to a reporter gene; introducing the compound into the cell or a cell-free transcription system; and assaying for transcription of the reporter gene, wherein an increase in transcription in the presence of the compound compared to transcription in the absence of the compound indicates that the compound blocks CRY-induced inhibition of CLOCK:BMAL-1-mediated transcription. The cell can be any cell type, such as a cultured mammalian cell, e.g., a NIH3T3 cell, a COS7 cell or a clock neuron. The reporter gene can be gene that encodes a detectable marker, e.g., luciferase.

The invention further includes a method for identifying a compound that activates or inhibits the transcription of Per2. The method includes providing a cell including a mammalian Per2 regulatory sequence operatively linked to a reporter gene, introducing a test compound into the cell, and assaying for transcription of the reporter gene in the cell. A decrease in transcription in the presence of the compound compared to transcription in the absence of the compound indicates that the compound inhibits Per2 transcription in a cell. Likewise, an increase of transcription in the presence of the compound compared to transcription in the absence of the compound indicates that the compound inhibits Per2 transcription in a cell. The cell can be any cell that can generate circadian rhythms, such as a NIH3T3 cell, a Cos-7 cell or a clock neuron. The reporter gene can be any detectable marker, e.g., a luciferase, a chloramphenicol acetyl transferase, a beta- galactosidase, an alkaline phosphate, or a fluorescent protein such as green fluorescent protein. The Per2 regulatory sequence can be any mammalian Per2 regulatory sequence, e.g., from a mouse, a rat, a rabbit, a goat, a horse, a cow, a pig, a dog, a cat, a sheep, a non-human primate, or a human. In particular, the Per2 regulatory sequence can be a mouse Per2 regulatory sequence (SEQ ID NO:3).

Also within the invention is a method of determining if a candidate compound positively regulates the expression of Bmal-1. The method includes providing a transgenic animal whose somatic and germ cells comprise a disrupted Per2 gene, the disruption being sufficient to inhibit the ability of Per2 to positively regulate Bmal-1, administering a test compound to the mouse, and detecting Bmal-1 expression, wherein an increase in the expression of Bmal-1 indicates that the compound can positively regulate expression of Bmal-1.

The invention also features a method of modulating circadian-clock controlled rhythms in a cell including comprising introducing into a cell an expression vector encoding a BMAL-1 protein such that an effective amount of the BMAL-1 protein is produced in the cell, thereby modulating circadian-clock controlled rhythms. The BMAL-1 can be any mammalian BMAL-1, e.g., that of a mouse, a rat, a rabbit, a goat, a horse, a cow, a dog, a cat, a sheep, a non-human primate, or a human BMAL-1.

Also within the invention is a method of modulating circadian-clock controlled rhythms in a cell comprising introducing into the cell an effective amount of an oligonucleotide antisense to a part, or all, of a mammalian Bmal-1, thereby inhibiting expression of Bmal-1 in the cell and modulating circadian-clock rhythms. Oligonucleotides can be antisense to any mammalian Bmal-1, e.g., Bmal-1 from a mouse, a rat, a rabbit, a goat, a horse, a cow, a sheep, a non-human primate, or a human.

The invention further includes isolated nucleic acid molecules which are at least about 60% (or 65%, 75%, 85%, 95%, or 98%) identical to the nucleotide sequence of mouse TIMELESS (TIM) (SEQ ID NO:1). The invention also features isolated nucleic acid molecules which include a fragment of at least 100 (e.g., at least 200, 300, 400, 500, 600, 700, 800, 900, 1000, 1500, 2000, 2500, 3000, 3500, or 3745) nucleotides of the nucleotide sequence of SEQ ID NO: 1, or a complement thereof. The invention also features nucleic acid molecules which include a nucleotide sequence encoding a protein having an amino acid sequence that is at least about 60% (or 70%, 75%, 85%, 95%, or 98%) identical to the amino acid sequence of SEQ ID NO:2. In a preferred embodiment, the isolated nucleic acid molecule has the nucleotide sequence of SEQ ID NO: 1, or a complement thereof Also within the invention is an isolated polypeptide having an amino acid sequence that is at least about 60%, preferably 70%, 75%, 85%, 95%, or 98%, identical to the amino acid sequence of SEQ ID NO:2. Also within the invention are isolated polypeptides encoded by a nucleic acid molecule having a nucleotide sequence which hybridizes under stringent hybridization conditions to the complement of SEQ ID NO: 1.

The invention also features isolated nucleic acid molecules which are at least about 60% (or 65%, 75%, 85%, 95%, or 98%) identical to the mouse Per2 upstream sequence (SEQ ID NO:3) containing a sequence controlling expression of mouse Per2. The invention also features isolated nucleic acid molecules which include a fragment of at least 100 (e.g., at least 200, 300, 400, 500, 600, 700, 800, 900, or 950) nucleotides of the nucleotide sequence of SEQ ID NO:3, or a complement thereof.

The invention also includes nucleic acid molecules that hybridize under stringent conditions to a nucleic acid molecule having the nucleotide sequence of SEQ ID NO:1 or SEQ ID NO:3. The nucleic acid molecules can be, for example, at least 20 (e.g. at least about 30, 40, 50, 70, 100, 150, 200, 300, 400, 500, 600, 700, 800, 900, 1000, 1500, 2000, 2500, 3000, 3500, or 3745) nucleotides in length.

Another aspect of the invention provides vectors, e.g., recombinant expression vectors, comprising a nucleic acid molecule described herein. The vector or nucleic acid molecule can be provided in a host cell. Such cells may be utilized for producing a polypeptide of the invention by culturing the cells in a suitable medium.

Also within the invention are a substantially pure preparation of a mouse or human TIM, a mouse or human CRY:PER heterodimer, a CRY:TIM heterodimer, and a mammalian CRY:CRY homodimer.

Isolated antibodies, which specifically bind to mouse CRY, mouse PER, mouse TIM, mouse BMAL-1 are also within the invention.

As used herein, "isolated DNA" means either DNA with a non-naturally occurring sequence or DNA free of the genes that flank the DNA in the genome of the organism in which the DNA naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment.

As used herein, an regulatory sequence which is "operably linked" to a second sequence (or vise versa) means that both are incorporated into a genetic construct so that the regulatory sequence effectively controls expression of a second sequence.

As used herein, a "substantially pure" protein refers to a protein which either (Klein et al., (1991). Suprachiasmatic nucleus: The Mind's Clock, Oxford University Press, New York. has a non-naturally occurring sequence (e.g., mutated, truncated, chimeric, or completely artificial), or (D. R. Weaver, J. Biol. Rhythms 13, 100 (1998) has a naturally occurring sequence but is not accompanied by or at least partially separated from, components that naturally accompany it. Typically, the protein is substantially pure when it is at least 60% (by weight) free from the proteins and other naturally-occurring organic molecules with which it is naturally associated. Preferably, the purity of the preparation is at least 75%, more preferably at least 90%, and most preferably at least 99%, by weight. A substantially pure protein can be obtained, for example, by extraction from a natural source, by expression of a recombinant nucleic acid encoding the protein or by chemical synthesis. Purity can be measured by any appropriate method, e.g., column chromatography, polyacrylamide gel electrophoresis, or HPLC analysis. A chemically synthesized protein or a recombinant protein produced in a cell type other than the cell type in which it naturally occurs is, by definition, substantially free from components that naturally accompany it. Accordingly, substantially pure proteins include those having sequences derived from eukaryotic organisms but synthesized in *E. coli* or other prokaryotes.

As used herein, the term "vector" refers to a replicable nucleic acid construct. Examples of vectors include plasmids and viral nucleic acids.

As used herein, a "circadian protein" refers to a protein that participates in the circadian timing system and controls circadian rhythm. Examples of circadian proteins include PER, TIM, CLOCK, and BMAL-1.

As used herein, an antibody that "specifically binds" a mouse or human CRY, PER or TIM, respectively, is an antibody that binds only to mouse or human CRY, PER or TIM and does not bind to (i) other molecules in a biological sample or (ii) CRY, PER or TIM of another organism.

As used herein, a "therapeutically effective amount" is an amount of the nucleic acid of the invention which is capable of producing a medically desirable result in a treated animal.

As used herein, a "reporter gene" means a gene whose expression can be assayed.

As used herein, the terms "heterologous DNA" or "heterologous nucleic acid" is meant to include DNA that does not occur naturally as part of the genome in which it is present, or DNA which is found in a location or locations in the genome that differs from that in which it occurs in nature, or occurs extra-chromasomally, e.g., as part of a plasmid.

Unless otherwise defined, all technical and scientific terms used herein have the same meaning as commonly understood by one of ordinary skill in the art to which this invention pertains. The preferred methods and materials are described below, although methods and materials similar or equivalent to those described herein can be used in the practice or testing of the present invention. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

BRIEF DESCRIPTION OF THE DRAWINGS

FIG. 4 is a schematic representation of epitope-tagged mouse CRY1 and CRY2 proteins evaluated for cellular location and inhibition of Clock:Bmal-1 mediated transcription.

FIG. 6 (1 of 2) and FIG. 6 (2 of 2) is a representation of the nucleotide sequence of mouse TIM (SEQ. ID NO:1).

FIG. 7 is a representation of the amino acid sequence of mouse TIM (SEQ. ID NO:2).

FIG. 8 is a representation of the nucleotide sequence of the regulatory sequence of mouse Per2 (SEQ. ID NO:3).

FIG. 13 is a schematic representation of different mPER2 constructs with a V5 epitope tagged at the carboxyl terminus of mPER2. Also shown is the cellular location of immunofluorescence of V5-tagged mPER2 constructs expressed in COS-7 cells either with (+) or without (−) mCRY1. The cellular location of immunofluorscence was scored as one of three categories: cytoplasm only (C), both cytoplasm and nucleus (B), or nucleus only (N). Values shown are the mean percentages from two experiments; all values were within 17% of the mean. Gray bars are PAS domain.

DETAILED DESCRIPTION

It has been discovered that members of the mouse PER family (PER1, PER2, and PER3), the mouse CRY family (CRY1, and CRY2) and mouse TIM can interact directly with each other. The ability of these proteins to interact is critically involved in regulating circadian rhythm. More specifically, PER, CRY and TIM control circadian rhythm by inhibiting the transcriptional feedback loop which is at the heart of the mammalian circadian clock.

It was also discovered that PER2 positively regulates the transcription of Bmal-1, thereby controlling the rhythmic regulation of Bmal-1. BMAL1-1 functions as a positive regulator in the circadian loop. More specifically, BMAL-1 forms a heterodimeric protein with CLOCK, which heterodimer in turn positively regulates the expression of the circadian genes such as PER or CRY.

Figure 18:
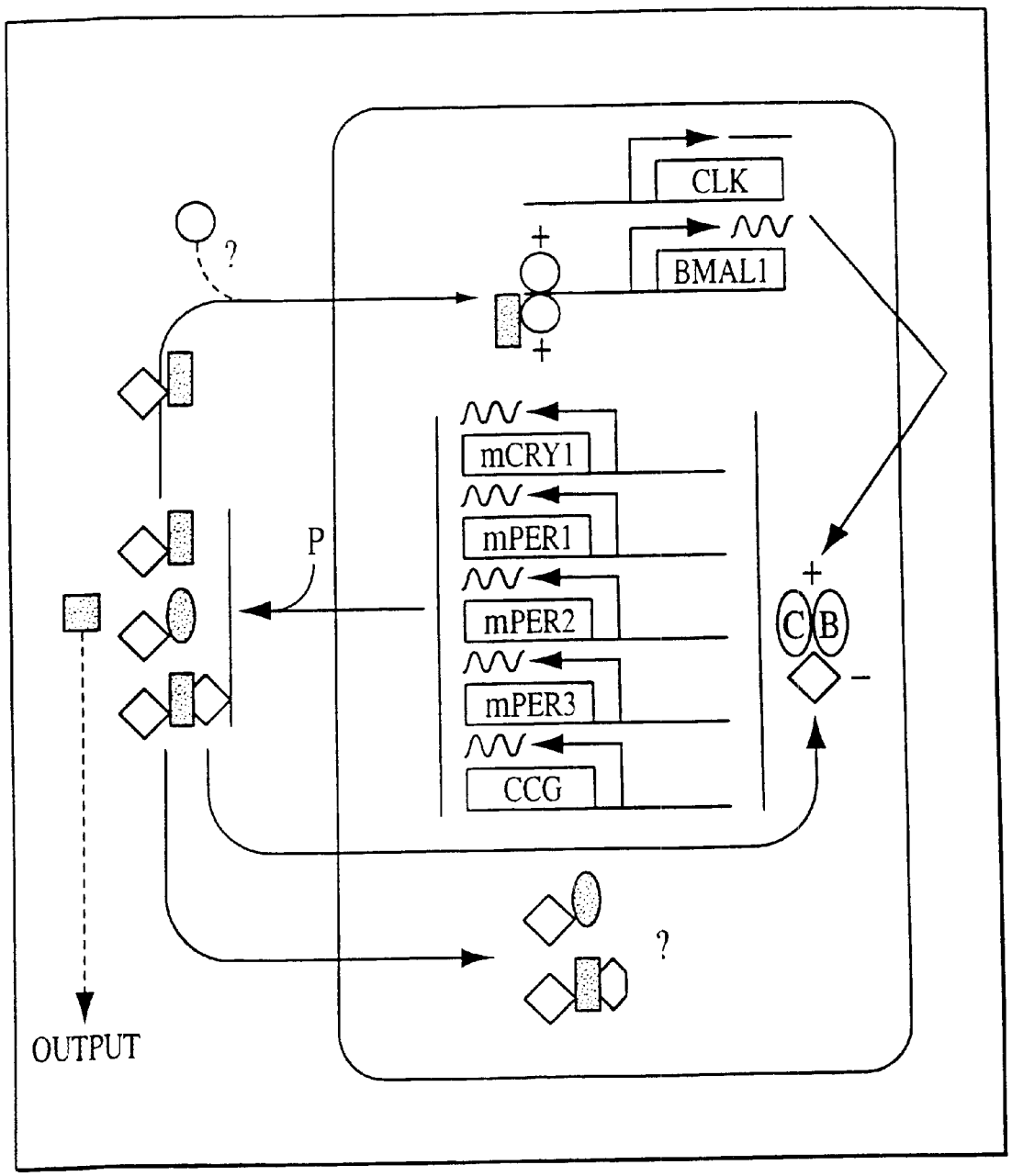
FIG. 18 is a schematic drawing depicting a model of circadian clockwork within an individual SCN neuron.

Based on the discovery made herein, the SCN clockwork is predicted to include three types of interacting molecular loops (FIG. 18). The Cry genes comprise one loop that has true autoregulatory, negative feedback features, with the protein products feeding back to turn off their transcription. The second loop is that manifested by each of the Per genes and some clock-controlled genes (CCGs) (for example, vasopressin prepropressophysin). This loop type is driven by the same positive elements (CLOCK(C):BMAL1(B)) as the CRY loop, but is not turned off by the respective gene products. Instead, these loops use the CRY proteins as negative regulators, leaving the generated protein products free to transduce other actions. For example, PER2 is used for the positive transcriptional regulation of the Bmal-1 gene. The rhythmic regulation of Bmal-1 comprises the third loop, whose rhythmicity is controlled by the cycling presence and absence of a positive element dependent upon mPER2. This positive feedback loop functions to augment the positive regulation of the first two loops.

This model of interacting loops proposes that at the start of the circadian day PER and CRY transcription are driven by accumulating CLOCK:BMAL1 heterodimers acting through E box enhancers. After a delay, the PER and CRY proteins are synchronously expressed in the nucleus where the CRY proteins shut off Clock:Bmal1-mediated transcription by directly interacting with these transcription factors. At the same time that the CRY proteins are inhibiting Clock:Bmal-1-mediated transcription, PER2 either shuttles a transcriptional activator into the nucleus or coactivates a transcriptional complex to enhance Bmal-1 transcription. The importance of the Bmal-1 RNA rhythm is to drive a Bmal-1 rhythm after a 4 to 6 hour delay. This delay in the protein rhythm would provide increasingly available CLOCK:BMAL1 heterodimers at the appropriate circadian time to drive Per and Cry transcription, thereby restarting the cycle. It is thus predicted that BMAL-1 availability is rate limiting for heterodimer formation and critical for restarting the loops.

TIM Nucleic Acid Molecules

The invention pertains to isolated nucleic acid molecules that encode mouse TIM proteins or biologically active portions thereof, as well as nucleic acid molecules which can serve as hybridization probes to identify TIM-encoding nucleic acids (e.g., TIM mRNA), or as PCR primers for the amplification or mutation of TIM nucleic acid molecules. The nucleic acid encoding mouse TIM (SEQ ID NO:1) (and/or the complement of that nucleic acid) can be used as a probe to identify nucleic acids related to the mouse TIM gene, e.g., other naturally occurring mammalian TIM DNA's .

Fragments of SEQ ID NO:1 and its complement can be used as probes or primers, so long as they are at least 10, and preferably at least 15 (e.g., at least 18, 20, 25, 50, 100, 150, or 200) nucleotides in length. TIM probes and primers can be produced using any of several standard methods (see, e.g., Ausubel et al., 1989, *Current Protocols in Molecular Biology*, Vol. I, Green Publishing Associates, Inc., and John Wiley & Sons, Inc., NY). For example, the probe can be generated using PCR amplification methods in which oligonucleotide primers are used to amplify a portion of SEQ ID NO:1 that can be used as a specific probe. Such probes and primers are part of the invention.

Hybridization under stringent conditions can be used to identify nucleic acid sequences which encode mouse TIM or other related TIMs, e.g., other mammalian TIM proteins. A related nucleic acid sequence has at least 50% sequence identity to mouse TIM cDNA (SEQ ID NO:1). Standard hybridization conditions (e.g., moderate or highly stringent conditions) are known to those skilled in the art and can be found in Current *Protocols in Molecular Biology*, John Wiley & Sons, N.Y. (1989), 6.3.1–6.3.6, hereby incorporated by reference. Moderate hybridization conditions are defined as equivalent to hybridization in 2×sodium chloride/sodium citrate (SSC) at 30° C., followed by one or more washes in 1×SSC, 0.1% SDS at 60° C. Highly stringent conditions are defined as equivalent to hybridization in 6×sodium chloride/sodium citrate (SSC) at 45° C., followed by one or more washes in 0.2×SSC, 0.1% SDS at 65° C.

Nucleic acids which hybridize to the above-described probes under stringent conditions can be used as probes themselves to analyze the expression of mouse TIM mRNA in the SCN. These nucleic acids can also be used to express mouse TIM polypeptides or immunogenic fragments thereof for raising mouse TIM antibodies.

Genomic fragments of the TIM locus that are hybridizable to the above-described probes are also included in the invention. Such fragments are useful starting materials for generating, e.g., knockout constructs that are used to create non-human transgenic mammals containing null mutations at the TIM locus.

The invention further encompasses nucleic acid molecules that differ from the nucleotide sequence of SEQ ID NO:1 due to degeneracy of the genetic code, and thus encode the same TIM protein as that encoded by the nucleotide sequence shown in SEQ ID NO:1.

Mutations which change the nucleotide sequence of SEQ ID NO:1 without altering the functional activity of the TIM protein are also within the scope of the invention. For example, one can make nucleotide substitutions leading to amino acid substitutions at "non-essential" amino acid residues. A "non-essential" amino acid residue is a residue that can be altered from the wild-type sequence of mouse TIM (e.g., the sequence of SEQ ID NO:2) without altering the biological activity, whereas an "essential" amino acid residue is required for biological activity. For example, amino acid residues that are conserved among the TIM proteins of various species are predicted to be particularly unamenable to alteration. These can be identified by sequence comparison among the known TIM proteins (yeast, Drosphylia and now, mouse) Thus, the invention encompasses nucleic acid molecules encoding mouse TIM proteins that contain changes in amino acid residues that are not essential for activity. Such TIM proteins differ in amino acid sequence from SEQ ID NO:2, yet retain biological activity.

An isolated nucleic acid molecule encoding a TIM protein having a sequence which differs from that of SEQ ID NO:2 can be created by introducing one or more nucleotide substitutions, additions or deletions into the nucleotide sequence of SEQ ID NO:1 such that one or more amino acid substitutions, additions or deletions are introduced into the encoded protein. Mutations can be introduced by standard techniques, such as site-directed mutagenesis and PCR-mediated mutagenesis. Generally, additions or deletions of nucleotides will be done in multiples of three, so as to avoid a frame shift.

TIM Polypeptides

A mouse TIM polypeptide can be isolated and purified from a natural source. Alternatively, it can be produced recombinantly or chemically synthesized by conventional methods. A TIM polypeptide, full-length or truncated, can also be part of a fusion protein, for example, by linking it to an antigenic determinant to facilitate purification. The TIM polypeptides can be prepared for a variety of uses, e.g., generation of antibodies which can be used to detect TIM, and in screening assays which identify compounds that disrupt the association of TIM with CRY.

Techniques for generating substantially pure polypeptide preparations are well known in the art. A typical method involves transfecting host cells (e.g., bacterial cells such as *E. coli*, or mammalian cells such as COS7) with an expression vector carrying a nucleic acid that encodes a mouse TIM protein. The recombinant polypeptide so produced can be purified from the culture medium or from lysates of the cells.

Conventional site-directed mutagenesis techniques can be applied to a TIM coding sequence, e.g., SEQ ID NO:1, to generate TIM sequence variants optimized for expression in a given type of host cell.

Furthermore, one skilled in the art can prepare not only a natural mouse TIM protein with a naturally occurring sequence (SEQ ID NO:2), but also proteins with substantially the same function as that of the natural protein, by replacing amino acids in the protein. Methods for amino acid alteration include, for example, a site-directed mutagenesis system using PCR (GIBCO-BRL, Gaithersburg, Md.); the oligonucleotide-mediated site-directed mutagenesis method (Kramer, *Methods in Enzymol*. 154:350–367 1997); and the Kunkel method (*Methods Enzymol*. 85:2763–2766, 1988). Usually ten or fewer, preferably six or fewer, and more preferably three or fewer amino acids (e.g., one or two) are substituted. Proteins functionally equivalent to the TIM protein can be produced by conservative amino acid substitutions at one or more amino acid residues. A "conservative amino acid substitution" is one in which the amino acid residue is replaced with an amino acid residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Biologically active portions of a mouse TIM protein include peptides comprising amino acid sequences identical to or derived from the amino acid sequence of the mouse TIM protein (e.g., the amino acid sequence shown in SEQ ID NO:2).

A TIM protein that has a high sequence identity to SEQ ID NO:2 is also included in the invention. A useful TIM protein has an amino acid sequence at least 60% identical, preferably at least 70%, more preferably at least 80%, and even more preferably at least 90, 95, 96, 97, 98 or 99% identical to the amino acid sequence of SEQ ID NO:2, and retains the functional activity of the TIM protein of SEQ ID NO:2.

To determine the percent sequence identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In one embodiment, the two sequences are the same length.

To determine percent homology between two sequences, the algorithm of Karlin and Altschul (*Proc. Natl. Acad. Sci. USA* 87:2264–2268, 1990), modified as in Karlin and Altschul (i Proc. Natl. Acad. Sci. USA 90:5873–5877, 1993), is used. Such an algorithm is incorporated into the NBLAST and XBLAST programs of Altschul et al. (*J. Mol. Biol.* 215:403–410, 1990. BLAST nucleotide searches are performed with the NBLAST program, score=100, wordlength=12 to obtain nucleotide sequences homologous to a nucleic acid molecules of the invention. BLAST protein searches are performed with the XBLAST program, score=50, wordlength=3 to obtain amino acid sequences homologous to mouse TIM protein. To obtain gapped alignments for comparison purposes, Gapped BLAST is utilized as described in Altschul et al. (*Nucleic Acids Res.* 25:3389–3402, 1997). When utilizing BLAST and Gapped BLAST programs, the default parameters of the respective programs (e.g., XBLAST and NBLAST) are used. See http://www.ncbi.nlm.nih.gov.

Per2 Regulatory Sequence

The invention pertains to an isolated genomic nucleic acid molecule that includes the mouse Per2 regulatory sequence (promoter/enhancer sequence), as well as nucleic acid molecules which can serve as hybridization probes to identify a Per2 regulatory sequence, or as PCR primers for the amplification or mutation of a Per2 regulatory sequence.

Fragments of mouse Per2 regulatory sequence (SEQ ID NO:3) and its complement can be used as probes or primers, so long as they are at least 10, and preferably at least 15 (e.g., at least 18, 20, 25, 50, 100, 150, or 200) nucleotides in length. PER2 regulatory sequence probes and primers can be produced using any of several standard methods described above. For example, the probe can be generated using PCR amplification methods in which oligonucleotide primers are used to amplify a portion of SEQ ID NO:3 that can be used as a specific probe.

Other uses for the Per2 regulatory sequence include use as a starting material for generating, e.g., knockout constructs that are used to create non-human transgenic mammals that contain a disruption in the Per2 regulatory sequence and that are unable to express Per2. Alternatively, the Per2 regulatory sequence may be operably linked to a DNA sequence encoding a polypeptide that is not PER2 (i.e., a heterologous polypeptide).

Hybridization under stringent conditions can be used to identify nucleic acid sequences that contain a regulatory sequence of mouse PER2, or other related PER2 regulatory seqeuences. A related nucleic acid sequence has at least 50% sequence identity to mouse PER2 regulatory sequence (SEQ ID NO:3). Standard hybridization conditions are described above.

Circadian Proteins

The invention includes screening methods which are used to identify compounds which can disrupt the association of mammalian circadian proteins, e.g., the association of TIM with CRY, CRY with CRY, CRY with PER, CRY with BMAL-1, and CRY with CLOCK:BMAL-1. The invention also features antibodies generated against CRY, PER, and TIM proteins. These various uses require a source of CRY, TIM, PER, CLOCK, BMAL-1, and CLOCK:BMAL-1.

Circadian proteins can be isolated and purified from a natural source. Alternatively, the proteins can be produced recombinantly or chemically synthesized by conventional methods. Typically the proteins will be produced recombinantly. The nucleotide and amino acid sequences of the circadian proteins are publicly available to one skilled in the art, e.g., mouse CRY1 (Genbank accession # AB000777), mouse CRY2 (Genbank Accession # AB003433), mouse TIM (Genbank accession # AF071506), mouse PER3 (Genbank accession # AF050182), CLOCK (Genbank accesssion # AF000998) and BMAL-1 (Genbank accession # AB015203).

Methods of generating a recombinant circadian protein or a recombinant circadian fusion protein, e.g., CLOCK:GST, are well known in the art. For example, the circadian proteins can be generated by cloning the nucleic acid sequence encoding a circadian protein into an expression vector, where it is operably linked to one or more regulatory sequences. The need for, and identity of, regulatory sequences will vary according to the type of cell in which the circadian protein sequence is to be expressed. Examples of regulatory sequences include transcriptional promoters, enhancers, suitable mRNA ribosomal binding sites, and sequences that terminate transcription and translation. Suitable regulatory sequences can be selected by one of ordinary skill in the art. Standard methods can be used by the skilled person to construct expression vectors. See, generally, Sambrook et al., 1989, *Cloning—A Laboratory Manual* (2nd Edition), Cold Spring Harbor Press.

Vectors useful in this invention include plasmid vectors and viral vectors. Viral vectors can be those derived from, for example, retroviruses, adenovirus, adeno-associated virus, SV40 virus, pox viruses, or herpes viruses. Once introduced into a host cell (e.g., bacterial cell, yeast cell, insect cell, or mammalian cell), the vector can remain episomal, or be incorporated into the genome of the host cell.

In bacterial systems, a number of expression vectors may be advantageously selected depending upon the use intended for the gene product being expressed. For example, when a large quantity of such a protein is to be produced, e.g., for studying the interaction of a CRY protein with other proteins or for raising antibodies to the protein, a vector capable of directing the expression of high levels of a fusion protein (e.g., a GST fusion protein) that is readily purified may be desirable. Alternatively, in mammalian host cells, a number of viral-based expression systems can be utilized.

Construction of GST Fusion Proteins

In certain screening assays (see below) it may be desirable to immobilize the circadian protein. One method of immobilizing a circadian protein is to express the protein as a fusion protein with GST. To do this a chimeric gene encoding a GST fusion protein can be constructed by fusing DNA encoding a circadian protein to the DNA encoding the carboxyl terminus of GST (see e.g., Smith et al., *Gene* 67:31, 1988). The fusion construct can be transformed into a suitable expression system, e.g., *E. coli* XA90 in which expression of the GST fusion protein can be induced with isopropyl-β-D-thiogalactopyranoside (IPTG).

Purification of GST Fusion Proteins

After transformation of the construct into a suitable expression system, induction with IPTG should yield the fusion protein as a major constituent of soluble, cellular proteins. The fusion proteins can be purified by methods known to those skilled in the art, including purification by glutathione affinity chromatography. The purity of the product can be assayed by methods known to those skilled in the art, e.g., gel electrophoresis.

Binding of Circadian Proteins to Immobilized GST

GST fusion proteins can be complexed to glutathione which is attached to a matrix material, e.g., glutathione Sepharose, by methods known to those skilled in the art.

Antibodies

Antibodies which specifically bind to mouse or human CRY, mouse or human TIM, or mouse or human PER, or mouse or human BMAL-1 are also included in the invention. An antibody that specifically binds a mouse or human CRY, PER, TIM, or BMAL-1 is an antibody that binds only to mouse or human CRY, PER, TIM or BMAL-1 and does not bind to (i) other molecules in a biological sample or (ii) CRY, PER, TIM or BMAL-1 of another organism (e.g., Drosophila or yeast).

Antibodies against mouse or human CRY, PER, TIM or BMAL-1 can be used, for example, to inhibit the interaction between these circadian proteins. Anti-CRY, -TIM or PER antibodies (e.g., monoclonal antibodies) can also be used to isolate a CRY, TIM or -PER protein using techniques well known in the art, such as affinity chromatography or immunoprecipitation. The antibodies are also useful in the screening assays described below. Compounds bound to the immunopreceipitated protein can then be identified.

Antibodies specific for mouse CRY, TIM, PER or BMAL-1 can be raised by immunizing a suitable subject (e.g., rabbit, goat, mouse or other mammal) with an immunogenic preparation which contains the mouse or human CRY, TIM, PER or BMAL-1 protein. An appropriate immunogenic preparation can contain, for example, a recombinantly expressed or chemically synthesized CRY, or an immunogenic fragment thereof. The preparation can further include an adjuvant, such as Freund's complete or incomplete adjuvant, or similar immunostimulatory agent. Immunization of a suitable subject with an immunogenic CRY, TIM, PER or BMAL-1 preparation induces a polyclonal anti-CRY, TIM, PER or BMAL-1 antibody response.

The term antibody refers to immunoglobulin molecules and immunologically active portions of immunoglobulin molecules. Examples of immunologically active portions of immunoglobulin molecules include F(ab) and F(ab')$_2$ fragments, which can be generated by treating the antibody with an enzyme such as pepsin. The term monoclonal antibody or monoclonal antibody composition refers to a population of antibody molecules that contain only one species of an antigen binding site capable of immunoreacting with a particular epitope of the polypeptide. A monoclonal antibody composition thus typically displays a single binding affinity for the CRY, TIM or PER with which it immunoreacts.

Polyclonal anti-CRY, -TIM or -PER antibodies can be prepared by immunizing a suitable subject with a mouse CRY, TIM or PER immunogen. The anti-CRY, -TIM or -PER antibody titer in the immunized subject can be monitored over time by well known techniques, such as with an enzyme linked immunosorbent assay (ELISA) using immobilized polypeptide. If desired, the antibody molecules directed against CRY, TIM, PER or BMAL-1 can be isolated from the mammal (e.g., from the blood) and further purified by well-known techniques, such as protein A chromatography, to obtain the IgG fraction.

Monoclonal antibodies can be generated by immunizing a subject with an immunogenic preparation containing a CRY, TIM, PER or BMAL-1. At an appropriate time after immunization, e.g., when the anti-CRY, -TIM, -PER or BMAL-1 antibody titers are highest, antibody-producing cells are obtained from the subject and used to prepare monoclonal antibodies by techniques well known in the art, such as the hybridoma technique originally described by Kohler et al., *Nature* 256:495–497, 1975, the human B cell hybridoma technique (Kozbor et al., *Immunol Today* 4:72, 1983), the EBV-hybridoma technique (Cole et al., *Monoclonal Antibodies and Cancer Therapy*, Alan R. Liss, Inc., pp. 77–96) or trioma techniques. The technology for producing monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a CRY, TIM, PER or BMAL-1, immunogen as described above, and the culture supernatant of the resulting hybridoma cells that screened to identify a hybridoma producing a monoclonal antibody that binds the CRY, TIM, PER or BMAL-1.

The anti-CRY, -TIM, -PER or BMAL-1 antibody may be coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material is luminol; examples of bioluminescent materials include luciferase, luciferin, and aequorin; and-examples of suitable radioactive materials include $^{125}$I, $^{131}$I, $^{35}$S and $^{3}$H.

Screening Assays

The invention encompasses methods for identifying compounds that bind to CRY; disrupt the association of TIM:CRY, CRY:CRY, CRY:PER, CRY:BMAL-1, and CRY:CLOCK:BMAL-1; inhibit or activate the transcription of Per2; or positively regulate the transcription of Bmal-1. Candidate compounds that can be screened in accordance with the invention include polypeptides, oligopeptides, antibodies, and monomeric organic compounds, i.e., "small molecules."

Identification of a Compound that Binds to CRY

A useful first step to identifying a compound which disrupts the association between different circadian proteins (e.g., TIM:CRY, CRY:CRY, CRY:PER, CRY:BMAL-1, and CRY:CLOCK:BMAL-1) is to identify a compound that binds to CRY or another circadian protein. Once a circadian binding compound is identified, the ability of the compound to disrupt the association of different circadian proteins can be assayed. Below are a number of assays which can be used to identify a compound which binds to a CRY protein, e.g., CRY1 or CRY2. The examples are not meant to be limiting and the assays can be performed with other circadian proteins, e.g., TIM, PER, CLOCK and BMAL-1.

Methods of identifying a compound which binds a protein of interest are well known in the art. In one screening method, test compounds are evaluated for their ability to bind CRY, e.g., CRY1 or CRY2. Control reactions which do not contain the compound can be performed in parallel. The method includes immobilizing CRY using methods known in the art such as binding a GST-CRY to a polymeric bead containing glutathione or binding a CRY protein to an anti-CRY antibody which is attached to a solid support. The immobilized CRY is incubated with a test compound for a period of time that permits binding of the test compound to CRY. Following the incubation period, unbound test compound is removed and bound test compound detected. For example, a detectable moiety such as a radionuclide or a fluorescent label can be attached to the compound for ease of detection. Examples of radionuclide and fluorescent labels include $^{125}$I, $^{131}$I, $^{35}$S, $^{3}$H, umbelliferone, fluorescein, fluorescein isothiocyanate, and rhodamine.

Alternatively, the screening method can involve incubating a labeled test compound, with an epitope-tagged CRY protein. Following incubation, the ability of the test compound to bind to the CRY protein is determined using immunoprecipitation with an antibody directed against the epitope tag (e.g., Flag or myc). The recovery of a labeled test compound, e.g., a radioactive compound, following immunoprecipitation indicates that the test compound binds to the CRY protein.

Display libraries can also be used to identify compounds which bind to a CRY protein. In this approach, the test peptides are displayed on the surface of a cell or viral particle, and the ability of particular cells or viral particles to bind an appropriate CRY protein, e.g., CRY1 or CRY2, via the displayed product can be detected in a "panning assay" (Ladner et al., WO 88/06630).

Identifying Compounds which Disrupt the Interaction of CRY:TIM, CRY:CRY. CRY:PER, CRY:BMAL-1 and CRY:CLOCK:BMAL-1

The two-hybrid expression system can be used to screen for compounds capable of disrupting CRY:TIM, CRY:CRY, CRY:PER, CRY:BMAL-1, or CRY:CLOCK:BMAL-1 associations in vivo. In this system, a GAL4 binding site, linked to a reporter gene such as lacZ, is contacted in the presence and absence of a test compound with a GAL4 binding domain linked to a circadian protein, e.g., CRY, TIM, PER, CLOCK or BMAL-1 and a GAL4 transactivation domain linked to a circadian protein, e.g., CRY, TIM, PER, CLOCK, or BMAL-1. Expression of the reporter gene is monitored and a decrease in said expression is an indication that the test compound inhibits the interaction of CRY with TIM, CRY with CRY, CRY with PER, CRY with BMAL-1, or CRY with CLOCK:BMAL-1.

Another method of identifying compounds which disrupt an association between circadian proteins involves the determination of whether the test compounds can disrupt the ability of, e.g., CRY:PER, to block CLOCK:BMAL-1-mediated transcriptional activation. In this system, an E-box sequence linked to a reporter gene such as a luciferase gene is contacted with a CLOCK:BMAL-1 heterodimer. Binding of the CLOCK:BAML-1 heterodimer to the E-box results in expression of the reporter gene. The system is then contacted with a test compound and a circadian protein (e.g., a CRY protein or a circadian protein complex, e.g., CRY:PER), and expression of the reporter gene is monitored. Since CRY and PER block CLOCK:BMAL-1-mediated transcription, an increase in expression of the reporter gene in the presence of the test compound as compared to the expression in the absence of the compound indicates that the compound disrupts the ability of CRY and PER to block CLOCK:BMAL-1-mediated transcription. The transcription assay can be preformed in any cell that expresses the necessary proteins, either naturally or recombinantly, e.g., NIH 3T3 cells, COS-7 cells, or clock neuron cells.

In yet another screening method, one of the components of the CRY:TIM, CRY:CRY, CRY:PER, CRY:BMAL-1, or CRY:CLOCK:BMAL-1 binding complex is immobilized. The circadian protein can be immobilized using methods known in the art, such as adsorption onto a plastic microtiter plate or specific binding of a GST-fusion protein to a polymeric bead containing glutathione. For example, to determine a compound which binds CRY:PER, a GST-CRY can be bound to glutathione-Sepharose beads. The immobilized CRY is then contacted with a labeled circadian protein to which it binds (PER in this case) in the presence and absence of a test compound. Unbound PER can then be removed and the complex solubilized and analyzed to determine the amount of bound labeled PER. A decrease in binding is an indication that the test compound inhibits the interaction of CRY with PER.

A variation of the above-described screening method involves screening for test compounds which are capable of disrupting a previously-formed CRY:TIM, CRY:CRY, CRY:PER, CRY:BMAL-1, or CRY:CLOCK:BMAL-1 interaction. For example, a complex comprising CRY:PER is immobilized as described above and contacted with a test compound. The disassociation of the complex by the test compound correlates with the ability of the test compound to disrupt or inhibit the interaction of CRY with PER.

Identifying Compounds that Activate Transcription of PER2

A screening method used to identify a compound that activates or inhibits the transcription of Per2 includes providing a cell that includes a Per2 regulatory sequence operatively linked to a reporter gene. The Per2 regulatory sequence is preferably mammalian, e.g., mouse PER2 (SEQ ID NO:3; see FIG. 8). In one example, the mouse Per2 regulatory sequence is operably linked to a reporter gene such as a luciferase, a chloramphenicol acetyl transferase, a beta-galactosidase, an alkaline phosphate, or a fluorescent protein gene. A test compound is then contacted with the cell and expression of the reporter gene monitored. An increase in expression of the reporter gene in the presence of the test compound as compared to the expression in the absence of the compound indicates that the compound activates Per2 transcription. Alternatively, a decrease in expression of the reporter gene in the presence of the test compound as compared to expression in the absence of the test compound indicates that the compound inhibits Per2 transcription. The transcription assay can be preformed in any cell which undergoes a circadian rhythm, e.g., NIH 3T3 cells, COS-7 cells, or clock neuron cells.

Identifying Compounds that Positively Regulate Expression of BMAL-1

A screening method that uses a non-human transgenic animal whose somatic and germ cells comprise a disrupted Per2 gene can be used to identify a compound that regulates expression of Bmal-1. The method includes administering a test compound to the transgenic mouse and detecting Bmal-1 expression. An increase in expression of Bmal-1, compared to a control non-human transgenic animal, indicates that the compound positively regulates expression of Bmal-1. Expression of Bmal-1 can be detected using any appropriate method, e.g., detecting Bmal-1 mRNA levels using Northern blot analysis or BMAL-1 protein levels using a BMAL-1 specific antibody or an activity assay.

The transgenic non-human animal used in the method described above includes a non-human animal that contains a disruption in the Per2 gene that is sufficient to inhibit the ability of PER2 to positively regulate Bmal-1. A transgenic non-human animal is preferably a mammal such as a rat or mouse, in which one or more of the cells of the animal include a disruption in the Per2 gene. Other examples of transgenic animals include non-human primates, sheep, dogs, cows, goats, chickens, amphibians, and the like. The transgenic non-human animal is one in which the Per2 gene has been altered, e.g., by homologous recombination between the endogenous gene and an exogenous DNA molecule introduced into a cell of the animal, e.g., an embryonic cell of the animal, prior to development of the animal. Appropriate PER2 transgenic animals which can be used in the method described above are known in the art, e.g., the homozygous mPer2$^{brdm1}$ described by Zheng et al. (Nature, 400:1667 (1999)) the contents of which are incorporated herein by reference.

Modulating the Circadian Clock

Based on the discoveries described herein, it is apparent that expression of Bmal-1 is critical for restarting the circadian loop. The importance of Bmal-1 mRNA rhythm is to drive a Bmal-1 rhythm after a four to six hour delay in the circadian loop. The expression of Bmal-1 makes BMAL-1 available to heterodimerize with CLOCK to drive transcription of circadian proteins, such as Per or Cry. The transcription of Per or Cry restarts the cycle. Therefore, a method of modulating a circadian-clock controlled rhythm includes, for example, altering the endogenous expression of Bmal-1. In one example, an effective amount of a ribozyme, or an oligouncleotide antisense to Bmal-1, can be introduced into a SCN in vivo, thereby inhibiting expression of Bmal-1 in the cell and modulating circadian-clock rhythms.

Antisense Bmal-1 nucleic acid molecules include molecules which are complementary to a sense nucleic acid encoding a BMAL-1 protein, e.g., complementary to the coding strand of a double-stranded cDNA molecule or complementary to a mRNA sequence. Accordingly, an antisense nucleic acid can hydrogen bond to a sense nucleic acid. Antisense Bmal-1 nucleic acids can be designed according to the rules of Watson and Crick base pairing. The antisense nucleic acid molecule can be complementary to full length Bmal-1 mRNA, but more preferably is an oligonucleotide that is antisense to only a portion of the Bmal-1 mRNA, e.g., part or all of the transcription start site, and/or part or all of the coding region. An antisense oligonucleotide can be, for example, about 5, 10, 15, 20, 25, 30, 35, 40, 45 or 50 nucleotides in length.

The Bmal-1 antisense nucleic acid molecules are typically administered to a subject such that they hybridize with or bind to cellular mRNA and/or genomic DNA encoding a protein to thereby inhibit Bmal-1 expression of the protein. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to clock neuron cell surface receptors or antigens. In another example, the antisense nucleic acid molecule is linked to TAT, a HIV leader sequence, that can target the antisense to the SCN (Lisziewicz et al., Hum Gene Ther 11:807–15, 2000).

Alternatively, an expression vector encoding BMAL-1 protein can be introduced into a clock neuron using gene therapy methods. For example, methods of targeting a vector containing a Bmal-1 sequence into an SCN include using a gene therapy vector which includes a tat sequence operably lined to a Bmal-1 nucleic acid sequence. Expression of TAT targets the vector to the SCN.

The gene therapy expression vector can be in the form of a recombinant plasmid, phagemid or attenuated virus in which a mammalian BMAL-1 is operably linked to an appropriate regulatory sequence. Examples of suitable viral vectors include recombinant retroviral vectors (Valerio et al., 1989, Gene, 84:419; Scharfman et al., 1991, Proc. Natl. Acad. Sci., USA, 88:462; Miller, D. G. & Buttimore, C., 1986, Mol. Cell. Biol., 6:2895), recombinant adenoviral vectors (Freidman et al., 1986, Mol. Cell. Biol., 6:3791; Levrero et al., 1991, Gene, 101:195), and recombinant Herpes simplex viral vectors. The regulatory sequence can be the same as the endogenous regulatory sequence, or different. It can be inducible or constitutive. Suitable constitutive regulatory sequences include the regulatory sequence of a housekeeping gene such as the α-actin regulatory sequence, or may be of viral origin such as regulatory sequences derived from mouse mammary tumor virus (MMTV) or cytomegalovirus (CMV).

Utility of the Compounds

Compounds found to disrupt the interaction of CRY:TIM, CRY:CRY, CRY:PER, CRY:BMAL-1, or CRY:CLOCK:BMAL-1 or bind to CRY can be used to manipulate the circadian clock. For example, the association of PER with CRY in the cytoplasm of a clock neuron is necessary for the translocation of PER into the nucleus of the cell. Once PER is in the nucleus, PER has a negative feedback effect on the circadian loop, i.e., inhibits CLOCK:BMAL-1-mediated transcription. A compound which disrupts the ability of CRY and PER to associate in the cytoplasm would prevent the translocation of PER to the nucleus and would therefore be useful for blocking PER's negative feedback effect on the circadian loop. Similarly, a compound that binds to CRY is potentially useful for blocking CRY's negative feedback effect on the circadian loop.

Compounds that can modulate the transcription of the Per2 gene can be used to advance or delay restarting the circadian loop. For example, a compound that inhibits transcription of Per2 will inhibit the transcription of Bmal-1. Since BMAL-1 is needed to restart the circadian loop, a compound that inhibits transcription of Per2 will inhibit the restarting of the circadian loop. Moreover, delivery of an expression vector encoding a mammalian Bmal-1 protein to a clock neuron can also be used to manipulate the circadian rhythm and advance restarting of the circadian loop.

A compound identified as described above is therefore useful as an agent that can reset the circadian clock. The compound can be used to prevent jet lag or facilitate resetting the clock in shift workers. In addition, the compound can be used to improve rhythmicity, i.e., the coordinated regulation of outputs from cells within the SCN. Disruption of rhythmicity is common in the elderly and affects the ability to sleep. The compound described herein can be used to improve the interactions between neurons to allow them to arrive at a common phase or directly reset individual neurons to a common phase. Compounds can also be used to alleviate circadian rhythm disorders such as winter depression or seasonal affective disorder.

Administration

The compounds described herein can be administered to a subject, e.g., a mammal such as a human, to treat a circadian rhythm disorder, e.g., jet lag, winter depression and shift work disturbance. The compounds can be used to specifically advance or delay the phase of certain circadian rhythms. The ability of a compound to reset the clock to a specified phase will depend on the nature of the agent and its biological half-life.

The compound can be administered alone, or in a mixture, in the presence of a pharmaceutically acceptable excipient or carrier (e.g., physiological saline). Given that the different CRY and PER proteins are redundant, it is preferable that the compound administered have the specificity to affect all members of a given family, e.g., CRY1 and CRY2 (CRY protein family members) or PER1, PER2 or PER3 (PER protein family members). Alternatively, a combination of compounds specific for each member of a family can be administered.

Gene therapy vectors can be delivered to a subject by, for example, intravenous injection or local administration (see U.S. Pat. No. 5,328,470). The pharmaceutical preparation of the gene therapy vector will typically include the gene therapy vector in an acceptable carrier.

The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well known reference text in this field, and in the USP/NF (United States Pharmacopeia and the National Formularly). A pharmaceutical composition is formulated to be compatible with its intended route of administration. Examples of routes of administration include oral, rectal, and parenteral, e.g., intravenous, intradermal, and subcutaneous, transdermal (topical), and transmucosal, administration. Compounds which are unable to cross the blood-brain barrier are administered locally to the SCN.

As is well known in the medical arts, dosage for any given patient depends upon many factors, including the patient's size, body surface area, age, the particular compound to be administered, sex, time and route of administration, general health, and other drugs being administered concurrently. Dosages for the compounds of the invention will vary, but determination of optimal dosage is well within the abilities of a pharmacologist of ordinary skill.

Transgenic Animals

Based on the discovery made herein, Tim is predicted to be essential for embryonic development in animals. In order to delineate the region(s) of Tim essential for development, the invention includes non-human transgenic animals that have a selected region of Tim disrupted. The role of this region in embryonic development can be determined by analyzing homozygous embryos for developmental defects, e.g., determining cellular organization in whole embryos that are fixed and embedded in paraffin around embryonic day 7.5.

Transgenic non-human animals that have a Tim disruption are also useful for screening for compounds that ameliorate the developmental defects caused by the disruption of Tim, e.g., a test compound can be administered to a female Tim$^+$/Tim$^-$ heterozygote non-human animal during and/or subsequent to mating with a male Tim$^+$/Tim$^-$ heterozygote of the same species. The ability of the test compound to ameliorate Tim-associated defects occurring during embryonic development can be determined by analyzing Tim$^-$ homozygous embryos for developmental defects, e.g., determining cellular organization in whole embryos that are fixed and embedded in paraffin around embryonic day 7.5.

Transgenic Tim animals which overexpress TIM are also be useful for studying the function and/or activity of a TIM protein in circadian rhythm. For example, transgenic non-human animals are generated where an endogenous Tim regulatory element, e.g., a promoter, is replaced with an exogenous regulatory element such that the exogenous regulatory element drives a higher level of expression of TIM in a cell of the transgenic animal as compared to a non-transgenic animal. The cell is preferably a neuron. The role of TIM in circadian rhythm in the transgenic animal can be determined by analyzing circadian rhythms in locomoter activity, e.g., rhythmic wheel turning.

As used herein, a "transgenic animal" is a non-human animal, the nucleated cells of which include a transgene. The animal is preferably a mammal, e.g., a rodent such as a rat or mouse. Other examples of transgenic animals include non-human primates, sheep, dogs, cows, goats, chickens, rabbits, amphibians, and the like. A transgene is exogenous DNA or a rearrangment, e.g., a deletion of endogenous chromosomal DNA, which is integrated into or occurs in the genome of the animal's cells. A transgene can direct the expression of an encoded gene product in one or more cell types or tissues of the transgenic animal. Other transgenes, e.g., a knockout, reduce expression. Thus, a transgenic animal can be one in which an endogenous Tim gene has been altered, e.g., by homologous recombination between the endogenous gene and an exogenous DNA molecule introduced into a cell of the animal, e.g., an embryonic cell of the animal, prior to development of the animal. The animal can be heterozygous or homozygous for the transgene.

Intronic sequences and polyadenylation signals can also be included in the transgene to increase the efficiency of expression of the transgene. A tissue-specific regulatory sequence(s) can be operably linked to a transgene of the invention to direct expression of a TIM protein in particular cells. A transgenic founder animal can be identified based upon the presence of a TIM transgene in its genome and/or expression of TIM mRNA in tissues or cells of the animals. A transgenic founder animal can then be used to breed additional animals carrying the transgene. Moreover, transgenic animals carrying a transgene encoding a TIM protein can further be bred to other transgenic animals carrying other transgenes.

TIM proteins or polypeptides can be expressed in transgenic animals or plants, e.g., a nucleic acid encoding the protein or polypeptide can be introduced into the genome of an animal. In preferred embodiments, the nucleic acid is placed under the control of a tissue specific promoter, e.g., a milk or egg specific promoter, and recovered from the milk or eggs produced by the animal. Suitable animals are mice, pigs, cows, goats, sheep, and chickens.

The invention also includes a population of cells from a transgenic animal, as discussed herein.

Any technique known in the art may be used to generate the transgene non-human animals discussed herein. For a review, see Gordon, 1989, Transgenic Animals, Intl. Rev. Cytol. 1 15:171–229 and Hogan et al. "Manipulating the Mouse Embryo" (Cold Spring Harbor Press, Cold Spring Harbor, N.Y., 1986.

Experimental Information

EXAMPLE 1 mPER Proteins Interact in Mammalian Cells

The importance of mPER:mPER interactions in the negative limb of the clock feedback loop was examined. Previous studies using the yeast two-hybrid assay showed that all of the mPERs interact with one another and that mPER1 and mPER2 can homodimerize (Zylka et al., *Neuron* 21:1103–1115, 1998). No interactions were detectable between mTIM and any of the mPER proteins in the yeast system. Co-immunoprecipitation experiments were performed in mammalian cells using epitope-tagged proteins expressed in COS7 cells.

Expression plasmids were constructed that contain full-length coding regions for each mPER protein and mTIM with either a hemaglutinin (HA) or a V5 epitope tag at the carboxyl terminus. For cloning, the coding regions of mPER2 (AF035830), mPER3 (AF050182), and mTIM (AF071506) were ligated into pcDNA 3.1 containing either an N terminal or C terminal HA tag. Full-length coding regions were amplified with Pfu TurboJ (Stratagene, La Jolla, Calif.) from plasmid DNA (mPER1). Correct orientation of each construct was verified by sequence analysis. Clones were also transcribed and translated in vitro using TnT T7 QuickJ (Promega, Madison, Wis.) to confirm that a protein of the correct size was produced. Moreover, clones were transiently transfected into NIH3T3 cells and into COS7 cells. Crude cell extracts were prepared, western blotted and probed with anti-V5 or anti-HA antibodies to detect full-length, epitope-tagged proteins.

Once the constructs were generated, COS7 cells were transiently cotransfected with expression plasmids encoding mPER3-HA and either mPER1-V5, mPER2-VS, mPER3-V5, or mTIM-VS. Cell lysates were immunoprecipitated with anti-HA antibody, and the immunoprecipitated material was blotted and probed with anti-V5 antibodies to assess interactions. Briefly, co-immunoprecipitations were performed as described by Lee and colleagues (*Neuron* 21:857–867, 1998) with the following modifications. COS7 cells ($5 \times 10^6$) were seeded in 10 cm dishes and transfected the following day with the expression plasmids described above. Forty-eight hours post transfection, the cells were washed twice with PBS, homogenized in binding buffer (20 mM HEPES, pH 7.5, 100 mM KCl, 2.5 mM EDTA, 5 mM DTT, 2.5 mM PMSF, 0.05% Triton X-100, 10% glycerol, 10 μg/ml leupeptin, 10 μg/ml aprotonin) and clarified by centrifugation. Protein concentrations were-determined by the Bradford method according to the manufacturer's instructions (Pierce, Iselm, N.J.). Total protein (30 μg) from the clarified supernatant was combined with 15 μl of protein A/G agarose beads (Santa Cruz Biotechnology, Santa Cruz, Calif.) and incubated for 1 hr at 4EC to remove non-specific interactions. The samples were centrifuged and the supernatant was incubated for 3 hrs at 4EC with anti-HA mouse monoclonal antibodies (Babco, 1:50 dilution) and 15 μl of protein A/G agarose beads. Subsequently, the beads were washed four times (400 μl binding buffer for 10 min. per wash), mixed with 5 μl of 4×sodium dodecyl sulfate (SDS) gel loading buffer, boiled, and centrifuged. The supernatant was analyzed by SDS-polyacrylamide gel electrophoresis (PAGE) and western blotted as follows. Total protein (5 μg) from COS7 cells was extracted as described above, separated by SDS-PAGE, and transferred to a nitrocellulose membrane using a semi-dry blotting apparatus. Membranes were blocked with 5% non-fat milk. Blots were incubated with either the mouse anti-HA antibody (1:10,000) or the mouse anti-V5 antibody (1:5,000) overnight at 4EC. A goat anti-mouse horseradish peroxidase secondary antibody (1:10,000) was used in combination with enhanced chemiluminescence (NEN) to detect proteins.

Following detection of epitope-tagged proteins with one antibody, the blots were stripped in stripping buffer (62.5 mM Tris-HCl (pH 6.7), 100 mM 2-mercaptoethanol, 2% SDS) at 50EC for 30 minutes. The membrane was washed extensively (20 mM Tris, pH 7.6, 137 mM NaCl, 0.05% Tween-20) then blocked again and processed for detection of the second epitope-tagged protein.

Western blotting of cell lysates prior to immunoprecipitation showed that all four proteins tagged with the V5 epitope were expressed at detectable levels. The co-immunoprecipitation data showed that mPER3 homodimerized and heterodimerized with mPER1 and mPER2, but did not interact at detectable levels with mTIM. When the blot was stripped and re-probed with the anti-HA antibody, similar amounts of mPER3-HA were precipitated in each sample. Thus, the lack of detection of an mPER3:mTIM interaction was not due to a transfection or expression artifact. A similar pattern of interactions was obtained when the coimmunoprecipitation experiments were performed using mPER1-HA in place of mPER3-HA; that is, co-immunoprecipitation of the mPER proteins but not mTIM. These results in mammalian cells confirm the findings in yeast: each mPER can homodimerize with itself or heterodimerize with another mPER but does not detectably interact with mTIM. Our results do not rule out the possibility of biologically relevant mPER:mTIM interactions in the mammalian clockwork. But the data do suggest that such mPER:mTIM interactions must be much weaker than the strong mPER:mPER interactions found in both yeast and mammalian cells.

EXAMPLE 2

Subcellular Location of mPER3 Changes in the Presence of mPER1 or mPER2

To determine whether mPER:mPER interactions may be important for the nuclear translocation of the mPERs and their subsequent negative feedback on transcription, mPER-:mPER interactions were examined by first evaluating the subcellular location of the HA-and V5-epitope tagged constructs when transfected into NIH3T3 and COS7 cells.

Immunofluorescence of epitope-tagged proteins was used to observe protein location within cells. Briefly, cells ($3 \times 10^5$) were seeded on glass coverslips in 6-well dishes and transfected the following day as described above with 1 μg of total DNA per well. Forty-eight hours after transfection, cells adherent to the coverslip were washed twice with phosphate buffered saline (PBS), fixed with -20EC methanol (10 min), washed, and blocked in 5% normal goat serum/ 0.1%Triton X-100 in PBS (1 hr). Mouse anti-V5 IgG (1:500; Invitrogen, Calsbad, Calif.) or rabbit anti-HA IgG (1:200; Santa Cruz Biotechnology, Santa Cruz, Calif.) was applied for 1.5 hrs. Cells were washed and then incubated in the dark (I hr) with secondary antibodies. These consisted of either goat anti-rabbit IgG conjugated to Cy2 (1:200) or goat anti-mouse IgG conjugated to Cy3 (1:200; Jackson ImmunoResearch). Cells were washed, and the nuclei were stained with bisBenzimide and then mounted for fluorescence microscopy. A random population of 30–60 cells from each coverslip was examined by epifluorescence microscopy and the subcellular distributions of the transfected proteins were recorded without knowledge of the treatment. At least three independently transfected coverslips were analysed. The cellular location was scored as one of three categories: both cytoplasm and nucleus, cytoplasm alone, or nucleus alone.

When expressed singly in NIH3T3 cells, mPER1 and mPER2 were each found predominantly in both cytoplasm and nucleus of individual cells (78% and 61% of transfected cells, respectively; n=3 experiments), but were also detected in the nucleus alone (15% and 29%, respectively). In contrast, mPER3 was mostly in cytoplasm alone (95% of transfected cells), and mTIM was mostly nucleus alone (89%).

To determine whether co-expression promotes nuclear entry of the proteins, all possible pairwise combinations of the mPER and mTIM plasmids were co-transfected. mTIM co-expressed with any of the mPER proteins did not affect subcellular location of mTIM or the mPER proteins ($p>0.05$). The most obvious example of this was observed when mPER3 and mTIM were coexpressed: mPER3 remained cytoplasmic, and mTIM remained nuclear. The inability of mTIM to influence subcellular location of the mPER proteins provides further evidence that mTIM does not interact functionally with the mPER proteins in a manner analogous to the interactions of PER and TIM in Drosophila.

When mPER3 was co-expressed with either mPER1 or mPER2, mPER3 was dramatically redistributed from cytoplasm only to both cytoplasm and nucleus ($p<0.01$, n=3 experiments). mPER1 was more effective than mPER2 in promoting nuclear entry of mPER3; that is, nucleus-only location was found in 3 times more cells with mPER1 co-transfections, compared with mPER2. The same redistribution profile was observed when the amounts of the mPER1 and mPER3 plasmids transfected were decreased by 75% (from 500 ng to 125 ng). All of the subcellular localization experiments described above in NIH3T3 cells were also performed in COS7 cells with similar results. Despite trying all possible combinations of mPER proteins with mTIM, including adding all four proteins at once, we were unable to induce a "nucleus-only" location of mPER1 or mPER2 in >30% of NIH3T3 cells. Thus, it would appear that the tested combinations do not completely reconstitute mPER function in NIH3T3 cells. This suggested that there are other clockrelevant factors important for the nuclear translocation of the mPER proteins.

EXAMPLE 3 mPER:mPER Interactions do not Augment Inhibition of CLOCK:BMAL-1-Induced Transcription The ability of mPER1/2:mPER3 interactions to promote the nuclear entry of mPER3 and augment the inhibition of CLOCK:BMAL1-induced transcription was examined. For these studies, a luciferase reporter gene assay in NIH3T3 cells was used. The reporter construct utilizes a 200 bp fragment of the promoter region of the mouse arginine vasopressin (prepropressophysin) gene containing a CACGTG E box, as previously described (Jin et al., Cell 96:57–68, 1999). This reporter gene construct is activated by CLOCK and BMAL1 acting together on the E box enhancer (Jin et al., supra). Briefly, luciferase reporter gene assays were performed in NIH3T3 cells as previously described (Gekakis et al., Science 280:1564–1569, 1998; Jin et al., supra). Cells ($3\times10^5$) were seeded in six-well plates and transfected the following day. Each construct contained the vasopressin promoter (10 ng) or 1.8 kb of the 5' flanking region of the mPer1 gene and each cloned into pGL3 BasicJ (Promega, Madison, Wis.) (10 ng of each reporter) and CMV βgalactosidase (25 ng). cDNAs encoding Mouse CLOCK, hamster BMAL-1 and human MOP4, each subcloned into pcDNA3. 1-V5, were each used at 250 ng per transfection. Amounts of the mPER and mTIM constructs transfected varied depending on the experiment. The total amount of DNA per well was adjusted to 1 µg by adding pcDNA 3.1 vector as carrier. Forty-eight hours after transfection, cells were harvested to determine β-galactosidase activity and luciferase activity by luminometry.

Figure 1:
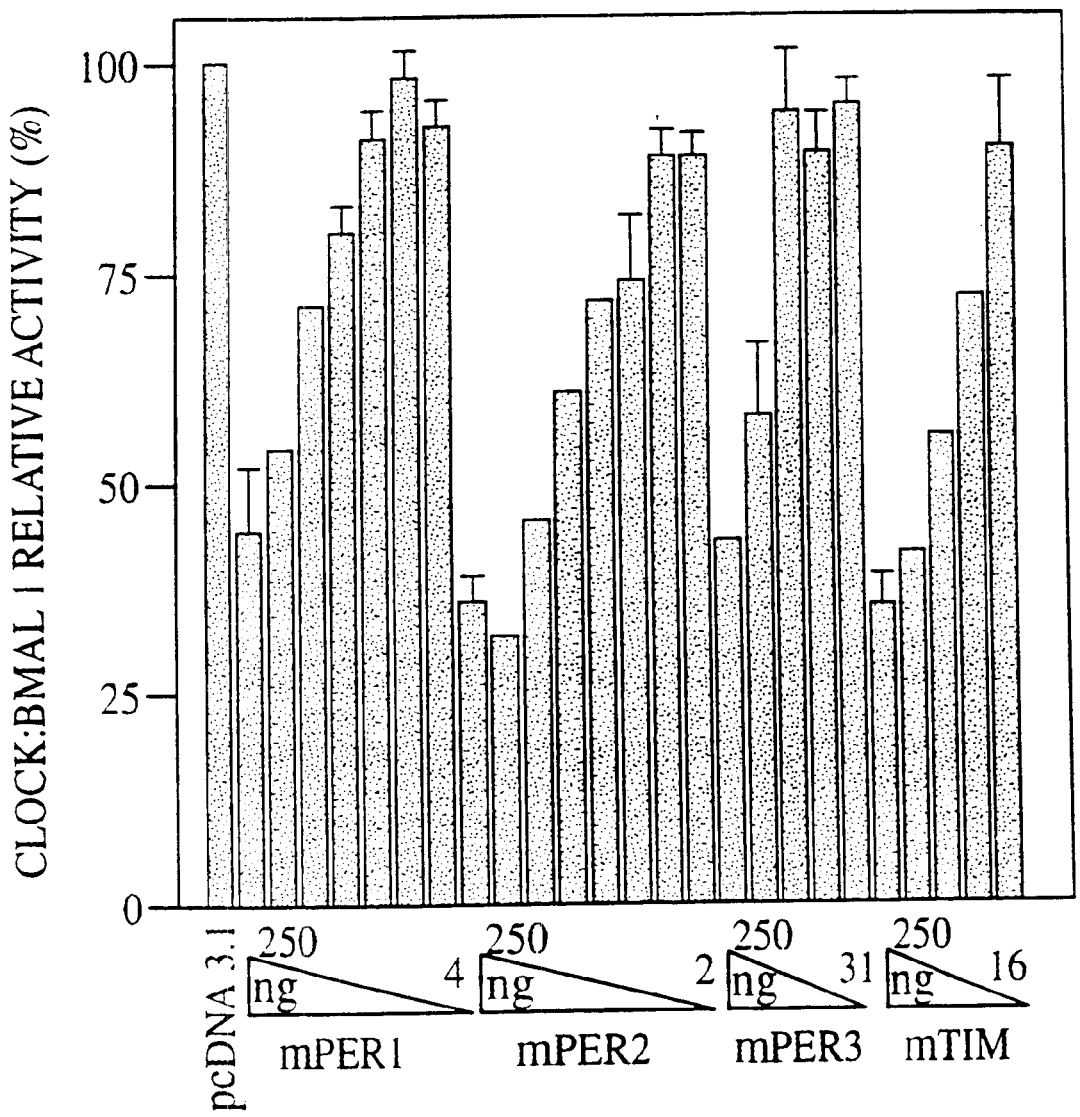
FIG. 1 is a histogram showing dose-response studies on inhibition of CLOCK:BMAL-1-induced transcription by the mPER and mTIM proteins.

Dose-response studies of inhibition of CLOCK:BMAL-1-induced transcription by the mPER proteins and mTIM are shown in FIG. 1. Data from 16 transcription assays were combined by normalizing the relative luciferase activity values in each experiment to the activity from CLOCK:BMAL-1 alone (set at 100%). The amounts of the mPER or mTIM expression constructs transfected are listed (in ng) at the extremes of the triangles. Individual experiments were done in duplicate or triplicate. Values are plotted as the mean %+SEM when three or more experiments were performed with a given amount of expression construct. All other values represent averages from two experiments. Results showed that CLOCK:BMAL-1-induced transcription was maximally inhibited transfection of 250 ng of each of the mPer and mTim constructs. Maximal inhibition reached 55–70% for each construct and was not substantially augmented by any pairwise transfection of the mPer and mTim constructs (at 250 ng each). As the amount of each expression plasmid transfected was decreased, there was decreasing inhibition of CLOCK:BMAL-1 transcription (FIG. 1). From the dose-response curves, the amount of each expression construct that was at the threshold of causing transcriptional inhibition was identified.

Using threshold amounts of each expression construct, all possible pairwise mPER:mPER and mPER:mTIM combinations were next examined to look for synergistic or additive interactions. In no instance, however, was there observed a consistent augmentation of transcriptional inhibition with low-dose, pairwise combinations of mPER expression constructs or mPER plus mTIM expression constructs (n=4 experiments). Co-expression experiments with low doses of mPER1 and mPER3 did show a consistent trend toward inhibition of CLOCK:BMAL-1-induced transcription, but the effects were significant ($p<0.05$) in only one of three experiments.

The data hint that mPER1:mPER3 heterodimers may be functionally relevant for transcriptional inhibition. The endogenous expression of the mPer1, mPER2, mPer3, and mTim genes in NIH3T3 cells may obscure finding a more robust inhibitory effect on transcription. Based on the modest effects of mPER:mPER interactions on nuclear localization and transcriptional inhibition, however, it seemed more likely that there were other factors necessary for nuclear translocation and/or retention of the mPER proteins and for their subsequent inhibition of CLOCK:BMAL-1-induced transcription.

EXAMPLE 4 mCry1 and mCry2 RNA Levels in the SCN and in Peripheral Clocks are Regulated by CLOCK It was next determined if cryptochromes were involved in the CLOCK:BMAL-1-driven mPer feedback loop. mCry1 and mCry2 gene expression in wild-type and homozygous Clock mutant mice was examined, because a decrease in gene expression in Clock/Clock mice (i.e., mice homozygous for the mutation) would place the cryptochrome genes within the CLOCK-driven feedback loop.

Northern analysis was used to examine gene expression of CRY1 and CRY2. Briefly, total RNA was extracted from tissues using the Ultraspec RNA isolation reagent. Polyadenylated (polyA+) RNA was prepared using oligotex poly dT spin columns (Qiagen, Valencia, Calif.). PolyA+ RNA was separated by electrophoresis through a 1% agarose-formaldehyde gel, blotted onto GenScreenJ (New England Nuclear), and hybridized with random prime-labeled probe (S.A.=$2\times10^6$ cpm/ml). The blots were hybridized with Express HybridizationJ Solution (Clontech, Palo Alto, Calif.) and washed following the manufacturer's protocol. Probes used were mCry1 (nt 1081–1793 of Act. No. AB000777) and mCry2 (nt 1060–1664 of Act. No. AB003433). Probe for actin was from human B-actin, purchased from Clontech (Palo Alto, Calif.). Blots were exposed at −80EC to film with 2 intensifying screens.

Figure 2A:
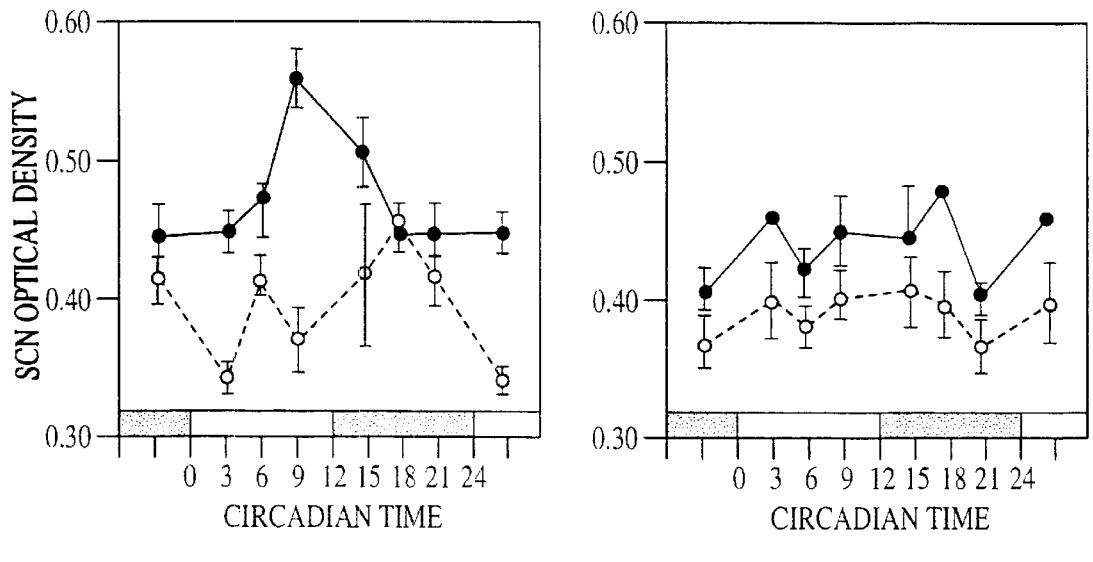
FIGS. 2A–B are line graphs showing mouse Cry1 and Cry2 mRNA levels in SCN (FIG. 2A) and mouse Cry1 and Cry2 RNA levels in skeletal muscle (FIG. 2B).

Four blots were prepared from the RNA samples, with each blot consisting of the eight time-points from one genotype and a standard lane. One microgram of polyA +RNA was loaded per lane for each genotype. Each blot was probed, stripped, then reprobed to detect mCry1, mCry2, and actin. To calculate relative RNA abundance, optical densities of mCry1 and mCry2 hybridization were divided by densities from actin hybridization to the same blot. Normalized values were then averaged for the two replicate blots prepared from a single set of RNA samples. Comparison across blots probed and exposed under similar conditions suggested that the absolute level of expression of the mCry genes was lower in Clock/Clock mice than in wild-type mice. This difference in absolute expression level was confirmed using two additional blots that included selected (peak-trough) RNA samples from the two genotypes side-by-side, and were probed for both mCry1, mCry2, and actin.

mCry RNA levels in SCN are depicted in FIG. 2A. Panels depict the temporal profiles of mCry1 RNA levels (left) and mCry2 RNA levels (right) in the SCN of wild-type mice (solid lines) and Clock/Clock mice (dashed lines). Each values is the mean±SEM of 4 animals. The horizontal bar at the bottom of the panels represents lighting cycle prior to placement in DD; the stippled areas represent subjective day; and the filled areas represent subjective night. Photomicrographs showed representative autoradiographs of mCry1 and mCry2 gene expression from coronal brain sections (15 $\mu$m) at the level of the SCN from wild-type (+/+) and Clock/Clock (CZk/CZk) mice at CT 9. The brain sections were examined by in situ hybridization using cRNA probes as follows. A breeding colony of mice carrying the Clock mutation was established on a BALB/c background. For studies, both males and female mice 5–15 weeks of 24 age were used. Mice were housed in LD, except as noted. Animals were killed by decapitation. Genotypes were determined using a PCR mutagenesis method, as previously described (Jin et al., supra).

Antisense and sense cRNA probes were generated from each plasmid by in vitro transcription in the presence of $^{35}$S-UTP (1200 Ci/mmol). Probe for mCry1 (AB000777) was nucleotides 1081-1 793 and for mCry2 (AB003433) was nucleotides 1060–1664. Probe quality and size was confirmed by determining $^{35}$S incorporation into TCA-precipitable material, and by gel electrophoresis and subsequent autoradiography of the gel.

Prehybridization, hybridization, and wash procedures were performed as described by Weaver. Probe (50 $\mu$l at 107 cpm/ml) was applied to each slide. Coverslipped slides were then incubated in humidified chambers overnight at 55E C. Following completion of the wash steps, slides were air dried and exposed to Kodak BioMax MR film for 8 days.

Densitometric analysis of hybridization intensity was accomplished using NIH Image software on a Macintosh computer; data are expressed as absolute optical density values as determined by calibration with Kodak photographic step tablet #3. $^{14}$C standards included in each cassette were used to verify that the optical density values measured were within the linear response range of the film.

Figure 2B:
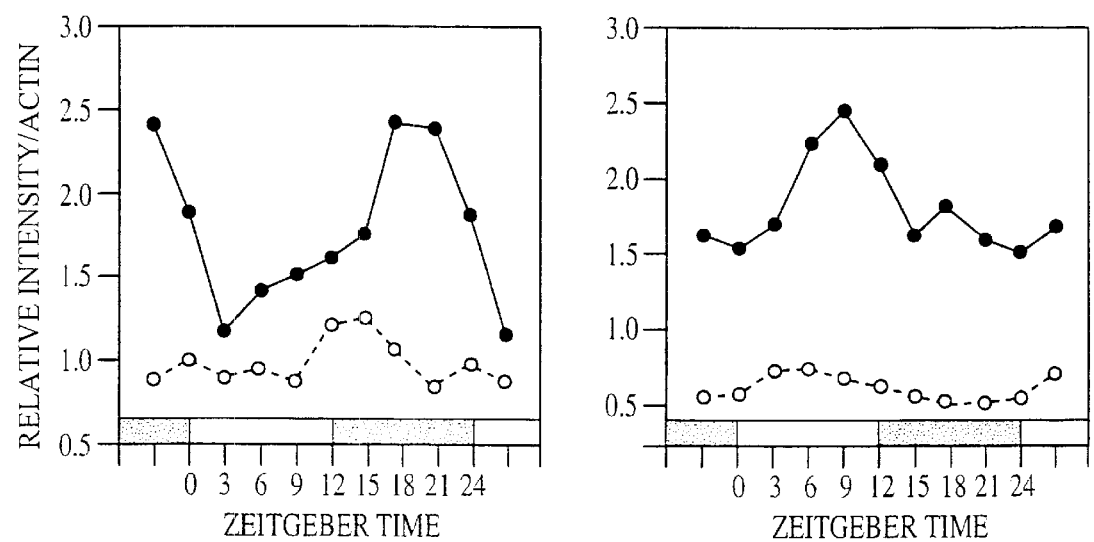

The results showed that mCry1 RNA levels exhibited a prominent circadian rhythm in the SCN of wild-type animals (ANOVA, $p<0.05$; FIG. 2A). The phase of the mCry1 RNA rhythm was most similar to the phase of the mPER2 RNA oscillation in the SCN. In sharp contrast to wild-type mice, no mCry1 RNA rhythm was apparent in the SCN of Clock/Clock mice (ANOVA, $p>0.05$; FIG. 2A). Thus, the mCry1 RNA rhythm is dependent on a functional CLOCK protein. These results are similar to the finding that the amplitude of RNA rhythms for each of the three mPer genes is markedly reduced in Clock/Clock mice (Jin et al., supra).

mCry2 RNA levels in the SCN of wild-type animals did not show a circadian rhythm (FIG. 2A; $p>0.05$). Interestingly, mean steady-state mCry2 RNA levels were nonetheless significantly lower in Clock/Clock mice, compared to those in wildtype controls (ANOVA, $p<0.005$). This finding suggests that mCry2 transcription is also at least partially dependent on a functional CLOCK protein. It is worth noting that of 5 genes studied whose RNA levels do not manifest a circadian rhythmn in the SCN, mCry2 is the only one in which mRNA levels in Clock/Clock animals were observed (see Jin et al., supra). Since circadian clocks also appear to exist in peripheral tissues (Balsalobre et al., *Cell* 93:929–937, 1998; Zylka et al., *Neuron* 20:1110, 1998b; Sakamoto et al., *J. Biol. Chem.* 273:27039–27042, 1998), the temporal profiles of mCry1 and mCry2 RNA levels in skeletal muscle were examined. This tissue was chosen because the three mPer genes manifest robust RNA rhythms there (Zylka et al., 1998b, supra). mCry RNA levels in skeletal muscle are shown in FIG. 2B. Autoradiograms (upper panels) illustrate Northern blots of mCry1 (3.0 kb transcript, left) and mCry2 (4.4 kb transcript, right) RNA levels at each of 8 time points in 12L:12D, with lights on from Zeitgeber Times (ZT) 0–12. The lower panels depict quantitative assessment of mCry1 and mCry2 RNA levels in skeletal muscle of wildtype (solid lines) and Clock/Clock mice (dashed lines). The values are the average relative intensity of two replicate blots with each probe. Data were normalized and expressed relative to hybridization intensity of actin control probe. Data at ZT 21, ZT0/24, and ZT3 are double plotted. In contrast to the situation in the SCN, both mCry1 and mCry2 RNA levels in muscle exhibited a daily rhythm under 12 hrs light: 12 hrs dark (LD) (FIG. 2A) and a circadian rhythm under constant darkness. The peak of the mCry2 rhythm preceded that of mCry1 by 6 to 9 hrs, and the mCry1 RNA rhythm was delayed by several hrs relative to the phase of its RNA rhythm in the SCN. A phase delay between the SCN and peripheral oscillations is also observed in the RNA rhythms of the three mPer genes (Zylka et al., 1998b, supra). In skeletal muscle of Clock/Clock animals, the mCry1 RNA rhythm was dampened and phase advanced, while the mCry2 RNA rhythm was abolished (FIG. 2B). For both genes, RNA levels were lower in Clock/Clock animals at all times, compared to wild-type controls.

Taken together, these data indicate that the transcriptional regulation of mCry1 and mCry2 is under CLOCK control in both the SCN and in peripheral clocks. These findings provide strong evidence that the mouse cryptochromes are components of the CLOCK: BMAL-1-driven feedback loop. Moreover, the occurrence of a CACGTG E box 300 bp upstream of the mCry1 transcription start site suggests that CLOCK directly participates in rhythmic mCry1 transcription through an E box enhancer in its promoter.

EXAMPLE 5 mCRY1 and mCRY2 Block CLOCK:BMAL-1-induced Transcription in NIH3T3 Cells

The involvment of mammalian cryptochrome within the negative limb of the feedback loop was analyzed by determining whether mCRY1 and/or mCRY2 can inhibit CLOCK: BMAL-1-induced transcription. For this phase of study, 14 luciferase reporter gene studies were performed in NIH3T3 cells using either the vasopressin promoter (Jin et al., supra) or 1.8 kb of the 5' flanking region of the mPer1 gene subcloned into a promoterless luciferase reporter vector.

Figure 3A:
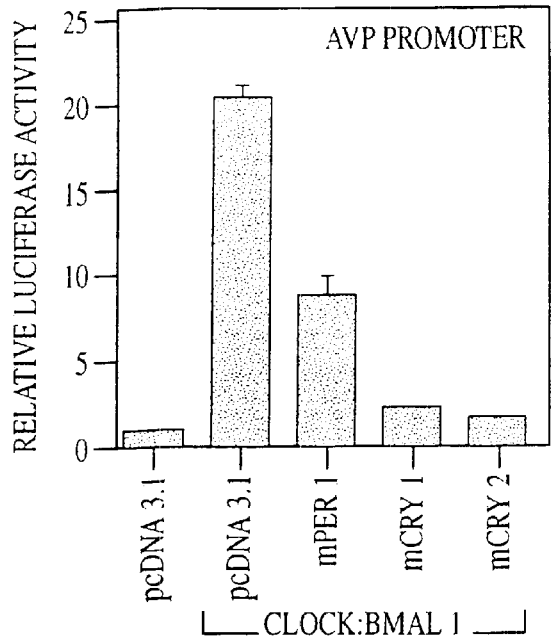
FIGS. 3A–D is a histogram showing inhibition of CLOCK:BMAL1-mediated transcription from the vasopressin (AVP) promoter (FIGS. 3A, 3C–D) or mPer1 promoter (FIG. 3B) by mPER1, mCRY1 and mCRY2 (250 ng each).
Figure 3B:
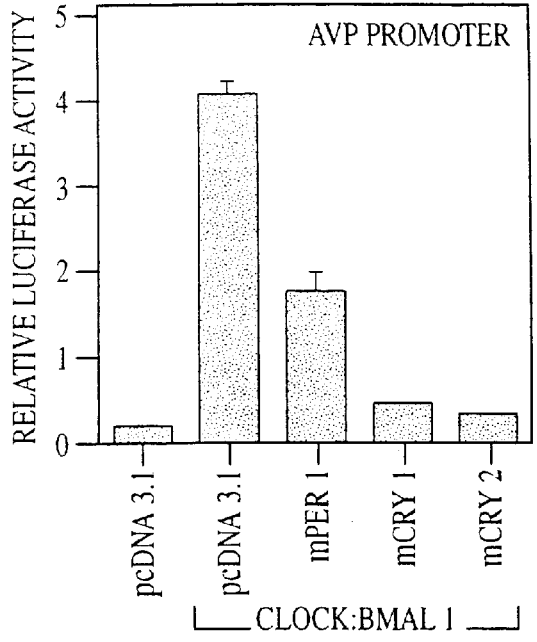
Figure 3C:
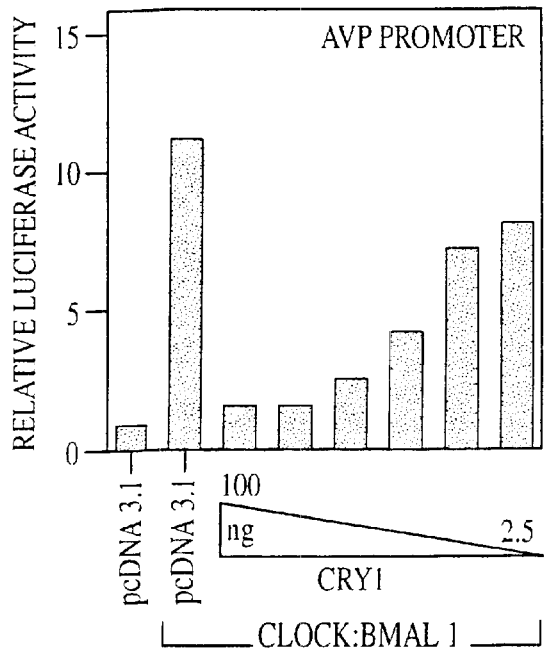
Figure 3D:
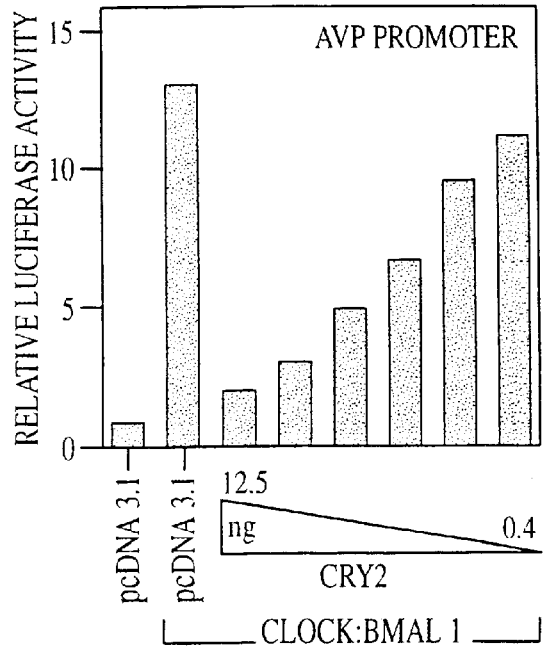

Inhibition of CLOCK:BMAL-1-mediated transcription from the vasopressin (AVP) promoter (FIG. 3A) or mPer1 promoter (FIG. 4B) by mPER1, mCRY1 and mCRY2 (250 ng each) was determined. Each value is the mean±SEM of three replicates from a single assay. The results are representative of three independent experiments. Dose-response curves for mCRY1 (FIG. 3D) or mCRY2 (FIG. 3D) inhibition of CLOCK:BMAL-1-mediated transcription from the vasopressin (AVP) promoter. Each value is the mean±SEM of three replicates from a single assay. Similar results were found in replicate experiments.

Results show that when vasopressin and mPer1 promoters were used in the reporter vectors, mPER1 caused a maximal inhibition of 61% and 30%, respectively. mCRY1 and mCRY2, on the other hand, inhibited CLOCK:BMAL-1-induced transcription by >90% from either reporter. This dramatic effect on transcriptional inhibition was dose dependent for each of the two mCRY proteins. These results indicate that mCRY1 and mCRY2 are each potent inhibitors of CLOCK:BMAL-1-mediated transcription. The mCRY-induced transcriptional inhibition must occur through direct or indirect interaction with the CLOCK: BMAL-1:E box complex because this is the only complex common to both the vasopressin and mPer1 promoters

EXAMPLE 6

Both mCRY1 and mCRY2 are Nuclear Proteins

For the mCRY proteins to interact with the CLOCK:BMAL-1:E box complex, they must be present in the nucleus. Previous studies have shown that mCRY2 is indeed a nuclear antigen (Kobayashi et al., *Nucleic Acids Res.* 26:5086–5092, 1998; Thresher et al., *Science* 282:1490–1494, 1998). The situation with mCRY1 is ambiguous because previous studies of the endogenous protein and green fluorescent protein (GFP)-tagged mCRY1 fragments indicate localization mainly in mitochondria (Kobayashi et al., supra). To determine the localization of CRY1 or CRY2, the CRY proteins were tagged at the ends of the protein with a number of different epitopes. For example, the coding regions of mCRY1 (AB000777) were ligated into the pcDNA 3.1 V5-His expression vector containing either an N terminal or C terminal HA tag. For mCRY2, the nucleotide sequence encoding the amino terminal portion of the coding region was not available in GenBank (partial clone accession no. AB003433). The 5'end of the mCRY2 coding region was thus cloned by 5'rapid amplification of cDNA ends. The full-length coding region was then amplified as described above, sequenced, and deposited in GenBank as Accession Number AF156987. The constructs (FIG. 4) were transfected into NIH3T3 cells and both their cellular localization (by immunofluorescence) and ability to inhibit CLOCK: BMAL-1-induced transcription were assessed.

The results clearly showed that mCRY1 translocates to the nucleus when tagged with either the V5 or HA epitope. This was true when HA was placed at either the N-terminal or C-terminal ends, as well as when epitope tags were placed on both ends of the protein. In each instance, the protein was nuclear and inhibited CLOCK:BMAL-1-induced transcription by >90%. Interestingly, when enhanced (E)GFP was fused to either end of mCRY1, immunofluorescence was found diffusely throughout the cell and there was no transcriptional inhibition. The same diffuse staining and lack of transcriptional inhibition was found with EGFP alone. When EGFP was fused to an N-terminal fragment of mCRY1 containing a putative signal sequence for transport into mitochondria, the cellular location was mainly cytoplasmic, punctate and appeared to be in mitochondria. Using a specific anti-mCRY1 antibody, endogenous mCRY1 protein was shown to be nuclear in non-transfected NIH3T3 cells and in SCN. Thus, mCRY1 is normally a nuclear protein and that GFP fused to CRY alters the location of the native protein by changing its conformation. mCRY2-V5 was found in the nucleus, consistent with previous findings (Kobyashi et al., supra; Tresher et al., supra), and the tagged protein inhibited CLOCK:BMAL-1-induced transcription by >90%.

EXAMPLE 7 mCRY1 and mCRY2 Directly Interact with the mPER Proteins and Translocate them into the Nucleus To evaluate the potential for protein: protein interactions between the mCRY and mPER families, co-immunoprecipitation using epitope-tagged proteins was utilized.

COS7 cells co-transfected with expression plasmids encoding mCRY1-HA and either mPER1-V5, mPER2-VS, mPER3-V5, or mTIM-V5 expressed each V5-tagged protein prior to immunoprecipitation. Immunoprecipitation with the HA antibody and analysis of the immunoprecipitated material with anti-V5 antibodies indicated the presence of heterodimeric interactions between mCRY1 and each of the mPER and mTIM proteins. There was no interaction between mCRY1 and βgalactosidase which served as a specificity control. Co-immunoprecipitation experiments using mCRY2-HA instead of mCRY1-HA similarily showed the presence of heterodimeric interactions between mCRY2 and each of the mPER and mTIM proteins.

Having shown that mCRY:mPER heterodimers could exist, the ability of such interactions to translocate the mPER proteins to the nucleus was determined. In marked contrast to the lack of effect of any pairwise combination of mPER-:mPER or mPER:mTIM interactions to translocate mPER1 and mPER2 to the nucleus, each mCRY protein profoundly changed the location all three mPER proteins in NIH3T3 and COS7 cells. This was most apparent for mPER1 and mPER2 which were almost entirely nuclear after co-transfection with either mCRY1 or mCRY2. Curiously, each mCRY protein changed mPER3 from mainly cytoplasm only (>80%) to both cytoplasm and nucleus (>80%) to a degree similar to that induced by co-transfection of mPER3 with mPER1. When mPER3 was co-transfected with mPER1 and either mCRY1 or mCRY2, however, each of the three protein combinations changed mPER3's location from 13–20% nucleus only to predominantly nucleus only (54–68% of transfected cells). Co-transfection of either mCRY1 or mCRY2 with mTIM did not change the predominantly nucleus only location (>90% of transfected cells) of any of the three proteins.

These data indicate that the mCRY proteins can heterodimerize with the mPER proteins and mTIM. The mCRY:mPER interactions mimic the in vivo situation where the interaction of mCRY and mPER results in the almost complete translocation of mPER1 and mPER2 to the nucleus. Moreover, trimeric interactions among the mPER and mCRY proteins appear necessary for complete nuclear translocation of mPER3. The data also suggest that the nuclear translocation of the mPER proteins is dependent on mCRY1 and mCRY2. The mCRY proteins, however, appear to be able to translocate to the nucleus independent of the mPERs. Even with massive overexpression of mCRY proteins in cell culture they are always >90% nuclear.

EXAMPLE 8 mCRY1 and mCRY2 Levels Express Synchronous Circadian Rhythms in the SCN

If nuclear entry of mPER1 and mPER2 is dependent on the mCRY proteins as suggested by the cell culture experiments, then similarily synchronous circadian oscillations of endogenous mCRY1 and mCRY2 levels in the nuclei of SCN neurons might be expected. To determine this the oscillations of endogenous CRY in neurons was determined. Briefly, mice entrained to a schedule of 12L:12D were transferred to constant dim red light. Circadian Time (CT) was initially defined relative to predicted lights-off (CT12), and on the day of sampling was confirmed by the coincident onset of group activity, as monitored by passive infra-red movement detectors. After 20 (CT8) to 42 (CT6) hours in constant dim red light, mice were killed with an anesthetic overdose, and perfused (4% paraformaldehyde). Brains were removed, post-fixed, transferred to cryoprotectant buffered sucrose solution (20%) and then sectioned on a freezing microtome. Alternate freefloating sections (40 $\mu$m) were incubated with affinity purified anti-mCRY1 or anti-mCRY2 (both at 0.5 $\mu$g/ml) primary sera (Alpha Diagnostic International). The sera were raised against synthetic peptides corresponding to specific sequences close to the C-terminals of the mCRY1 (26 amino acids) and mCRY2 (22 amino acids)proteins. To test for specificity of the sera, some SCN sections were incubated with affinity purified sera to which synthetic peptide (10 $\mu$g/ml) had been added. Immunoreaction was visualised by avidin-biotin/peroxidase in conjunction with diaminobenzidine chromogen (Vector Labs, Peterborough, U.K.). Counts of the number of immunoreactive nuclear profiles in the SCN were made using an image analysis system as described previously.

Immunocytochemical analysis of mCRY1 and mCRY2 in the brains of mice sampled at Zeitgeber Time (ZT)15 (3 h after lights off) identified them both as nuclear antigens in the SCN and elsewhere, including piriform cortex (mCRY2) and hippocampus (mCRY1, mCRY2). The majority of SCN neurons appeared to be immunoreactive for the antigen tested, and the immunoreactivities were specific, being blocked by pre-incubation with the peptide (10 $\mu$g/ml) used to raise the respective serum. In contrast, the SCN from animals sampled at ZT3 contained very few mCry1- or mCRY2-immunoreactive nuclei, and those which were evident were located in a dorso-lateral position comparable to that reported for mPER1 immunoreactive nuclei at this phase. Rhythmic expression of mCRY1 and mCRY2 was sustained under free-running conditions, with low levels at Circadian Time (CT)2 and high expression throughout the SCN at CT14 was observed. Quantitative analysis of the number of immunoreactive nuclei in the SCN sampled at 2 h intervals over 24 h in DD showed a clear circadian variation. The abundance of both proteins was low in the early subjective day, rising in later subjective day to peak at CT12–CT16. There was a progressive decline during subjective night to basal counts at CT24. This temporal profile of mCRY1 and mCRY2-immunoreactivity in the SCN is directly comparable with that observed for mPER1 and mPER2, indicative of a synchronous nuclear accumulation of these proteins in the SCN.

In contrast, expression of mCry1- and mCRY2-immunoreactivity in other areas did not exhibit appreciable circadian variation, consistent with the constitutive expression of mPER proteins in brain sites outside the SCN.

These in vivo data, in conjunction with our cell culture data, strongly suggest that the mCRY proteins are the dominant movers of the mPER1 and mPER2 proteins from cytoplasm to nucleus. We do not yet know the temporal pattern of mPER3 immunoreactivity in the SCN, but we have no reason to believe it will be any different from that found for mPER1 and mPER2.

EXAMPLE 9

Dissociation Between the Inhibitory Effects of the mPER Proteins and the mCRY Proteins on Transcription By varying the amounts of mPER and mCRY plasmids in co-transfection experiments, we have observed at best additive effects of pairwise combinations of mPER with mCRY proteins on the inhibition of CLOCK:BMAL-1-mediated transcription. Although these studies in cell culture are confounded by the endogenous expression of the mPer1, mPER2, mPer3, mTim, mCry1 and mCry2 genes in the cell lines used, the lack of synergism of pairwise combinations on transcriptional inhibition suggested that the mPER and mCRY proteins have independent effects on the transcriptional machinery. To examine this in more detail, the fact that MOP4:BMAL-1-heterodimers also activate transcription via a CACGTG E box was exploited (Hogenesch et al., Proc. Natl. Acad Sci. USA 95:5474–5479, 1998).

CLOCK, MOP4, and BMAL-1 alone or in pairwise combinations were tested for transcriptional activation (FIG. 8A). Significant transcriptional activation was seen only when CLOCK and BMAL-1 (10-fold increase) or MOP4 and BMAL 1 (37-fold increase) were co-expressed. Transcriptional activation was dependent on the E-box, because no transcriptional activation was detected when the vasopressin promoter with a mutated E-box was used. The greater levels of transcriptional activation with MOP4:BMAL-1 than with CLOCK:BMAL-1 appeared due to much higher levels of MOP4 protein expression compared with CLOCK based on western blot analysis of epitope tagged proteins.

Figure 5A:
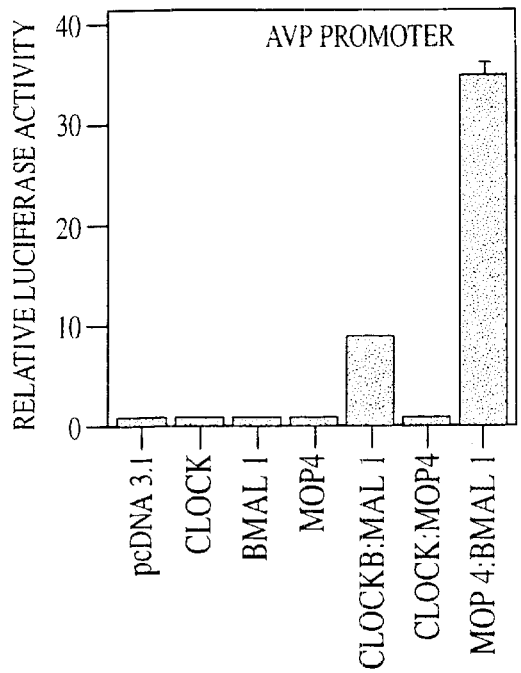
FIGS. 5A–D are histograms depicting the specificity of mouse PER and mouse CRY in inhibiting transcription of Mop4:Bmal-1 mediated transcription.
Figure 5B:
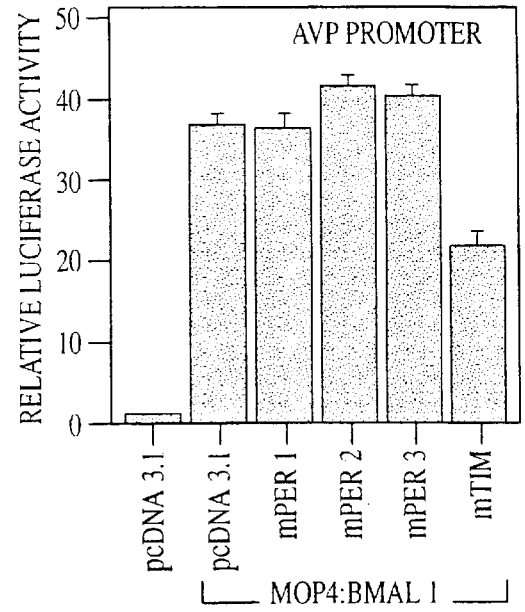
Figure 5C:
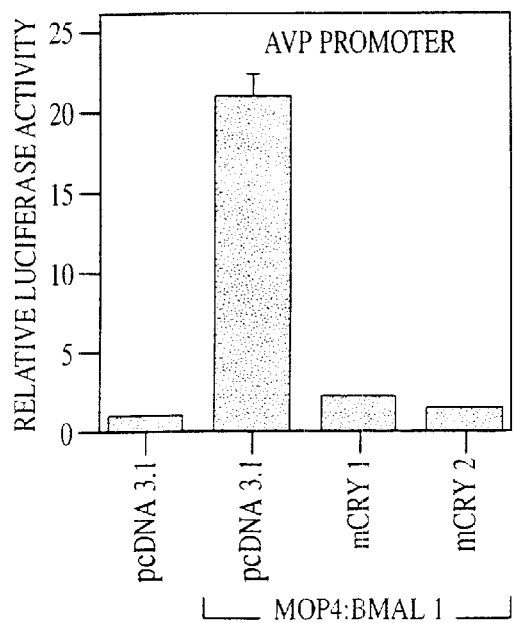
Figure 5D:
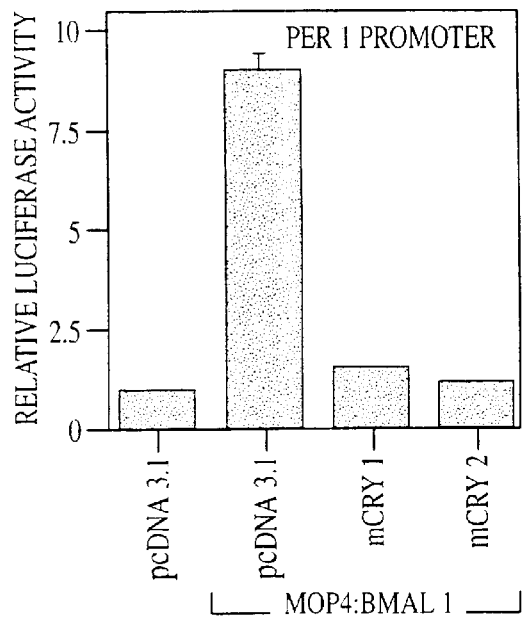

Each mPER alone, mTIM, or each mCRY alone was tested for its ability to inhibit MOP4:BMAL-1-induced transcription. Even though each mPER protein can inhibit CLOCK:BMAL-1-induced transcription, the mPER proteins (500 ng of each plasmid) did not affect MOP4:BMAL-1-induced transcription (FIG. 5B). When the amount of MOP4 was reduced so that the relative luciferase values were equal to those seen with CLOCK and BMAL-1 activation, the mPER expression plasmids were still unable to inhibit transcription. In contrast to the lack of inhibition of the mPER proteins, mTIM (at 500 ng) was able to inhibit MOP4:BMAL-1-induced transcription by about 40% (FIG. 5; p>0.01). Combinations of each mPER and the mTIM expression plasmids, or pairwise combinations of mPER expression plasmids did not inhibit more effectively than when the mTIM plasmid was transfected alone. Remarkably, each mCRY protein (250 ng each) abrogated MOP4:BMAL-1-mediated transcription (FIGS. 5C and 5D).

These data suggest that the mPER proteins have their action on CLOCK, perhaps as mPER:mCRY heterodimers, while the mCRY proteins appear capable of interacting directly with either BMAL-1 or the CACGTG E box. It is worth noting that MOP4 does not appear to play a major role in circadian function, as its RNA is not detectably expressed in the SCN of either wild-type or Clock-mutant mice.

EXAMPLE 10

Bmal1 RNA Rhythm in Clock/Clock Mutant Mice

BMAL-1 RNA rhythm was first documented in mouse SCN using quantitative in situ hybridization (Jin et al., Cell 96:57 (1999)) with an antisense riboprobe that recognizes the two major Bmal1 transcripts in the SCN (Yu et al., Biochem. Biophys. Res. Commun. 260:760 (1999)). Wild-type mice exhibited a robust circadian rhythm in Bmal1 RNA levels, with low levels from circadian time (CT) 6–9 and peak levels from CT 15–18.

Figure 9:
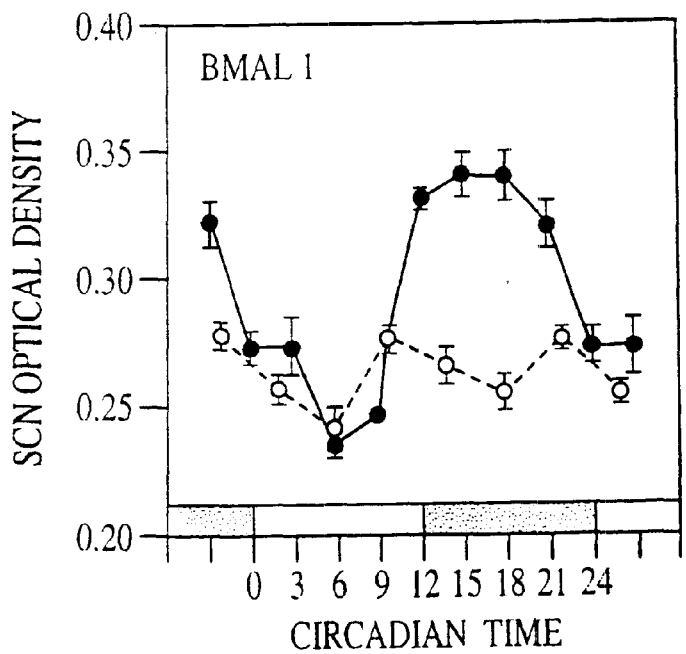
FIG. 9 is a line graph depicting temporal profiles of Bmal1 RNA levels in the SCN of wild type (solid) and Clock/Clock (dashed) mice. Each value is the mean±SEM of 5–9 animals. Data at CT 2, 3, 22, and 24 are double-plotted. Gray bar, subjective day; black bar, subjective night.

The phase of the Bmal1 rhythm is opposite that of the mouse Per1–3(mPer1–3) RNA rhythms (Zylka et al., Neuron 20:1103 (1998); Oishi et al., Biochem. Biophys. Res. Commun. 268:164 (2000); Honma et al., Biochem. Biophys. Res. Commun. 250:83 (1998)). In addition to driving rhythmic transcription of the mPer and mCry genes (Jin et al., Cell 96: 57 (1999); Kume et al., Cell 98:193 (1999)), it seemed possible that CLOCK:BMAL1 heterodimers might simultaneously negatively regulate Bmal1gene expression, similar to a proposed model of clock gene regulation in Drosophila. If CLOCK:BMAL1 heterodimers are negatively regulating Bmal1 gene expression and if the mutant CLOCK protein is ineffective in this negative transcriptional activity, then Bmal1RNA levels should be elevated and less rhythmic in homozygous Clock mutant mice. Compared to wild-types, however, Clock/Clock animals expressed a severely dampened circadian rhythm of Bmal1 RNA levels in the SCN (significant difference between genotypes; ANOVA, P<0.001) (FIG. 9). Trough Bmal1RNA levels did not differ between Clock/Clock mice and wild-types. The peak level of the RNA rhythm in homozygous Clock mutant mice was only≈30% of the peak value in wild-types. A similar blunting of the Bmal1RNA rhythm in the SCN of Clock/Clock mice has been reported by others (Oishi et al., Biochem. Biophys. Res. Commun. 268:164 (2000)).

Figure 10:
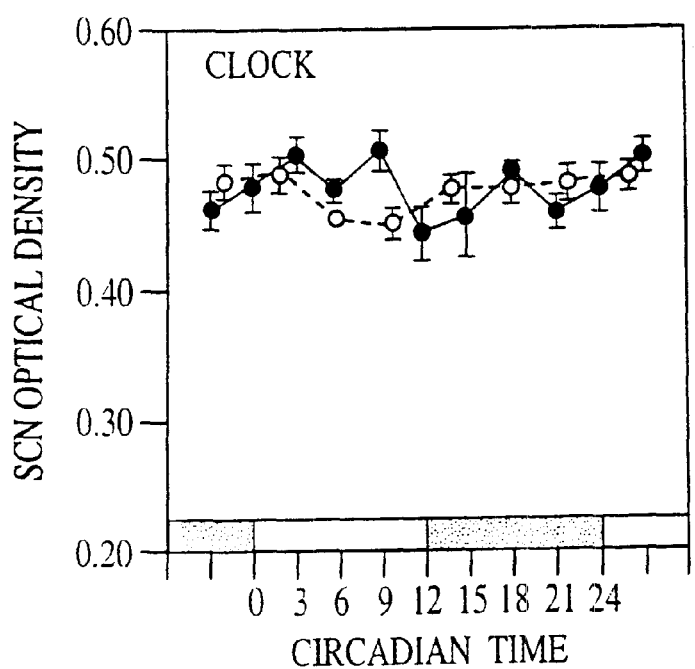
FIG. 10 is a line graph depicting CLOCK mRNA levels in the SCN of wild-type (solid line) or Clock/Clock (dashed line) mice. Each value is the mean±SEM of 5–9 animals. Data at CT 2, 3, 22, and 24 are double-plotted. Gray bar, subjective day; black bar, subjective night.

The temporal profile of Clock RNA levels was examined in the SCN of Clock/Clock mutant animals, since it has been reported that Clock RNA levels (assessed by Northern blot analysis) are decreased in the eye and hypothalamus of Clock/Clock mutant mice (King et al., Cell 89:641 (1991)). Consistent with previous reports (Tei et al., Nature 389:512 (1997); Shearman et al., Neuroscience 89:387 (1999) Clock RNA levels did not manifest a circadian oscillation in mouse SCN. Surprisingly, Clock RNA levels in the SCN of Clock/Clock mutant mice were not significantly different from those in the SCN of wild-type animals (FIG. 10; ANOVA, P>0.05). Thus, the Clock mutation appears to alter regulation of Bmal1gene expression in SCN, but not the regulation of the Clock gene itself. Clock expression may be decreased in other hypothalamic regions.

The low levels of Bmal1 RNA in the SCN of homozygous Clock mutant animals show that CLOCK is not required for the negative regulation of Bmal1. Instead, these data indicate that CLOCK is actually necessary for the positive regulation of Bmal1. The positive effect of CLOCK on Bmal1 levels is probably indirect and may occur via the mPER and/or mCRY proteins, which are expressed in the nucleus of SCN neurons at the appropriate circadian time to enhance Bmal1 gene expression (Kume et al., Cell 98:193 (1999); Field et al., Neuron 25:437(2000)). In addition, the mPer1–3 and mCry1–2 RNA oscillations are all down-regulated in Clock/Clock mutant mice (Jin et al., Cell 96:57 (1999); Kume et al., Cell 98:193 (1999)). Reduced levels of the protein products of one or more of these genes may lead to the reduced levels of Bmal1 in the mutant mice, through loss of a positive drive on Bmal1 transcription.

EXAMPLE 11

Bmal1 and mCry1 RNA Rhythms in mPER2$^{Brdm1}$ Mutant Mice

Homozygous mPER2$^{Brdm1}$ mutant animals have depressed mPer1 and mPER2 RNA rhythms (Zheng et al., Nature 400:167 (1999)). The Bmal1 rhythm in homozygous mPER2$^{Brdm1}$ mutants was examined to determine whether the positive drive on the Bmal1 feedback loop might come from the mPER2 protein. The effects of this mutation on the mCry1 RNA rhythm were also examined.

Figure 11:
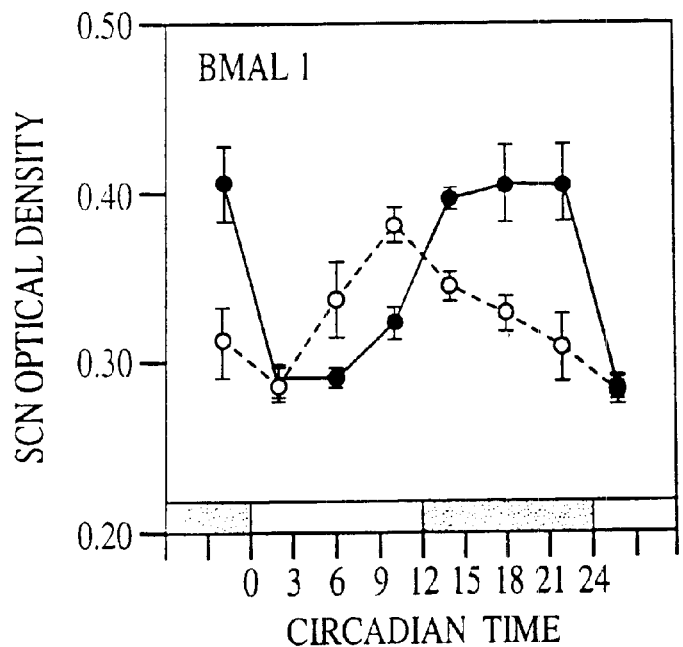
FIG. 11 is a line graph depicting temporal profiles of Bmal1 RNA levels in the SCN of wild-type (solid line) and mPER2$^{Brdm1}$ mutant (dashed line) mice. Each value is the mean±SEM of 4 animals.

The temporal profiles of gene expression were analyzed at six time points over the first day in DD in homozygous mPER2$^{Brdm1}$ mutant mice and wild-type littermates. The Bmal1 RNA rhythm expressed in the SCN of wild-type animals was substantially altered in the SCN of mutant mice (ANOVA, P<0.05)( FIG. 11). Trough RNA levels did not differ between wild-type and mutant animals, but the increase in Bmal1 RNA levels was advanced and truncated in the mutants, compared to the wild-type rhythm.

Figure 12:
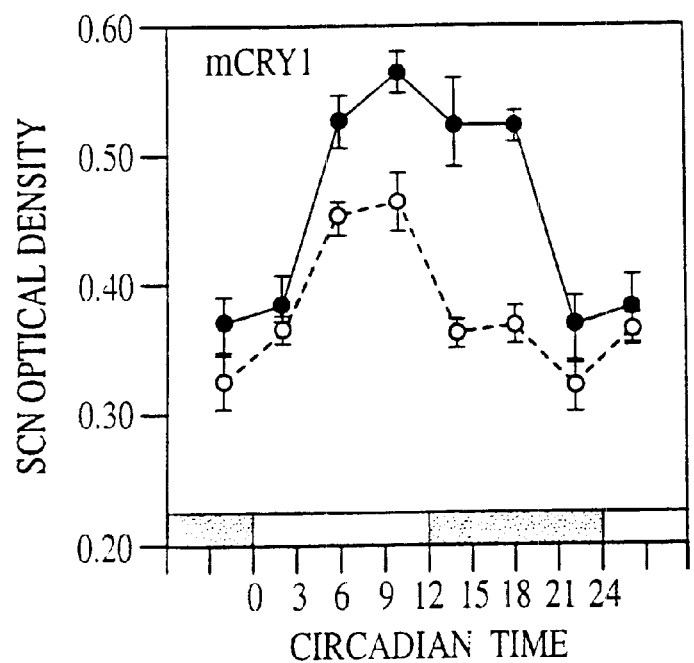
FIG. 12 is a line graph depicting temporal profiles of mCry1 RNA levels in the SCN of wildtype (solid line) and mPER2$^{Brdm1}$ mutant (dashed line) mice are shown. Each value is the mean±SEM of 4 animals.

The mCry1 RNA rhythm was also significantly altered. In the SCN of mPER2$^{Brdm1}$ mutant mice (ANOVA, P<0.0001)( FIG. 12), the peak levels of the mCry1 RNA rhythm were suppressed by≈50%, as reported for mPer1 and mPER2 RNA rhythms in this mouse line (Zheng et al., Nature 400:167 (1999)).

These data suggest that maintenance of a normal Bmal1 RNA rhythm is important for the positive transcriptional regulation of the mPer and mCry feedback loops. Thus, rhythmic Bmal1 RNA levels may drive rhythmic BMAL1 levels which, in turn, regulate CLOCK:BMAL1-mediated transcriptional enhancement in the master clock. Indeed, mPer1, mPER2, and mCry1 RNA rhythms are all blunted in the SCN of mPER2$^{Brdm1}$ mutant mice, in which the Bmal1 rhythm is also blunted. In addition, the homozygous mPER2$^{Brdm1}$ mutation is associated with a shortened circadian period and ensuing arrhythmicity in constant darkness (DD).

These data, along with the fact that Clock RNA levels are unaltered in the SCN of homozygous mPER2$^{Brdm1}$ mutants (Zheng et al., Nature 400:167 (1999), also provide evidence that mPER2 is a positive regulator of the Bmal1 RNA rhythm. This effect may be unique to mPER2. For example, the diurnal oscillation in mPer2 RNA is not altered in the SCN of mPer1-deficient mice, and mPer1, mPer2, and Bmal1 RNA circadian rhythms are not altered in the SCN of mPer3-deficient mice. Moreover, circadian rhythms in behavior are sustained in mice deficient in either mPer1 or mPer3.

EXAMPLE 12 mCRY-Mediated Nuclear Translocation of mPER2 is PAS-Independent

There are at least two ways that the mPER2$^{Brdm1}$ mutation could alter the positive drive of the clock feedback loops.

The mutation could disrupt mPER:mCRY interactions important for the synchronous oscillations of their nuclear localization and/or alter the protein's ability to interact with other proteins (e.g., transcription factors). We examined whether the PAS domain is necessary for functionally relevant mPER2:mCRY interactions, using immunofluorescence of epitope-tagged proteins in COS-7 cells. Briefly, COS-7 cells ($3\times10^5$) were seeded on glass coverslips in 6-well dishes and transfected with Lipofectamine Plus™ (Gibco BRL) with 0.5 ug of total DNA per well. Forty-eight hrs after transfection, cells were processed as described (Sangoram et al., Neuron 21:1101 (1998)). A random population of 30–60 cells from each covership was examined by epiflourescence microscopy and the subcellular distribution of expressed proteins was recorded without knowledge of treatment. At least three independently transfected coverslips were analyzed.

Coexpression of mPER1 or mPER2 with either mCRY1 or mCRY2 in COS-7 cells translocates >90% of mPER1 and mPER2 into the nucleus (Kume et al., Cell 98:193 (1999)). To determine whether the PAS domain of mPER2 is required for this translocation an mPER2 fragment containing residues 1–337 of PER2 ($mPER2^{1-337}$), which includes the PAS domain, was examined in COS-7 cells. $mPER2^{1-337}$ was localized to both cytoplasm and nucleus (89% of transfected cells)( FIG. 13) and the localization was not changed by co-expression with mCRY1. Co-expression of $mPER2^{338-1257}$ with mCRY1, however, dramatically changed the cellular location of the $mPER2^{338-1257}$ fragment from cytoplasm only (12%) to nucleus only (85%). Co-expression of $mPER2^{Brdm1}$ (missing residues 348–434) with mCRY1 also moved mutant $mPER^{2Brdm1}$ into the nucleus, from cytoplasm only (100% when expressed alone) to predominantly both cytoplasm and nucleus (81%) when co-expressed with mCRY1 (FIG. 13). The same patterns of cellular localization were found when mCRY2 was co-expressed with these mPER2 constructs instead of mCRY1 . Thus, functional mPER2:mCRY interactions are not mediated through the PAS domain. Similarly, the PAS domain was not important for the mCRY-mediated nuclear translocation of mPER1 in COS-7 cells.

The data show mPER:mCRY interactions necessary for nuclear transport of the mPER1 and mPER2 proteins occur through domains outside the PAS region. Thus, the PAS domain of an mPER2:mCRY heterodimer might be free to bind to an activator (e.g., transcription factor) and shuttle it into the nucleus to activate Bmal1 transcription. Alternatively, once in the nucleus, mPER2:mCRY heterodimers or mPER2 monomers could coactivate Bmal1 transcription through a PAS-mediated interaction with a transcription factor (Glossop et al., Science 286:766 (1999)). mPER2 itself does not possess a DNA binding motif (Shearman et al., Neuron 19:1261 (1997)).

EXAMPLE 13

Bmal1 RNA Levels in Mice Lacking mCrvl and mCry2

The tonic mid-to-high mPer1 and mPer2 RNA levels in mCry-deficient mice (van der Horst et al., Nature 398:627 (1999) suggest that CLOCK:BMAL1 heterodimers might be constantly driving mPer1 and mPer2 gene expression in the absence of transcriptional inhibition by the mCRY proteins. To examine whether Bmal1 RNA levels would also be modestly elevated, Bmal1 RNA levels in the SCN of mCry-deficient mice were compared to those in the SCN of wild-type mice of the same genetic background at CT 6 and at CT 18 on the first day in DD. The mCRY-deficient (double mutant) colony of mice had a C57BL/6×129 hybrid background, and wild-type controls were of the same genetic background (van der Horst et al., Neuroreport 10:3165 (1999)). Sex ratios of male and female mice were balanced across time points. We also examined Clock RNA levels in these animals.

Figure 14:
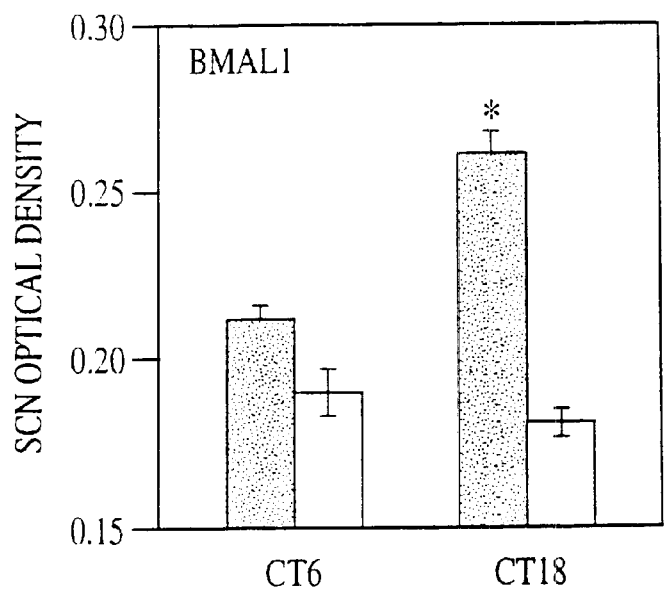
FIG. 14 is a histogram depicting attenuated peak levels of Bmal1 RNA in mCry-deficient mice. Quantitation of Bmal1 RNA levels in the SCN of wild-type (solid bars) and mCry-deficient (open bars) mice. Values are the mean±SEM of 5 animals. Mice were studied on the first day in DD. * is the significance difference in Bmal1 RNA levels between CT 6 and CT 18 in wild-type mice; P<0.0001.
Figure 15:
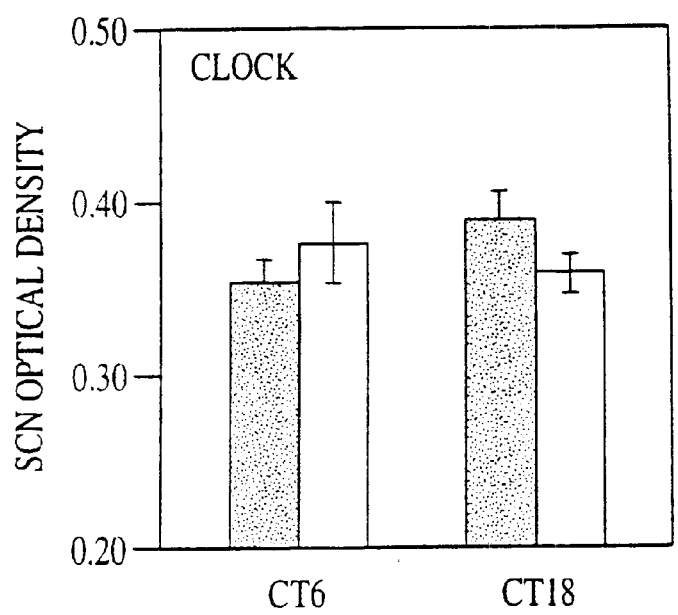
FIG. 15 is a histogram depicting quantitation of Clock RNA levels in the SCN of wild-type (solid bars) and mCry-deficient (open bars) mice. Values are the mean±SEM of 5 animals.

In wild-type animals, the typical circadian variation in Bmal1 RNA levels was apparent with high levels at CT 18 and low levels at CT 6 (P<0.001) (FIG. 14). In mCry-deficient mice, on the other hand, Bmal1RNA levels were low at both circadian times (P>0.05) (FIG. 15). Clock RNA levels did not differ as a function of circadian time or genotype (P>0.05) (FIG. 15).

The unexpectedly low Bmal1 gene expression in the SCN of mCry-deficient mice suggests that the Bmal1 feedback loop is disrupted in the mutant animals, with a resultant non-functional circadian clock. Nevertheless, enough Bmal1gene expression and protein synthesis occurs for heterodimerization with CLOCK so that, without the strong negative feedback normally exerted by the mCRY proteins, mPer1 and mPer2 gene expression is driven sufficiently by the heterodimer to give intermediate to high RNA values (depending on RNA stability).

EXAMPLE 14 mPER1 and mPER2 Localization in mCrv-Deficient Mice

The mid to high mPer1 and mPer2 RNA levels in the SCN of mCry-deficient mice, and simultaneous low Bmal1 levels, suggests that mPER1 and mPER2 proteins may not be exerting much positive or negative influence on the core feedback loops. To test this, immunocytochemistry was used to determine whether mPER1 and mPER2 were tonically expressed in the nuclei of SCN cells in mCry-deficient mice, since nuclear location is necessary for action on transcription (Kume et al., Cell 98:193 (1999); Field et al., Neuron 25:437 (2000)).

mPER1 immunoreactivity exhibited a robust rhythm of nuclear staining in the SCN of wild-type mice, with high values at CT 12 (328±3.5, mean±SEM of positive nuclei per 30 $\mu$m section, n=3) and significantly lower values at CT 24 (54±5, n=3; P<0.01) values are very similar to those previously reported in other strains of mice (Field et al., Neuron 25:437 (2000)).

The pattern of mPER1 immunoreactivity in the SCN of mCry-deficient mice was quite different, however. mPER1 immunoreactivity was detected in the nucleus of a similar number of SCN neurons at each of the two circadian times (CT 12, 140±9, n=3; CT 24, 152±21, n=3), and the counts at each time were at ≈40% of those seen at peak (CT 12) in wild-type animals.

The double mCry mutation also altered the sub-cellular distribution of mPER1 staining in the SCN. In wild-type mice, mPER1 staining viewed under contrast interference was clearly nuclear with a very condensed immunoreaction and a clear nucleolus. The neuropil of the SCN in wild-types was devoid of mPER1 immnunoreactivity. In the SCN of mCry-deficient animals, mPER1 staining was clearly nuclear, but the nuclear profiles were less well defined and less intensely stained, and perinuclear, cytoplasmic immunoreaction could be observed. In addition, the neuropil staining for mPER1 was higher in mCry-deficient mice, although dendritic profiles were not discernible. In the same brains, the constitutive nuclear staining for mPER1 normally seen in the piriform cortex was not altered in mCry-deficient animals.

mPER2-immunoreactivity also exhibited a robust rhythm of nuclear staining in the SCN of wild-type mice, with high counts at CT 12 (371±11, n=3) and significantly lower counts at CT 24 (31±3, n=3; P<0.01), similar to that previously reported in another strain (Field et al., Neuron 25:437 (2000)). In striking contrast, the pattern of mPER2-immunoreactivity in the SCN of mCry-deficient mice was dramatically altered. There were extremely few mPER2-immunoreactive cells in the SCN of mCry-deficient animals at either circadian time (CT 12, 12±1, n=3; CT 24, 8±2, n=3).

In the wild-type mice, the mPER2 staining profiles were clearly nuclear, with well-defined outlines and nucleoli devoid of reaction product. In the few mPER2-immunoreactive cells in the SCN of mCry-deficient mice, low level mPER2 staining was observed in the nucleus, but the profiles were poorly defined and low intensity perinuclear staining could also be observed. As for mPER1, genotype had no discernible effect on nuclear mPER2 immunoreactivity in the piriform cortex, although there was evidence of a low level of perinuclear immunoreactivity for mPER2 in piriform cortex of mCry-deficient mice.

The marked reduction of mPER2 staining in the SCN of mCry-deficient animals suggests that the mCRY proteins are either directly or indirectly important for mPER2 stability, as mPER2 RNA levels are at tonic intermediate to high levels in mCry-deficient mice, similar to those found for mPer1 RNA levels (Okamura et al., Science 286:2531 (1999)). It seems unlikely that our assay is incapable of detecting mPER2 in the cytoplasm of mCry-mutants, since the PER2 antibody can detect cytoplasmically localized antigen in SCN cells (Field et al., Neuron 25:437 (2000)).

The low levels of mPER2 immunoreactivity in the SCN of mCry-deficient mice, in conjunction with tonically low Bmal1 RNA levels, is consistent with an important role of mPER2 in the positive regulation of the Bmal1 loop. Since mPER1 is present in SCN nuclei in mCry-deficient mice, yet Bmal1 RNA is low, it appears likely that mPER1 likely has little effect on the positive regulation of the Bmal1 feedback loop or negative regulation of the mPer1–3 cycles.

The immunohistochemical data also indicate that mPER1 and mPER2 can each enter the nucleus even in the absence of mCRY:mPER interactions. mPER1 is expressed in the nucleus of SCN neurons from mCry-deficient mice, and both mPER1 and mPER2 are constitutively expressed in the nucleus of cells in the piriform cortex of mCry-deficient animals. The phosphorylation state of mPER1 dictates its cellular location in the absence of mPER1:mCRY interactions, since its phosphorylation by casein kinase I epsilon leads to cytoplasmic retention in vitro. Thus, the nuclear location of both mPER1 and mPER2 in vivo may depend on several factors, including interactions with mCRY and other proteins and their phosphorylation.

EXAMPLE 15 mCRY-Induced Inhibition of Transcription

The intermediate to high levels of mPer1 and mPER2 gene expression throughout the circadian day in mcry-deficient mice (Okamura et al., Science 286:2531 (1999); Vitaterna et al., Proc. Natl. Acad. Sci. USA 96:12114 (1999)) is consistent with a prominent role of the mCRY proteins in negatively regulating CLOCK:BMAL1-mediated transcription, as in vitro data have suggested (Kume et al., Cell 98:193 (1999)). The endogenous expression of the mCry1, mCry2, and mPer1–3 genes in mammalian cell lines, however, has obscured rigorous in vitro analysis of the mechanism. Therefore, an insect cell line, Schneider (S2) cells, a Drosophila cell line that expresses cycle (the Drosophila Bmal1) but not per, Tim, and clock (Saez et al., Neuron 17:911 (1996); Darlington et al., Science 280:1599 (1998)), was used to study the negative regulation of mCRY1 and mCRY2 on E box-mediated transcription with a luciferase reporter that consists of a tandem repeat of the Drosophila per E box (CACGTG) and flanking nucleotides fused to hsp7o driving luciferase (Darlington et al., Science 280:1599 (1998)). Briefly, S2 cells were transfected with Cellfectin™ (Gibco BRL). Each transfection consisted of 10 to 100 ng of expression plasmid with indicated inserts in pAC5.1-V5, 10 ng luciferase reporter, and 25 ng of β-gal internal control plasmid (driven by baculovirus immediate-early gene, ie-1 promoter). Total DNA for each transfection was normalized using pAC5.1-V5. Cells were harvested 48 hrs after tranfection. Luciferase activity was normalized by determining luciferase:β-gal activity ratios and averaging the values from triplicate wells.

Figure 16:
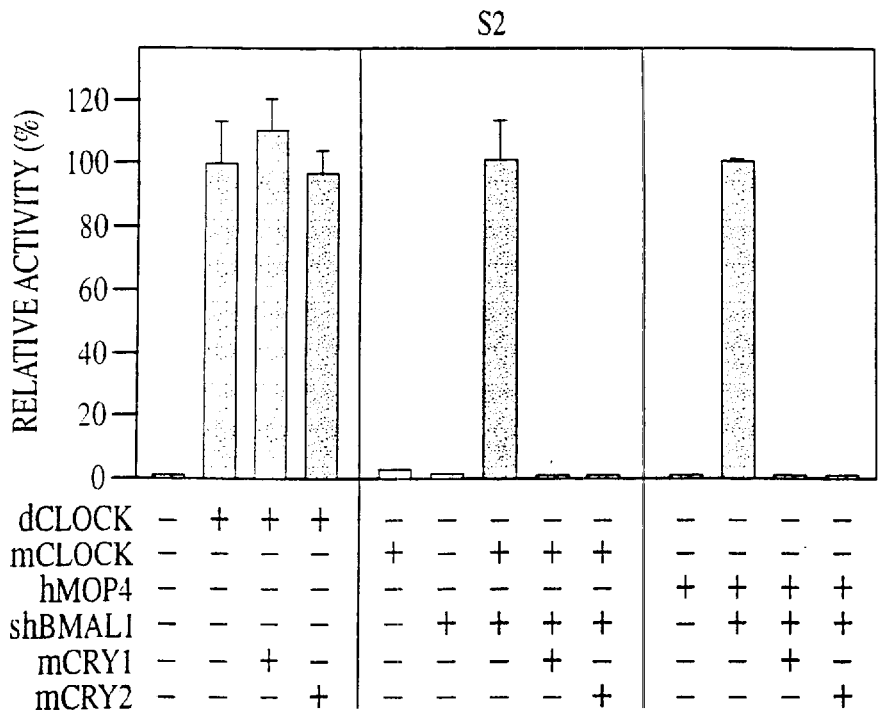
FIG. 16 is a histogram depicting the effects of mCRY proteins on transcriptional activation in Drosophila S2 cells. Values are luciferase activity expressed as relative to the response in presence of activators (100%). Each value is the mean±SEM of three replicates from a single assay.

Since S2 cells express endogenous cyc, transfection with dclock alone caused a large increase in transcriptional activity (265-fold), as described (Darlington et al., Science 280:1599 (1998)). As for dCRY (Ceriani et al., Science 285:553 (1999)), this activation was not inhibited by either mCRY1 or mCRY2. When co-transfected, mCLOCK and syrian hamster (sh)BMAL1 heterodimers induced a large increase in transcriptional activity (1744-fold) that was reduced by >90% by mCRY1 or mCRY2 (FIG. 16). Moreover, cotransfection of shBmal1 and human (h)Mop4, but not transfection of hMop4 alone, similarly caused a large increase in transcriptional activity in S2 cells (539-fold), like that previously found for hMOP4:shBMAL1 heterodimers in mammalian cells (Hogenesch et al., Proc. Natl. Acad. Sci. USA. 95:5474 (1998); Kume et al., Cell 98:193 (1999)). hMOP4:shBMAL1-mediated transcription was also blocked by either mCRY1 or mCRY2 (FIG. 16). The mCLOCK:shBMAL1- and hMOP4:shBMAL1-induced transcription in S2 cells was dependent on an intact CACGTG E box, because neither heterodimer caused an increase in transcription when a mutated E box reporter was used in the transcriptional assay. Immunofluorescence of epitope-tagged mCRY1 or mCRY2 expressed in S2 cells showed that each was >90% nuclear in location, as in mammalian cells (Kume et al., Cell 98:193 (1999)).

These data indicate that mCRY1 and mCRY2 are nuclear proteins that can each inhibit mCLOCK:shBMAL1-induced transcription independent of the mPER and mTIM proteins and of each other. The results also show that the inhibitory effect is not mediated by the interaction of either mCRY1 or mCRY2 with the E box itself, since E box-mediated transcription was not blocked by the mCRY proteins when transcription was activated by dCLOCK:CYC heterodimers. It thus appears that the mCRY proteins inhibit mCLOCK:shBMAL1-mediated transcription by interacting with either or both of the transcription factors, since a similar inhibition was found with hMOP4:shBMAL1-induced transcription. The system was performed as described in Gekakis et al. (Science 270:811 (1995)). Yeast two-hybrid assays revealed strong interactions of each mCRY protein with mCLOCK and shBMAL1. Weaker interactions were detected between each mCRY protein and hMOP4. This is further evidence of functionally relevant associations of each mCRY protein with each of the three transcription factors (Griffin et al., Science 286:768 (1999)).

Figure 17:
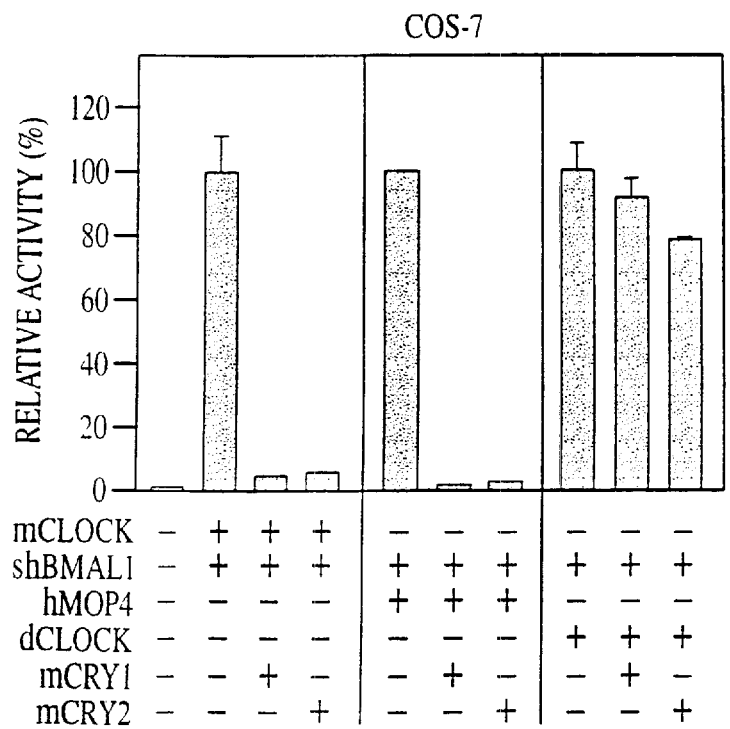
FIG. 17 is a histogram depicting the effects of mCRY proteins on transcriptional activation in COS-7 cells. Presence (+) or absence (−) of luciferase reporter (pGL3-Basic) (10 ng) and expression plasmids (0.25 ug mClock, shBmal1, hMop4, dclock; 0.1 ug mCry1, mCry2) is denoted. Values are luciferase activity expressed as relative to the response in presence of activators (100%). Each value is the mean±SEM of three replicates from a single assay. The results shown are representative of three independent experiments.

Next it was determined whether the mCRY-induced inhibition of transcription was through interaction with CLOCK and/or BMAL1. Since neither mCRY1 or mCRY2 inhibited dCLOCK:CYC mediated transcription, the ability of each to inhibit dCLOCK:shBMAL1-mediated transcription was examined. This aspect of study could not be examined in S2 cells, because of the strong activation induced by transfecting dclock alone in S2 cells where there is strong endogenous cyc expression. Briefly, luciferase reporter gene assays were performed in COS-7 cells as described (Jin et al., Cell 96:57 (1999)). mCRY1 and mCRY2 completely inhibited mCLOCK:shBMAL1- and hMOP4:shBMAL1-induced transcription in COS-7 cells (FIG. 17, Left and Middle, respectively), while the cryptochromes did not inhibit dCLOCK:shBMAL1-mediated transcription by more than 20% (FIG. 17). Thus, mCRY inhibits mCLOCK:shBMAL1-induced transcription through interaction with either mCLOCK alone or through an association with both mCLOCK and BMAL1 in a multiprotein complex. Unfortunately, the examination of the inhibition of mCLOCK:CYC heterodimers was not possible, because co-transfection of mClock and cyc did not activate transcription in either insect cells or mammalian cells, even though strong interactions between mCLOCK and CYC were detected in yeast.

EXAMPLE 16

Identifying a Role for Mouse Tim

To delineate potential functions for mTim, the gene was disrupted by targeted mutagenesis. A targeting vector was designed from a 15 kb genomic clone in which a portion of the gene was replaced with a PGK-Neo cassette; this deletion-insertion disrupts mTIM after codon 178 (of 1 197). Homologous recombination of the targeted allele was obtained in 129/Sv J1 embryonic stem cells, and two clones were microinjected into C57BL/6 mouse blastocysts. Chimeric offspring were mated and germline transmission was obtained.

When heterozygous animals were crossed, the resulting litters contained a 1:2 ratio of wild-type to heterozygous offspring, but no homozygous mutants. Of the offspring analyzed by Southern blotting, 29 contained only the wild-type allele and 58 were heterozygous for the mTim mutation. These results are consistent with mTim being essential for mouse survival.

Heterozygous mTim mutant embryos had reduced mTIM protein levels, confirming the targeting event; wild-type levels=8.04±2.07 (mean±SEM; n=4) versus heterozygote levels=2.98±0.61 (n=5; p<0.05, unpaired t test). Heterozygous mTim mutants had no obvious developmental or behavioral abnormalities.

Heterozygous mTim mutant animals displayed circadian rhythms in locomotor activity indistinguishable from wild-type mice of isogenic background. Rhythmic wheel-running activity of both groups persisted in constant conditions (>25 days). Furthermore, the period of locomotor activity was unchanged; wild-type mice displayed a period of 23.52±0.22 hrs (n=4) vs. 23.73±0.13 hrs (n=8) for heterozygotes (p >0.05, Studen t-test). The lack of period change in heterozygotes does not rule out a clock-relevant function for mTim, because the null Tim mutation in Drosophila is recessive.

The mortality rate of homozygous mTim mutant embryos at different gestational ages was next determined. Histological analysis of embryos from 13 litters from heterozygous mTim mutant crosses spanning embryonic day (ED) 6.5 to 11.5 showed a mortality rate of 4 1%. When corrected for naturally occurring prenatal attrition (14%, determined from heterozygous female X wild-type male matings), the lethality rate was 25.5%, consistent with the predicted Mendelian rate for a mutation that is lethal when homozygous.

Developmental defects due to the mTim mutation were striking at ED 7.5. At this stage, presumptive homozygous embryos lack any cellular organization, with necrotic cell debris filling the amniotic cavity, and resorption by surrounding maternal tissues has already begun. Developmental abnormalities were observed in embryos as early as ED 5.5 (data not shown), indicating that mTim is essential for development around the time of implantation. The mechanism behind the essential role of mTIM for mouse development is currently not known. At ED 7.5, in situ hybridization showed that mTim RNA is expressed throughout the embryo, particularly in the embryonic germ cell layers and in the ectoplacental cone.

The results show that mTim is essential for embryonic development.

---

What is claimed is:

1. A method for identifying a compound which binds to a mammalian CRY protein, the method comprising:

contacting the CRY protein with a test compound; and determining whether the CRY protein binds to the test compound, wherein binding by the test compound to the CRY protein indicates that the test compound is a CRY protein binding compound.

2. The method of claim 1, wherein the CRY protein is CRY1 or CRY2.

3. The method of claim 1, wherein the test compound is radiolabeled.

4. The method of claim 1, further comprising:

contacting the test compound with the CRY protein in the presence of a PER protein; and determining whether the test compound disrupts the association of the CRY protein with the PER protein, wherein a decrease in the association in the presence of the test compound compared to the association in the absence of the test compound indicates that the test compound disrupts the association of the CRY protein and with PER protein.

5. The method of claim 4, wherein the CRY protein is a mouse CRY1 or CRY2.

6. The method of claim 4, wherein the PER is a mouse PER1, PER2 or PER3.

7. The method of claim 1, further comprising:

contacting the test compound with the CRY protein in the presence of a TIM protein; and determining whether the test compound disrupts the association of the CRY protein with the TIM protein, wherein a decrease in the association in the presence of the test compound compared to the association in the absence of the test compound indicates that the test compound disrupts the association of the CRY protein with the TIM protein.

8. The method of claim 1, further comprising:

contacting the test compound with the CRY protein in the presence of a CLOCK:BMAL-1 complex; and determining whether the test compound disrupts the association of the CRY protein with the CLOCK:BMAL-1 complex, wherein a decrease in the association in the presence of the test compound compared to the association in the absence of the test compound indicates that the test compound disrupts the association of the CRY protein with the CLOCK:BMAL-1 complex.

9. The method of claim 1, further comprising:

contacting the test compound with the CRY protein in the presence of a BMAL-1 protein; and determining whether the test compound disrupts the association of the CRY protein with the BMAL-1 protein, wherein a decrease in the association in the presence of the test compound compared to the association in the absence of the test compound indicates that the test compound disrupts the association of the CRY protein with the BMAL-1 protein.

10. The method of claim 1, further comprising:

contacting the test compound with the first CRY protein in the presence of a second CRY protein; and determining whether the test compound disrupts the association of the first CRY protein with the second CRY protein, wherein the second CRY protein has an amino acid sequence the same as or different than the first CRY protein, and wherein a decrease in the association in the presence of the test compound compared to the association in the absence of the test compound indicates that the test compound disrupts the association of the first CRY protein and the second protein.

11. The method of claim 10, wherein the first CRY protein is CRY1 or CRY2.

12. The method of claim 10, wherein the second CRY protein is CRY1 or CRY2.

13. The method of claim 1, further comprising:

providing a cell comprising a CRY protein, a CLOCK:BMAL-1 complex, and a DNA comprising an E-box operatively linked to a reporter gene;

introducing the test compound into the cell; and assaying for transcription of the reporter gene in the cell, wherein an increase in transcription in the presence of the compound compared to transcription in the absence of the compound indicates that the compound blocks CRY-induced inhibition of CLOCK:BMAL-1-mediated transcription in a cell.

14. The method of claim 13, wherein the cell is a NIH3T3 cell or a clock neuron.

15. The method of claim 13, wherein the reporter gene encodes luciferase.

16. A method for identifying a compound which disrupts the association of a CRY protein and a PER protein, the method comprising:

contacting a test compound with the CRY protein in the presence of the PER protein; and determining whether the test compound disrupts the association of the CRY protein and the PER protein, wherein a decrease in the association in the presence of the test compound compared to the association in the absence of the test compound indicates that the test compound disrupts the association of the CRY protein and the PER protein.

17. The method of claim 16, wherein the CRY protein is a mouse CRY1 or CRY2.

18. The method of claim 16, wherein the PER protein is a mouse PER1, PER2 or PER3.

19. A method for identifying a compound which disrupts the association of a CRY protein and a TIM protein, the method comprising:

contacting a test compound with the CRY protein in the presence of the TIM protein; and determining whether the test compound disrupts the association of the CRY protein and the TIM protein, wherein a decrease in the association in the presence of the test compound compared to the association in the absence of the test compound indicates that the test compound disrupts the association of the CRY protein and the TIM protein.

20. The method of claim 19, wherein the CRY protein is a mouse CRY1 or CRY2.

21. The method of claim 19, wherein the TIM protein is a mouse TIM.

22. The method of identifying a compound that disrupts the association between a CRY protein and a CLOCK:BMAL-1 complex, the method comprising:

contacting a test compound with the CRY protein in the presence of a CLOCK protein amd a BMAL-1 protein; and determining whether the test compound disrupts the association of the CRY protein with a complex of the CLOCK protein and the BMAL-1 protein, wherein a decrease in the association in the presence of the test compound compared to the association in the absence of the test compound indicates that the test compound disrupts the association of the CRY protein and the CLOCK:BMAL-1 complex.

23. The method of claim 22, wherein the CRY protein is mouse CRY1 or CRY2.

24. The method of claim 22, wherein the CLOCK protein is mouse CLOCK and the BMAL-1 protein is mouse BMAL-1.

25. A method for identifying a compound which disrupts the association of a CRY protein and a BMAL-1 protein, the method comprising:

contacting a test compound with the CRY protein in the presence of the BMAL-1 protein; and determining whether the test compound disrupts the association of the CRY protein and the BMAL-1 protein, wherein a decrease in the association in the presence of the test compound compared to the association in the absence of the test compound indicates that the test compound disrupts the association of the CRY protein and the BMAL-1 protein.

26. The method of claim 25, wherein the CRY protein is a mouse CRY1 or CRY2.

27. The method of claim 25, wherein the BMAL-1 protein is a mouse BMAL-1.

28. A method for identifying a compound which disrupts the association of a first CRY protein and a second CRY protein, the method comprising:

contacting a test compound with the first and second CRY proteins; and determining whether the test compound disrupts the association of the first CRY protein with the second CRY protein, wherein the second CRY protein has an amino acid sequence the same as or different than the first CRY protein, and wherein a decrease in the association in the presence of the test compound compared to the association in the absence of the test compound indicates that the test compound disrupts the association of the first protein with the second CRY protein.

29. The method of claim 28, wherein the first CRY protein is a mouse CRY1 or CRY2.

30. The method of claim 28, wherein the second CRY protein is a mouse CRY1 or CRY2.

31. A method for identifying a compound that blocks CRY induced-inhibition of CLOCK:BMAL-1 transcription in a cell, the method comprising:

providing a cell comprising a CRY protein, a CLOCK:BMAL-1 complex, and a DNA comprising an E-box operatively linked to a reporter gene;

introducing the compound into the cell; and assaying for transcription of the reporter gene in the cell, wherein an increase in transcription in the presence of the compound compared to transcription in the absence of the compound indicates that the compound blocks CRY-induced inhibition of CLOCK:BMAL-1-mediated transcription in a cell.

32. The method of claim 31, wherein the cell is a NIH3T3 cell or a clock neuron.

33. The method of claim 31, wherein the reporter gene encodes a luciferase.

* * * * *

UNITED STATES PATENT AND TRADEMARK OFFICE
CERTIFICATE OF CORRECTION

PATENT NO.     : 6,475,744 B1  
DATED          : November 5, 2002  
INVENTOR(S)    : Steven M. Reppert et al.

Page 1 of 1

It is certified that error appears in the above-identified patent and that said Letters Patent is hereby corrected as shown below:

Title page,
Item [56], References Cited, OTHER PUBLICATIONS,
"Albarracin et al.," reference, replace "Recpetor" with -- Receptor --.
"Altschul et al.," reference, replace "Blast" with -- BLAST --; and
replace "Psi-Blast" with -- PSI-BLAST --.
"Carlson et al.," reference, replace "Malation" with -- Melatonin --.
"Ceriani et al.," reference, replace "Timeless" with -- TIMELESS --; and
replace "Cryptochrome" with -- CRYPTOCHROME --.
"Chomeczbski et al.," reference, replace "Chomeczbski" with -- Chomczynski --.
"Darlington et al.," reference, replace "Clock" with -- CLOCK --.
"Dubocovich et al.," reference, replace "characterizes" with -- characterize --.
"Gekakis et al.," reference, replace "AB105203" with -- AB015203 --.
"King et al.," reference, replace "clock" with -- CLOCK --.
"Lyon et al.," reference, replace "Newletter" with -- Newsletter --.
"Miller et al.," reference, replace "Package" with -- Packaging --.
"Munson et al.," reference, replace "Ligand" with -- LIGAND --.
"Price et al.," reference, replace "Period" with -- PERIOD --.
"Sangoram et al.," reference, after "Regulate..." insert -- " --.
"Singer et al.," reference, replace "activatyion" with -- activation --.
"Tei et al.," reference, replace "Photorecptor" with -- Photoreceptor --.
"van der Host et al.," reference, replace "Host" with -- Horst --.
"Wang et al.," reference, replace "Circadian Clock Associated" with
-- CIRCADIAN CLOCK ASSOCIATED --; and before "(CCA1)" insert -- 1 --.

Column 108,
Line 32, insert -- CRY -- between "first" and "protein".

Signed and Sealed this

Tenth Day of February, 2004

JON W. DUDAS  
*Acting Director of the United States Patent and Trademark Office*

SEQUENCE LISTING

<160> NUMBER OF SEQ ID NOS: 13

<210> SEQ ID NO 1
<211> LENGTH: 4424
<212> TYPE: DNA
<213> ORGANISM: Mus musculus
<220> FEATURE:
<221> NAME/KEY: CDS
<222> LOCATION: (152)...(3742)

<400> SEQUENCE: 1

```
ctcagccgag tggcgggaaa ggctgcgacc ccgcacctca gggcctcagg ctctgcgagg      60
cttcagagga ctcgcggaga gcggtcccgt aggcctcacc ctctccgtcc accatctcta     120
ctgcccgctc tgctggttgg gcctctggtg t atg gac ttg tac atg atg aac        172
                                   Met Asp Leu Tyr Met Met Asn
                                    1               5 tgt gaa ctt cta gcc acg tgt agc gcc ctt ggg tac ttg gaa gga ggg       220
Cys Glu Leu Leu Ala Thr Cys Ser Ala Leu Gly Tyr Leu Glu Gly Gly
```

```
                10                       15                      20
act tac cac aag gag ccg gat tgc ctg gag agt gtg aag gat ttg atc     268
Thr Tyr His Lys Glu Pro Asp Cys Leu Glu Ser Val Lys Asp Leu Ile
     25                      30                  35 cga tac ctg agg cac gag gat gag acc cga gat gtg cgg cag cag ctg     316
Arg Tyr Leu Arg His Glu Asp Glu Thr Arg Asp Val Arg Gln Gln Leu
 40                      45                  50                  55 gga gct gca cag atc ctg cag agc gac ctc ctg cca atc ctc acg cag     364
Gly Ala Ala Gln Ile Leu Gln Ser Asp Leu Leu Pro Ile Leu Thr Gln
                     60                  65                  70 cat cgc cag gac aag cct ctc ttc gat gcc gtg atc agg ctg atg gta     412
His Arg Gln Asp Lys Pro Leu Phe Asp Ala Val Ile Arg Leu Met Val
             75                  80                  85 aat ttg aca cag cca gcc ttg ctc tgt ttt ggc agc gtg cct aag gac     460
Asn Leu Thr Gln Pro Ala Leu Leu Cys Phe Gly Ser Val Pro Lys Asp
         90                  95                 100 tcc agt gta cgg cac cat ttt ctg cag gtt cta acg tac ctg caa gcc     508
Ser Ser Val Arg His His Phe Leu Gln Val Leu Thr Tyr Leu Gln Ala
    105                 110                 115 tac aaa gag gcc ttt gcc agt gag aag gca ttt gga gtc ctc agc gag     556
Tyr Lys Glu Ala Phe Ala Ser Glu Lys Ala Phe Gly Val Leu Ser Glu
120                 125                 130                 135 acc ttg tat gaa ttg cta cag ctg ggc tgg gag gat cgg caa gaa gaa     604
Thr Leu Tyr Glu Leu Leu Gln Leu Gly Trp Glu Asp Arg Gln Glu Glu
                140                 145                 150 gac aac ttg ctg atc gag cgg atc ctt ctg ctg gtc aga aat att ctc     652
Asp Asn Leu Leu Ile Glu Arg Ile Leu Leu Leu Val Arg Asn Ile Leu
            155                 160                 165 cat gtc ccg gcc aac ctt gag cag gag aag agt atc gat gat gat gcc     700
His Val Pro Ala Asn Leu Glu Gln Glu Lys Ser Ile Asp Asp Asp Ala
        170                 175                 180 agc atc cac gac cgt ctc ctt tgg gca att cac ctc agt ggc atg gac     748
Ser Ile His Asp Arg Leu Leu Trp Ala Ile His Leu Ser Gly Met Asp
    185                 190                 195 gac ttg ctc ctc ttc ctg tcc agc tca tcc gcc gag cag cag tgg agc     796
Asp Leu Leu Leu Phe Leu Ser Ser Ser Ala Glu Gln Gln Trp Ser
200                 205                 210                 215 ctc cat gtg ctg gag atc atc tcc ctc atg ttc cga gac cag acc cct     844
Leu His Val Leu Glu Ile Ile Ser Leu Met Phe Arg Asp Gln Thr Pro
                220                 225                 230 gag cag cta gcg gga gta ggg cag gga cgc ttg gct cag gag cga agc     892
Glu Gln Leu Ala Gly Val Gly Gln Gly Arg Leu Ala Gln Glu Arg Ser
            235                 240                 245 acg gat gtg gca gaa ttg gag gtg ctg cgc caa cgg gag atg gcg gag     940
Thr Asp Val Ala Glu Leu Glu Val Leu Arg Gln Arg Glu Met Ala Glu
        250                 255                 260 aag aga gct cgg gcc ctc cag cga gga aac agg cac tct cga ttt ggg     988
Lys Arg Ala Arg Ala Leu Gln Arg Gly Asn Arg His Ser Arg Phe Gly
    265                 270                 275 ggc tcc tac att gtc cag ggg ttg aaa tct att ggg gag aag gat gtc    1036
Gly Ser Tyr Ile Val Gln Gly Leu Lys Ser Ile Gly Glu Lys Asp Val
280                 285                 290                 295 gtc ttt cac aaa ggc ctt cac aat ctc cag aac tac agc tca gat ctg    1084
Val Phe His Lys Gly Leu His Asn Leu Gln Asn Tyr Ser Ser Asp Leu
                300                 305                 310 gga aag cag ccc agg agg gtg ccc aag cgt cgt cag gct gcc cag gag    1132
Gly Lys Gln Pro Arg Arg Val Pro Lys Arg Arg Gln Ala Ala Gln Glu
            315                 320                 325 ctg tct gtc cat cgc cgc tct gtc ctg aat gtg aga ctc ttc ctc aga    1180
```

```
Leu Ser Val His Arg Arg Ser Val Leu Asn Val Arg Leu Phe Leu Arg
            330                 335                 340 gac ttc tgc tct gag ttc ctg gag aac tgc tac aac ccg ctc atg ggc      1228
Asp Phe Cys Ser Glu Phe Leu Glu Asn Cys Tyr Asn Pro Leu Met Gly
345                 350                 355 gcg gtc aag gat cat ctg ctt cgg gag aga gcg cag cag cat gac gag      1276
Ala Val Lys Asp His Leu Leu Arg Glu Arg Ala Gln Gln His Asp Glu
360                 365                 370                 375 act tac tac atg tgg gca atg gct ttc ttc atg gcc ttc aac cga gct      1324
Thr Tyr Tyr Met Trp Ala Met Ala Phe Phe Met Ala Phe Asn Arg Ala
                380                 385                 390 gcc acc ttc cgc ccc ggc ctt gtt tct gag acc ctc agt atc cgt acc      1372
Ala Thr Phe Arg Pro Gly Leu Val Ser Glu Thr Leu Ser Ile Arg Thr
            395                 400                 405 ttt cac ttt gtg gag cag aac ctc acc aac tac tac gag atg atg ctg      1420
Phe His Phe Val Glu Gln Asn Leu Thr Asn Tyr Tyr Glu Met Met Leu
        410                 415                 420 aca gac cgc aag gag gcc gcc tcc tgg gcg cgc agg atg cac ctg gcc      1468
Thr Asp Arg Lys Glu Ala Ala Ser Trp Ala Arg Arg Met His Leu Ala
    425                 430                 435 ctg aag gcc tac cag gag ctg ctg gcc acg gtg aac gag atg gac atg      1516
Leu Lys Ala Tyr Gln Glu Leu Leu Ala Thr Val Asn Glu Met Asp Met
440                 445                 450                 455 tgc cca gat gag gct gtt agg gag agc agt cgt atc atc aaa aac aac      1564
Cys Pro Asp Glu Ala Val Arg Glu Ser Ser Arg Ile Ile Lys Asn Asn
                460                 465                 470 att ttc tat atg atg gag tac cga gaa cta ttc ctg gcg ctc ttt cga      1612
Ile Phe Tyr Met Met Glu Tyr Arg Glu Leu Phe Leu Ala Leu Phe Arg
            475                 480                 485 aag ttt gat gag aga tac cat cca cgc tca ttc ctt cga gac ctg gtg      1660
Lys Phe Asp Glu Arg Tyr His Pro Arg Ser Phe Leu Arg Asp Leu Val
        490                 495                 500 gaa acc acc cac ctc ttc ctc aaa atg ttg gag cgc ttt tgc cgg agc      1708
Glu Thr Thr His Leu Phe Leu Lys Met Leu Glu Arg Phe Cys Arg Ser
    505                 510                 515 cgc ggg aac ctg atg gtg cag aac aaa aga aaa aag agg aaa aag aaa      1756
Arg Gly Asn Leu Met Val Gln Asn Lys Arg Lys Lys Arg Lys Lys Lys
520                 525                 530                 535 aag aag gtt cag gac cag ggt gtt gct ttc tca caa agc ccc ggg gag      1804
Lys Lys Val Gln Asp Gln Gly Val Ala Phe Ser Gln Ser Pro Gly Glu
                540                 545                 550 ctg gag gcc atg tgg cca gcc ctg gca gag cag ctg ctg cag tgt gcc      1852
Leu Glu Ala Met Trp Pro Ala Leu Ala Glu Gln Leu Leu Gln Cys Ala
            555                 560                 565 cag gac cct gag ctc agt gtg gac ccc gtc gtt ccc ttt gat gcg gcc      1900
Gln Asp Pro Glu Leu Ser Val Asp Pro Val Val Pro Phe Asp Ala Ala
        570                 575                 580 tca gag gtg cca gtg gag gag cag cgg gta gaa gcc atg gtg agg atc      1948
Ser Glu Val Pro Val Glu Glu Gln Arg Val Glu Ala Met Val Arg Ile
    585                 590                 595 caa gac tgc ctt acg gct ggc cag gcc ccg caa gcc ctg gcc ctc ctg      1996
Gln Asp Cys Leu Thr Ala Gly Gln Ala Pro Gln Ala Leu Ala Leu Leu
600                 605                 610                 615 cgg tct gcc cgg gaa gtg tgg cct gaa gga aat gcg ttt ggc tct cca      2044
Arg Ser Ala Arg Glu Val Trp Pro Glu Gly Asn Ala Phe Gly Ser Pro
                620                 625                 630 gtc att tcc cca ggg gaa gaa atg cag ttg ctg aaa caa atc ctc tcc      2092
Val Ile Ser Pro Gly Glu Glu Met Gln Leu Leu Lys Gln Ile Leu Ser
            635                 640                 645
```

```
acg ccc ctt ccc cgg cag cag gag cca gaa gaa gga gat gca gag gag      2140
Thr Pro Leu Pro Arg Gln Gln Glu Pro Glu Glu Gly Asp Ala Glu Glu
        650                 655                 660 gaa gag gaa gag gag gag gaa gag gag tta cag gtg gtc cag gtg tca      2188
Glu Glu Glu Glu Glu Glu Glu Glu Glu Leu Gln Val Val Gln Val Ser
665                 670                 675 gag aag gag ttt aac ttt ctg gaa tac ctg aaa cgc ttc gca tcc tca      2236
Glu Lys Glu Phe Asn Phe Leu Glu Tyr Leu Lys Arg Phe Ala Ser Ser
680                 685                 690                 695 acc atc gtg cgg gcc tac gtg ctt ctc ctg cgg agc tac agg cag aac      2284
Thr Ile Val Arg Ala Tyr Val Leu Leu Leu Arg Ser Tyr Arg Gln Asn
            700                 705                 710 agt gct cac acc aac cac tgc atc gcc aag atg ctg cac cgg ctg gcc      2332
Ser Ala His Thr Asn His Cys Ile Ala Lys Met Leu His Arg Leu Ala
        715                 720                 725 cat ggc ctg ggg atg gaa gcc ctg ctt ttc cag ctg tcc ctg ttc tgc      2380
His Gly Leu Gly Met Glu Ala Leu Leu Phe Gln Leu Ser Leu Phe Cys
            730                 735                 740 ctc ttc aat cgg ctg ctt agt gac cca gct gct gcg gcc tac aaa gag      2428
Leu Phe Asn Arg Leu Leu Ser Asp Pro Ala Ala Ala Ala Tyr Lys Glu
745                 750                 755 cta gtg act ttt gcc aaa tac atc att ggc aag ttc ttt gcg ttg gct      2476
Leu Val Thr Phe Ala Lys Tyr Ile Ile Gly Lys Phe Phe Ala Leu Ala
760                 765                 770                 775 gcc gtg aac cag aaa gcg ttt gtg gag ctg cta ttc tgg aag aac acc      2524
Ala Val Asn Gln Lys Ala Phe Val Glu Leu Leu Phe Trp Lys Asn Thr
            780                 785                 790 gca gtg gtt cgg gaa atg acc cag gga tat ggc tcc ctc gac agt ggg      2572
Ala Val Val Arg Glu Met Thr Gln Gly Tyr Gly Ser Leu Asp Ser Gly
        795                 800                 805 tct tcc agc cac aga gct cct ctg tgg agc cct gag gaa gag gcc cag      2620
Ser Ser Ser His Arg Ala Pro Leu Trp Ser Pro Glu Glu Glu Ala Gln
            810                 815                 820 ctt cag gaa cta tac ctc gcc cac aag gat gtg gaa ggt caa gat gta      2668
Leu Gln Glu Leu Tyr Leu Ala His Lys Asp Val Glu Gly Gln Asp Val
        825                 830                 835 gtg gaa acc ata ttg gcg cac ctg aaa gtc gtt cct cga aca cgc aag      2716
Val Glu Thr Ile Leu Ala His Leu Lys Val Val Pro Arg Thr Arg Lys
840                 845                 850                 855 cag gtc atc cac cac ctg gtc cgg atg ggc ctg gcc gac agc gtc aag      2764
Gln Val Ile His His Leu Val Arg Met Gly Leu Ala Asp Ser Val Lys
            860                 865                 870 gag ttc cag aag agg aaa ggg acc cag att gtc ttg tgg acg gag gac      2812
Glu Phe Gln Lys Arg Lys Gly Thr Gln Ile Val Leu Trp Thr Glu Asp
        875                 880                 885 cag gag ctg gag tta cag cgg ctc ttt gag gag ttc cgg gac tct gat      2860
Gln Glu Leu Glu Leu Gln Arg Leu Phe Glu Glu Phe Arg Asp Ser Asp
            890                 895                 900 gat gtt ctt ggt caa atc atg aag aat atc aca gcc aaa cgt tca cgg      2908
Asp Val Leu Gly Gln Ile Met Lys Asn Ile Thr Ala Lys Arg Ser Arg
        905                 910                 915 gct cga gta gtg gac aaa ctg ttg gcc ctg ggg ttg gtg tct gag cgg      2956
Ala Arg Val Val Asp Lys Leu Leu Ala Leu Gly Leu Val Ser Glu Arg
920                 925                 930                 935 agg cag cta tac aag aaa cgg aga aag aag ctg gcg cct tct tgc atg      3004
Arg Gln Leu Tyr Lys Lys Arg Arg Lys Lys Leu Ala Pro Ser Cys Met
            940                 945                 950 cag aat gga gaa aag tcc ccg aga gac ccc tgg cag gaa gat ccg gaa      3052
Gln Asn Gly Glu Lys Ser Pro Arg Asp Pro Trp Gln Glu Asp Pro Glu
        955                 960                 965
```

-continued

```
gag gaa gac gaa cac ttg cca gag gac gaa agt gaa gat gag gag agt        3100
Glu Glu Asp Glu His Leu Pro Glu Asp Glu Ser Glu Asp Glu Glu Ser
        970                 975                 980 gag gaa ggc ttg cca tca gga cag ggt cag ggc agc tca tct ctc tct        3148
Glu Glu Gly Leu Pro Ser Gly Gln Gly Gln Gly Ser Ser Ser Leu Ser
    985                 990                 995 gct gaa aac ctc ggt gag agc ctt cgt cag gaa ggc ctc tct gct ccc        3196
Ala Glu Asn Leu Gly Glu Ser Leu Arg Gln Glu Gly Leu Ser Ala Pro
1000                1005                1010                1015 ctc ctg tgg ctc cag agc tcc ctg atc cga gca gca aat gac cga gaa        3244
Leu Leu Trp Leu Gln Ser Ser Leu Ile Arg Ala Ala Asn Asp Arg Glu
                1020                1025                1030 gag gat ggc tgc tcc cag gca atc cct ctg gtg cct ctg aca gag gaa        3292
Glu Asp Gly Cys Ser Gln Ala Ile Pro Leu Val Pro Leu Thr Glu Glu
            1035                1040                1045 aat gag gaa gca atg gag aac gaa cag ttt cag cat ctg cta cgc aag        3340
Asn Glu Glu Ala Met Glu Asn Glu Gln Phe Gln His Leu Leu Arg Lys
        1050                1055                1060 cta ggg atc cgg ccg ccc agc tca ggg cag gaa acc ttc tgg aga att        3388
Leu Gly Ile Arg Pro Pro Ser Ser Gly Gln Glu Thr Phe Trp Arg Ile
    1065                1070                1075 cca gcc aaa ctg agc tcc acc cag ctt cgg agg gtg gct gct tct ttg        3436
Pro Ala Lys Leu Ser Ser Thr Gln Leu Arg Arg Val Ala Ala Ser Leu
1080                1085                1090                1095 agt cag caa gaa aac gag gag gaa agg gaa gag gag cca gag cca gga        3484
Ser Gln Gln Glu Asn Glu Glu Glu Arg Glu Glu Glu Pro Glu Pro Gly
                1100                1105                1110 gtc ccc gga gag cag ggt ccc agt gag gag cac cgg aca gaa gcc ctg        3532
Val Pro Gly Glu Gln Gly Pro Ser Glu Glu His Arg Thr Glu Ala Leu
            1115                1120                1125 aga gcc ctt ctg tca gcc cgt aag agg aaa gca ggc ctg ggg cct aca        3580
Arg Ala Leu Leu Ser Ala Arg Lys Arg Lys Ala Gly Leu Gly Pro Thr
        1130                1135                1140 gaa gag gag gcc act ggg gag gaa gaa tgg aac tca gcg ccc aag aag        3628
Glu Glu Glu Ala Thr Gly Glu Glu Glu Trp Asn Ser Ala Pro Lys Lys
    1145                1150                1155 cgg caa ctg ctg gac agc gac gaa gag gaa gat gat gag ggg agg agg        3676
Arg Gln Leu Leu Asp Ser Asp Glu Glu Glu Asp Asp Glu Gly Arg Arg
1160                1165                1170                1175 caa gca gtg tcg gga acg cca aga gtc cac agg aag aaa cgg ttt cag        3724
Gln Ala Val Ser Gly Thr Pro Arg Val His Arg Lys Lys Arg Phe Gln
                1180                1185                1190 att gag gat gag gat gac tgaaagccag atgtgtttga ccgatgtgag               3772
Ile Glu Asp Glu Asp Asp
            1195 ttggaggcac aaaagctact tttgcctgcg ttggaagcaa tcttctctac attgacagcc      3832 caggaatttt aggcagcagt gttgggtgga gtctttgcgg tcagtccttg ccccaggttc      3892 atcagcgtgc acagccggtc tctgggtccg tctcgtagca aatgaagagt ggcgaaaggt      3952 tcaaggtggc ttgtcctcct ctaaggactg cgtcttggct tctgacgggg agctttataa      4012 cccagcacgg ttgttcattc tgtcctcaca aagcactgga ttgctcccat tttctttctt      4072 tcatcccagg acacatgatt gaacccgttt ctacagttga gggagagctg ggatgcacca      4132 ctctcaagct gacaagcatc cctgatttgt gtttcatatt aaatgtgtac aattaacagt      4192 tgctcatctc agagcggcca gccagccatc tgttgtgtct tcggaagaac ttttaagagt      4252 aaaattaaaa gacatgtcct gaactgagct tggtagtgtg agctaatccc atcgtgtggg      4312
```

-continued

```
agacagaggc aagagaattg ccatgaggga gaggaaagag tcatatagcc ctacgcgtgg      4372
gccaataaat gtaatttaaa aaatcagctt gataataaat ataattttta aa              4424
```

<210> SEQ ID NO 2
<211> LENGTH: 1197
<212> TYPE: PRT
<213> ORGANISM: Mus musculus

<400> SEQUENCE: 2

```
Met Asp Leu Tyr Met Met Asn Cys Glu Leu Leu Ala Thr Cys Ser Ala
 1               5                  10                  15

Leu Gly Tyr Leu Glu Gly Gly Thr Tyr His Lys Glu Pro Asp Cys Leu
                20                  25                  30

Glu Ser Val Lys Asp Leu Ile Arg Tyr Leu Arg His Glu Asp Glu Thr
            35                  40                  45

Arg Asp Val Arg Gln Gln Leu Gly Ala Ala Gln Ile Leu Gln Ser Asp
        50                  55                  60

Leu Leu Pro Ile Leu Thr Gln His Arg Gln Asp Lys Pro Leu Phe Asp
65                  70                  75                  80

Ala Val Ile Arg Leu Met Val Asn Leu Thr Gln Pro Ala Leu Leu Cys
                85                  90                  95

Phe Gly Ser Val Pro Lys Asp Ser Ser Val Arg His His Phe Leu Gln
                100                 105                 110

Val Leu Thr Tyr Leu Gln Ala Tyr Lys Glu Ala Phe Ala Ser Glu Lys
            115                 120                 125

Ala Phe Gly Val Leu Ser Glu Thr Leu Tyr Glu Leu Leu Gln Leu Gly
        130                 135                 140

Trp Glu Asp Arg Gln Glu Asp Asn Leu Leu Ile Glu Arg Ile Leu
145                 150                 155                 160

Leu Leu Val Arg Asn Ile Leu His Val Pro Ala Asn Leu Glu Gln Glu
                165                 170                 175

Lys Ser Ile Asp Asp Ala Ser Ile His Asp Arg Leu Leu Trp Ala
            180                 185                 190

Ile His Leu Ser Gly Met Asp Asp Leu Leu Leu Phe Leu Ser Ser Ser
        195                 200                 205

Ser Ala Glu Gln Gln Trp Ser Leu His Val Leu Glu Ile Ile Ser Leu
    210                 215                 220

Met Phe Arg Asp Gln Thr Pro Glu Gln Leu Ala Gly Val Gly Gln Gly
225                 230                 235                 240

Arg Leu Ala Gln Glu Arg Ser Thr Asp Val Ala Glu Leu Glu Val Leu
                245                 250                 255

Arg Gln Arg Glu Met Ala Glu Lys Arg Ala Arg Ala Leu Gln Arg Gly
            260                 265                 270

Asn Arg His Ser Arg Phe Gly Gly Ser Tyr Ile Val Gln Gly Leu Lys
        275                 280                 285

Ser Ile Gly Glu Lys Asp Val Val Phe His Lys Gly Leu His Asn Leu
    290                 295                 300

Gln Asn Tyr Ser Ser Asp Leu Gly Lys Gln Pro Arg Arg Val Pro Lys
305                 310                 315                 320

Arg Arg Gln Ala Ala Gln Glu Leu Ser Val His Arg Arg Ser Val Leu
                325                 330                 335

Asn Val Arg Leu Phe Leu Arg Asp Phe Cys Ser Glu Phe Leu Glu Asn
            340                 345                 350

Cys Tyr Asn Pro Leu Met Gly Ala Val Lys Asp His Leu Leu Arg Glu
```

-continued

```
             355                 360                 365
Arg Ala Gln Gln His Asp Glu Thr Tyr Tyr Met Trp Ala Met Ala Phe
    370                 375                 380

Phe Met Ala Phe Asn Arg Ala Ala Thr Phe Arg Pro Gly Leu Val Ser
385                 390                 395                 400

Glu Thr Leu Ser Ile Arg Thr Phe His Phe Val Glu Gln Asn Leu Thr
                405                 410                 415

Asn Tyr Tyr Glu Met Met Leu Thr Asp Arg Lys Glu Ala Ala Ser Trp
            420                 425                 430

Ala Arg Arg Met His Leu Ala Leu Lys Ala Tyr Gln Glu Leu Leu Ala
        435                 440                 445

Thr Val Asn Glu Met Asp Met Cys Pro Asp Glu Ala Val Arg Glu Ser
    450                 455                 460

Ser Arg Ile Ile Lys Asn Asn Ile Phe Tyr Met Met Glu Tyr Arg Glu
465                 470                 475                 480

Leu Phe Leu Ala Leu Phe Arg Lys Phe Asp Glu Arg Tyr His Pro Arg
                485                 490                 495

Ser Phe Leu Arg Asp Leu Val Glu Thr Thr His Leu Phe Leu Lys Met
            500                 505                 510

Leu Glu Arg Phe Cys Arg Ser Arg Gly Asn Leu Met Val Gln Asn Lys
        515                 520                 525

Arg Lys Lys Arg Lys Lys Lys Lys Val Gln Asp Gln Gly Val Ala
    530                 535                 540

Phe Ser Gln Ser Pro Gly Glu Leu Glu Ala Met Trp Pro Ala Leu Ala
545                 550                 555                 560

Glu Gln Leu Leu Gln Cys Ala Gln Asp Pro Glu Leu Ser Val Asp Pro
                565                 570                 575

Val Val Pro Phe Asp Ala Ala Ser Glu Val Pro Val Glu Glu Gln Arg
            580                 585                 590

Val Glu Ala Met Val Arg Ile Gln Asp Cys Leu Thr Ala Gly Gln Ala
        595                 600                 605

Pro Gln Ala Leu Ala Leu Leu Arg Ser Ala Arg Glu Val Trp Pro Glu
    610                 615                 620

Gly Asn Ala Phe Gly Ser Pro Val Ile Ser Pro Gly Glu Glu Met Gln
625                 630                 635                 640

Leu Leu Lys Gln Ile Leu Ser Thr Pro Leu Pro Arg Gln Gln Glu Pro
                645                 650                 655

Glu Glu Gly Asp Ala Glu Glu Glu Glu Glu Glu Glu Glu
            660                 665                 670

Leu Gln Val Val Gln Val Ser Glu Lys Glu Phe Asn Phe Leu Glu Tyr
        675                 680                 685

Leu Lys Arg Phe Ala Ser Ser Thr Ile Val Arg Ala Tyr Val Leu Leu
    690                 695                 700

Leu Arg Ser Tyr Arg Gln Asn Ser Ala His Thr Asn His Cys Ile Ala
705                 710                 715                 720

Lys Met Leu His Arg Leu Ala His Gly Leu Gly Met Glu Ala Leu Leu
                725                 730                 735

Phe Gln Leu Ser Leu Phe Cys Leu Phe Asn Arg Leu Leu Ser Asp Pro
            740                 745                 750

Ala Ala Ala Ala Tyr Lys Glu Leu Val Thr Phe Ala Lys Tyr Ile Ile
        755                 760                 765

Gly Lys Phe Phe Ala Leu Ala Ala Val Asn Gln Lys Ala Phe Val Glu
    770                 775                 780
```

-continued

Leu Leu Phe Trp Lys Asn Thr Ala Val Val Arg Glu Met Thr Gln Gly
785                 790                 795                 800

Tyr Gly Ser Leu Asp Ser Gly Ser Ser Ser His Arg Ala Pro Leu Trp
            805                 810                 815

Ser Pro Glu Glu Glu Ala Gln Leu Gln Glu Leu Tyr Leu Ala His Lys
            820                 825                 830

Asp Val Glu Gly Gln Asp Val Glu Thr Ile Leu Ala His Leu Lys
            835                 840                 845

Val Val Pro Arg Thr Arg Lys Gln Val Ile His His Leu Val Arg Met
    850                 855                 860

Gly Leu Ala Asp Ser Val Lys Glu Phe Gln Lys Arg Lys Gly Thr Gln
865                 870                 875                 880

Ile Val Leu Trp Thr Glu Asp Gln Glu Leu Glu Leu Gln Arg Leu Phe
                885                 890                 895

Glu Glu Phe Arg Asp Ser Asp Asp Val Leu Gly Gln Ile Met Lys Asn
                900                 905                 910

Ile Thr Ala Lys Arg Ser Arg Ala Arg Val Val Asp Lys Leu Leu Ala
                915                 920                 925

Leu Gly Leu Val Ser Glu Arg Arg Gln Leu Tyr Lys Lys Arg Arg Lys
            930                 935                 940

Lys Leu Ala Pro Ser Cys Met Gln Asn Gly Glu Lys Ser Pro Arg Asp
945                 950                 955                 960

Pro Trp Gln Glu Asp Pro Glu Glu Glu Asp His Leu Pro Glu Asp
                965                 970                 975

Glu Ser Glu Asp Glu Glu Ser Glu Glu Gly Leu Pro Ser Gly Gln Gly
            980                 985                 990

Gln Gly Ser Ser Leu Ser Ala Glu Asn Leu Gly Glu Ser Leu Arg
            995                 1000                1005

Gln Glu Gly Leu Ser Ala Pro Leu Leu Trp Leu Gln Ser Ser Leu Ile
            1010                1015                1020

Arg Ala Ala Asn Asp Arg Glu Glu Asp Gly Cys Ser Gln Ala Ile Pro
1025                1030                1035                1040

Leu Val Pro Leu Thr Glu Glu Asn Glu Glu Ala Met Glu Asn Glu Gln
                1045                1050                1055

Phe Gln His Leu Leu Arg Lys Leu Gly Ile Arg Pro Pro Ser Ser Gly
                1060                1065                1070

Gln Glu Thr Phe Trp Arg Ile Pro Ala Lys Leu Ser Ser Thr Gln Leu
                1075                1080                1085

Arg Arg Val Ala Ala Ser Leu Ser Gln Gln Glu Asn Glu Glu Glu Arg
1090                1095                1100

Glu Glu Glu Pro Glu Pro Gly Val Pro Gly Gln Gly Pro Ser Glu
1105                1110                1115                1120

Glu His Arg Thr Glu Ala Leu Arg Ala Leu Leu Ser Ala Arg Lys Arg
                1125                1130                1135

Lys Ala Gly Leu Gly Pro Thr Gly Glu Glu Ala Thr Gly Glu Glu Glu
            1140                1145                1150

Trp Asn Ser Ala Pro Lys Lys Arg Gln Leu Leu Asp Ser Asp Glu Glu
            1155                1160                1165

Glu Asp Asp Glu Gly Arg Arg Gln Ala Val Ser Gly Thr Pro Arg Val
            1170                1175                1180

His Arg Lys Lys Arg Phe Gln Ile Glu Asp Glu Asp Asp
1185                1190                1195

<210> SEQ ID NO 3
<211> LENGTH: 1720
<212> TYPE: DNA
<213> ORGANISM: Mus musculus
<220> FEATURE:
<221> NAME/KEY: misc_feature
<222> LOCATION: (1)...(1720)
<223> OTHER INFORMATION: n = A,T,C or G

<400> SEQUENCE: 3

| | | | | | |
|---|---|---|---|---|---|
| aagctgagca | tnaaggagac | tctgccagga | tggatgagct | gngnactctt | gtttccagac | 60 |
| aatgtagcca | ccattgacgt | caatgtaagc | gaggaaacaa | aaggcccttt | gggtgtgtgc | 120 |
| agggtgcagc | ttggcccagc | tctgctcagt | gtttgtgtgt | gttggggagt | gtggtgaggt | 180 |
| gtcagtgtca | gaggaaccag | aggtgctgcc | ctgcccctg  | cagtgtgagt | caacatctgg | 240 |
| cttcccaggg | cttctttgga | aagggctgct | gaaatgaact | tagtctctgc | ccccatctgc | 300 |
| atctgangaa | ttgcatgcct | gtcctgccag | gcagacagaa | agaagtagct | cccacacgga | 360 |
| attcttgaat | gtgggttagc | cggctgtgta | caccagcagc | tcagtttgtt | agcagacttc | 420 |
| tgttgctaat | gtttgcctcc | tttccattcc | tggttcctag | gacacccag  | gggaagattc | 480 |
| agagtagtgg | atgctactag | gcttcaagtt | ccctggcaat | gacaaatgac | cttttttaccc | 540 |
| ttggaagacg | tgacaagctt | gccttctcca | tcacaccttg | catgagtctt | taggttgttc | 600 |
| tctgtcagcc | tcaaacccgc | tccgaggaaa | cttctactcc | ctcctttgac | cctttggaca | 660 |
| ggagcctgaa | cgcttttagta | ggcttccaga | cagtgctctt | gaaagaacca | aatagcttca | 720 |
| accaaggttc | cacaggggca | gggctgtcct | atcactggag | gagtaccctc | ccctgactag | 780 |
| ctagtgtctg | tagcttccac | ttcagaawag | ccctgmtgtt | ccagatgcac | accccgctt  | 840 |
| ccatagttcc | tgtaaggtta | ataaactaca | ccaccgcatt | tggttaagct | tccctgtaga | 900 |
| acgtcagtct | tctctcccta | tgtgattgag | ggcaggaaga | aatcacttct | ttcctttgta | 960 |
| tctctgcacg | gcaattatga | ccttatttcc | tgaatcaaca | ctaactagca | agacgcagtt | 1020 |
| tcagaaacaa | gaaaggctaa | gtgggagttt | tgtgctttgg | cccatctgga | atgacggtca | 1080 |
| gcctgggggg | cctgtcctag | ggtcacccag | cctgtcctgg | gaaggtgctc | agcagcagat | 1140 |
| ccagaggggc | cgtcctatt  | gtcctcaagc | gtctcgccat | gaatgaatga | gaggggaaat | 1200 |
| gaatgaactg | ggctggatga | gcgaaaggtg | tcagcagaga | gcattctcgg | tccttcggat | 1260 |
| taccgaggct | ggtcacgtcg | tcgcaggtga | taggccgggg | gccctgtctc | tgccggctgt | 1320 |
| gagttgcgca | gcggccaagc | accattcccc | cgcgccgcag | tggtacgcgc | cactccgggg | 1380 |
| ctgcacgagc | gggccaccgc | cgtgccaggt | gaatggaagt | cccgcaggcc | ggaagtggac | 1440 |
| gagcctactc | gcccgggcgc | ggggggggcgc | aagagcgcgc | agcatcttca | ttgaggaacc | 1500 |
| cgggcggcga | acatggagtt | ccatgtgcgt | cttatgtaaa | gagagcgacg | ggcgtctcca | 1560 |
| ccaattgacg | agcgtagctc | tcaggttccg | ccccgccagt | atgcaaatga | ggtggcactc | 1620 |
| cgaccaatgg | cgcgcgcagg | ggcgggctca | gcgcgcgcgg | tcacgttttt | ccactatgtg | 1680 |
| acagcggagg | gcgacgcggc | ggcagcggcg | ctaactagtg | | | 1720 |

<210> SEQ ID NO 4
<211> LENGTH: 2450
<212> TYPE: DNA
<213> ORGANISM: Mus musculus
<220> FEATURE:
<221> NAME/KEY: CDS
<222> LOCATION: (20)...(1837)

-continued

```
<400> SEQUENCE: 4
gacccgccgc gccccgagc atg ggg gtg aac gcc gtg cac tgg ttc cgg aag          52
                    Met Gly Val Asn Ala Val His Trp Phe Arg Lys
                     1               5                  10 gga ctc cgg ctc cac gac aac ccc gcc ctg aag gag tgc atc cag ggc          100
Gly Leu Arg Leu His Asp Asn Pro Ala Leu Lys Glu Cys Ile Gln Gly
         15                  20                  25 gcc gac acc atc cgc tgc gtc tat atc ctc gac ccc tgg ttc gcc ggc          148
Ala Asp Thr Ile Arg Cys Val Tyr Ile Leu Asp Pro Trp Phe Ala Gly
     30                  35                  40 tct tcc aac gtg ggc atc aac agg tgg cga ttt ttg ctt cag tgt ctt          196
Ser Ser Asn Val Gly Ile Asn Arg Trp Arg Phe Leu Leu Gln Cys Leu
 45                  50                  55 gag gat ctt gat gcc aat cta cga aaa tta aat tct cgt ctg ttt gtg          244
Glu Asp Leu Asp Ala Asn Leu Arg Lys Leu Asn Ser Arg Leu Phe Val
 60                  65                  70                  75 att cgg gga cag cca gct gat gta ttt ccc agg ctt ttc aag gaa tgg          292
Ile Arg Gly Gln Pro Ala Asp Val Phe Pro Arg Leu Phe Lys Glu Trp
             80                  85                  90 aac atc act aaa ctc tca att gag tat gat tct gag cct ttt ggg aag          340
Asn Ile Thr Lys Leu Ser Ile Glu Tyr Asp Ser Glu Pro Phe Gly Lys
             95                 100                 105 gaa cga gat gca gct atc aag aag ctg gct act gag gct ggc gtg gaa          388
Glu Arg Asp Ala Ala Ile Lys Lys Leu Ala Thr Glu Ala Gly Val Glu
        110                 115                 120 gtc atc gtg cgc att tca cat aca ctg tat gac ctg gac aag atc ata          436
Val Ile Val Arg Ile Ser His Thr Leu Tyr Asp Leu Asp Lys Ile Ile
    125                 130                 135 gaa ctc aat ggc gga cag cca cct cta aca tat aaa agg ttt cag act          484
Glu Leu Asn Gly Gly Gln Pro Pro Leu Thr Tyr Lys Arg Phe Gln Thr
140                 145                 150                 155 ctc gtc agc aag atg gag cca ctg gag atg cca gca gac acc atc aca          532
Leu Val Ser Lys Met Glu Pro Leu Glu Met Pro Ala Asp Thr Ile Thr
                160                 165                 170 tca gat gtg ata gga aag tgc atg acc cct ctg tct gat gac cat gat          580
Ser Asp Val Ile Gly Lys Cys Met Thr Pro Leu Ser Asp Asp His Asp
            175                 180                 185 gag aaa tat ggc gtt cct tcc ctg gaa gag ctc ggc ttt gat aca gat          628
Glu Lys Tyr Gly Val Pro Ser Leu Glu Glu Leu Gly Phe Asp Thr Asp
        190                 195                 200 ggc ctg tcc tct gca gtg tgg cca gga gga gaa act gag gca ctt aca          676
Gly Leu Ser Ser Ala Val Trp Pro Gly Gly Glu Thr Glu Ala Leu Thr
    205                 210                 215 cgt ttg gaa agg cat ttg gaa aga aag gcc tgg gtg gca aac ttt gaa          724
Arg Leu Glu Arg His Leu Glu Arg Lys Ala Trp Val Ala Asn Phe Glu
220                 225                 230                 235 cga cct cga atg aat gca aac tcc ctg ctt gca agc cca act gga ctc          772
Arg Pro Arg Met Asn Ala Asn Ser Leu Leu Ala Ser Pro Thr Gly Leu
                240                 245                 250 agt cct tat ctc cgc ttt ggt tgt tta tca tgt cgg ctg ttt tat ttc          820
Ser Pro Tyr Leu Arg Phe Gly Cys Leu Ser Cys Arg Leu Phe Tyr Phe
            255                 260                 265 aaa cta aca gat ctc tac aaa aag gta aag aag aat agt tcc cct ccc          868
Lys Leu Thr Asp Leu Tyr Lys Lys Val Lys Lys Asn Ser Ser Pro Pro
        270                 275                 280 ctt tct ctt tat ggg caa ctc ctg tgg cgt gaa ttt ttt tat aca gca          916
Leu Ser Leu Tyr Gly Gln Leu Leu Trp Arg Glu Phe Phe Tyr Thr Ala
    285                 290                 295 gcc aca aac aac cca cgc ttt gac aaa atg gaa ggg aac ccc atc tgt          964
```

```
Ala Thr Asn Asn Pro Arg Phe Asp Lys Met Glu Gly Asn Pro Ile Cys
300                 305                 310                 315 gtt cag atc cct tgg gac aag aac ccc gag gct ctg gcc aaa tgg gca      1012
Val Gln Ile Pro Trp Asp Lys Asn Pro Glu Ala Leu Ala Lys Trp Ala
                320                 325                 330 gaa ggc cgg aca ggc ttc ccg tgg att gac gcc atc atg act cag ctt      1060
Glu Gly Arg Thr Gly Phe Pro Trp Ile Asp Ala Ile Met Thr Gln Leu
            335                 340                 345 cgt cag gag ggc tgg atc cac cat tta gcc aga cac gcg gtt gcc tgt      1108
Arg Gln Glu Gly Trp Ile His His Leu Ala Arg His Ala Val Ala Cys
        350                 355                 360 ttc ctg act cgt ggt gac ctg tgg atc agc tgg gaa gaa ggg atg aag      1156
Phe Leu Thr Arg Gly Asp Leu Trp Ile Ser Trp Glu Glu Gly Met Lys
    365                 370                 375 gtc ttt gaa gag tta ctg ctt gat gca gat tgg agc ata aat gct gga      1204
Val Phe Glu Glu Leu Leu Leu Asp Ala Asp Trp Ser Ile Asn Ala Gly
380                 385                 390                 395 agt tgg atg tgg ctg tcc tgc agt tcc ttt ttt cag caa ttt ttt cac      1252
Ser Trp Met Trp Leu Ser Cys Ser Ser Phe Phe Gln Gln Phe Phe His
                400                 405                 410 tgc tac tgc cct gtg ggt ttt ggt agg agg aca gat ccc aat gga gac      1300
Cys Tyr Cys Pro Val Gly Phe Gly Arg Arg Thr Asp Pro Asn Gly Asp
            415                 420                 425 tat att agg cgt tat tta cct gtc cta aga ggc ttc cct gca aaa tat      1348
Tyr Ile Arg Arg Tyr Leu Pro Val Leu Arg Gly Phe Pro Ala Lys Tyr
        430                 435                 440 atc tac gat cct tgg aat gca cca gaa ggc atc cag aag gtt gcc aag      1396
Ile Tyr Asp Pro Trp Asn Ala Pro Glu Gly Ile Gln Lys Val Ala Lys
    445                 450                 455 tgt ttg ata gga gtt aat tac ccc aaa ccg atg gtg aac cat gct gag      1444
Cys Leu Ile Gly Val Asn Tyr Pro Lys Pro Met Val Asn His Ala Glu
460                 465                 470                 475 gca agc aga ctg aat att gaa aga atg aag cag atc tat cag cag ctt      1492
Ala Ser Arg Leu Asn Ile Glu Arg Met Lys Gln Ile Tyr Gln Gln Leu
                480                 485                 490 tcc cgg tac aga ggg cta ggt ctt ctc gcc tcg gtc cct tct aac tct      1540
Ser Arg Tyr Arg Gly Leu Gly Leu Leu Ala Ser Val Pro Ser Asn Ser
            495                 500                 505 aat ggg aat gga ggg ctc atg ggc tat gct cct gga gag aat gtc ccg      1588
Asn Gly Asn Gly Gly Leu Met Gly Tyr Ala Pro Gly Glu Asn Val Pro
        510                 515                 520 agt tgt agc agc agc ggg aat gga ggg ctc atg ggc tat gct cct gga      1636
Ser Cys Ser Ser Ser Gly Asn Gly Gly Leu Met Gly Tyr Ala Pro Gly
    525                 530                 535 gag aac gtc ccg agc tgt agc ggt gga aat tgc tct caa gga agt ggt      1684
Glu Asn Val Pro Ser Cys Ser Gly Gly Asn Cys Ser Gln Gly Ser Gly
540                 545                 550                 555 att tta cac tat gct cac ggg gac agt cag cag act cac tca ctc aag      1732
Ile Leu His Tyr Ala His Gly Asp Ser Gln Gln Thr His Ser Leu Lys
                560                 565                 570 caa ggg aga agc tcc gcg ggc acc ggc ctc agc agt ggg aag cgt cct      1780
Gln Gly Arg Ser Ser Ala Gly Thr Gly Leu Ser Ser Gly Lys Arg Pro
            575                 580                 585 agt cag gaa gag gat gcc cag agt gtc ggc ccc aaa gtc cag cgg cag      1828
Ser Gln Glu Glu Asp Ala Gln Ser Val Gly Pro Lys Val Gln Arg Gln
        590                 595                 600 agc agt aac tgatacgaaa gcgtgtggga ggagtccttg caactgaagt              1877
Ser Ser Asn
        605
```

-continued

```
tggtgggaaa gtcagtactt ttcatttaaa ttatttaaaa atgtcattca ttcatgggaa   1937
acagttacat ttcaaacatt atttctaata atatttctgt ggttttttaac ttttttaatga   1997 atgtcatata ggacaagtgg taatttgtat ataagatctt ggtaagagat ttgcttaatg   2057
taaatataag ccacagttag aatagactca tcagtatatt tttgataatt tttcatgtat   2117
ggtaaaagtt aaagttaaca gatattctga tataaatctc aagagttttg agagtcattg   2177
caggaaaatg ggaagttttt aaactttctt aaaagacttt gttaaaattt tagggcacat   2237
ttttccagac atcagtgttt gatctaattt tgcagtcttt gataataatg ctttagagaa   2297
tacatgtaat caagtgcata ggcctctgtc agcgagggcc atctgtgtta cagcctcctg   2357
acttgcgcag tgcattgtgc cgtgctcctt tgtctctccg cctctttatt tacatctacc   2417
gtgactttgt tattaaagta tatgcaaata tgg                                2450
```

<210> SEQ ID NO 5
<211> LENGTH: 606
<212> TYPE: PRT
<213> ORGANISM: Mus musculus

<400> SEQUENCE: 5

```
Met Gly Val Asn Ala Val His Trp Phe Arg Lys Gly Leu Arg Leu His
 1               5                  10                  15

Asp Asn Pro Ala Leu Lys Glu Cys Ile Gln Gly Ala Asp Thr Ile Arg
            20                  25                  30

Cys Val Tyr Ile Leu Asp Pro Trp Phe Ala Gly Ser Ser Asn Val Gly
        35                  40                  45

Ile Asn Arg Trp Arg Phe Leu Leu Gln Cys Leu Glu Asp Leu Asp Ala
    50                  55                  60

Asn Leu Arg Lys Leu Asn Ser Arg Leu Phe Val Ile Arg Gly Gln Pro
65                  70                  75                  80

Ala Asp Val Phe Pro Arg Leu Phe Lys Glu Trp Asn Ile Thr Lys Leu
                85                  90                  95

Ser Ile Glu Tyr Asp Ser Glu Pro Phe Gly Lys Glu Arg Asp Ala Ala
            100                 105                 110

Ile Lys Lys Leu Ala Thr Glu Ala Gly Val Glu Val Ile Val Arg Ile
        115                 120                 125

Ser His Thr Leu Tyr Asp Leu Asp Lys Ile Ile Glu Leu Asn Gly Gly
    130                 135                 140

Gln Pro Pro Leu Thr Tyr Lys Arg Phe Gln Thr Leu Val Ser Lys Met
145                 150                 155                 160

Glu Pro Leu Glu Met Pro Ala Asp Thr Ile Thr Ser Asp Val Ile Gly
                165                 170                 175

Lys Cys Met Thr Pro Leu Ser Asp Asp His Asp Glu Lys Tyr Gly Val
            180                 185                 190

Pro Ser Leu Glu Glu Leu Gly Phe Asp Thr Asp Gly Leu Ser Ser Ala
        195                 200                 205

Val Trp Pro Gly Gly Glu Thr Glu Ala Leu Thr Arg Leu Glu Arg His
    210                 215                 220

Leu Glu Arg Lys Ala Trp Val Ala Asn Phe Glu Arg Pro Arg Met Asn
225                 230                 235                 240

Ala Asn Ser Leu Leu Ala Ser Pro Thr Gly Leu Ser Pro Tyr Leu Arg
                245                 250                 255

Phe Gly Cys Leu Ser Cys Arg Leu Phe Tyr Phe Lys Leu Thr Asp Leu
            260                 265                 270
```

```
Tyr Lys Lys Val Lys Lys Asn Ser Ser Pro Leu Ser Leu Tyr Gly
            275                 280                 285

Gln Leu Leu Trp Arg Glu Phe Phe Tyr Thr Ala Ala Thr Asn Asn Pro
        290                 295                 300

Arg Phe Asp Lys Met Glu Gly Asn Pro Ile Cys Val Gln Ile Pro Trp
305                 310                 315                 320

Asp Lys Asn Pro Glu Ala Leu Ala Lys Trp Ala Glu Gly Arg Thr Gly
                325                 330                 335

Phe Pro Trp Ile Asp Ala Ile Met Thr Gln Leu Arg Gln Glu Gly Trp
            340                 345                 350

Ile His His Leu Ala Arg His Ala Val Ala Cys Phe Leu Thr Arg Gly
            355                 360                 365

Asp Leu Trp Ile Ser Trp Glu Glu Gly Met Lys Val Phe Glu Glu Leu
370                 375                 380

Leu Leu Asp Ala Asp Trp Ser Ile Asn Ala Gly Ser Trp Met Trp Leu
385                 390                 395                 400

Ser Cys Ser Ser Phe Phe Gln Gln Phe Phe His Cys Tyr Cys Pro Val
                405                 410                 415

Gly Phe Gly Arg Arg Thr Asp Pro Asn Gly Asp Tyr Ile Arg Arg Tyr
                420                 425                 430

Leu Pro Val Leu Arg Gly Phe Pro Ala Lys Tyr Ile Tyr Asp Pro Trp
            435                 440                 445

Asn Ala Pro Glu Gly Ile Gln Lys Val Ala Lys Cys Leu Ile Gly Val
450                 455                 460

Asn Tyr Pro Lys Pro Met Val Asn His Ala Glu Ala Ser Arg Leu Asn
465                 470                 475                 480

Ile Glu Arg Met Lys Gln Ile Tyr Gln Gln Leu Ser Arg Tyr Arg Gly
                485                 490                 495

Leu Gly Leu Leu Ala Ser Val Pro Ser Asn Ser Asn Gly Asn Gly Gly
                500                 505                 510

Leu Met Gly Tyr Ala Pro Gly Glu Asn Val Pro Ser Cys Ser Ser Ser
            515                 520                 525

Gly Asn Gly Gly Leu Met Gly Tyr Ala Pro Gly Glu Asn Val Pro Ser
530                 535                 540

Cys Ser Gly Gly Asn Cys Ser Gln Gly Ser Gly Ile Leu His Tyr Ala
545                 550                 555                 560

His Gly Asp Ser Gln Gln Thr His Ser Leu Lys Gln Gly Arg Ser Ser
                565                 570                 575

Ala Gly Thr Gly Leu Ser Ser Gly Lys Arg Pro Ser Gln Glu Glu Asp
            580                 585                 590

Ala Gln Ser Val Gly Pro Lys Val Gln Arg Gln Ser Ser Asn
            595                 600                 605

<210> SEQ ID NO 6
<211> LENGTH: 1710
<212> TYPE: DNA
<213> ORGANISM: Mus musculus
<220> FEATURE:
<221> NAME/KEY: CDS
<222> LOCATION: (1)...(1707)

<400> SEQUENCE: 6 gtg cac tgg ttc cgg aag gga cta cgg ctc cac gac aac ccc gcg ctg      48
Val His Trp Phe Arg Lys Gly Leu Arg Leu His Asp Asn Pro Ala Leu
 1               5                  10                  15 cta gct gcc gtg cgc ggg gcg cgc tgt gtg cgc tgc gtc tac atc ctc      96
```

```
                Leu Ala Ala Val Arg Gly Ala Arg Cys Val Arg Cys Val Tyr Ile Leu
                                20                  25                  30 gac ccg tgg ttc gcg gcc tcc tcg tct gtg ggc atc aac cga tgg agg       144
Asp Pro Trp Phe Ala Ala Ser Ser Ser Val Gly Ile Asn Arg Trp Arg
            35                  40                  45 ttc cta ctg caa tct ctg gaa gat ctg gac aca agc tta aga aag ctg       192
Phe Leu Leu Gln Ser Leu Glu Asp Leu Asp Thr Ser Leu Arg Lys Leu
    50                  55                  60 aat tcg cgt ctg ttt gta gtc cgg gga cag cca gct gat gtg ttc cca       240
Asn Ser Arg Leu Phe Val Val Arg Gly Gln Pro Ala Asp Val Phe Pro
65                  70                  75                  80 agg ctg ttc aag gaa tgg ggg gtg acc cgt ttg acc ttt gaa tat gac       288
Arg Leu Phe Lys Glu Trp Gly Val Thr Arg Leu Thr Phe Glu Tyr Asp
                85                  90                  95 tct gaa ccc ttt ggg aaa gaa cgg gat gca gcc att atg aag atg gcc       336
Ser Glu Pro Phe Gly Lys Glu Arg Asp Ala Ala Ile Met Lys Met Ala
            100                 105                 110 aag gag gct ggc gtg gag gtg gtg act gag aac tct cac acc ctc tat       384
Lys Glu Ala Gly Val Glu Val Val Thr Glu Asn Ser His Thr Leu Tyr
        115                 120                 125 gac cta gac aga atc atc gaa ctg aat ggg cag aaa cca ccc ctt acc       432
Asp Leu Asp Arg Ile Ile Glu Leu Asn Gly Gln Lys Pro Pro Leu Thr
130                 135                 140 tac aag cgc ttt cag gcc ctc atc agc cgc atg gag ctg ccc aag aag       480
Tyr Lys Arg Phe Gln Ala Leu Ile Ser Arg Met Glu Leu Pro Lys Lys
145                 150                 155                 160 ccc gcg gtg gct gtg agc agc agc aga atg gag agc tgc aga gct gag       528
Pro Ala Val Ala Val Ser Ser Ser Arg Met Glu Ser Cys Arg Ala Glu
                165                 170                 175 atc cag aag aac cat gac gac acc tat ggc gtg cct tcc ctg gag gag       576
Ile Gln Lys Asn His Asp Asp Thr Tyr Gly Val Pro Ser Leu Glu Glu
            180                 185                 190 ctg gga ttc ccc acg gaa gga ctt ggc cca gct gtt tgg caa gga gga       624
Leu Gly Phe Pro Thr Glu Gly Leu Gly Pro Ala Val Trp Gln Gly Gly
        195                 200                 205 gag aca gaa gct ctg gcc cgc ctg gac aag cac ttg gaa cgg aag gcc       672
Glu Thr Glu Ala Leu Ala Arg Leu Asp Lys His Leu Glu Arg Lys Ala
210                 215                 220 tgg gtt gcc aac tat gag aga cct cgg atg aat gcc aat tcc tta ctg       720
Trp Val Ala Asn Tyr Glu Arg Pro Arg Met Asn Ala Asn Ser Leu Leu
225                 230                 235                 240 gcc agc ccc aca ggc ctc agc ccc tac ctg cgc ttt gga tgc ctc tcc       768
Ala Ser Pro Thr Gly Leu Ser Pro Tyr Leu Arg Phe Gly Cys Leu Ser
                245                 250                 255 tgc cgc ctc ttc tac tac cgc ctg tgg gac ttg tac aag aag gtg aag       816
Cys Arg Leu Phe Tyr Tyr Arg Leu Trp Asp Leu Tyr Lys Lys Val Lys
            260                 265                 270 agg aac agc aca ccc ccc ctc tcc tta ttt gga caa ctc ctg tgg cga       864
Arg Asn Ser Thr Pro Pro Leu Ser Leu Phe Gly Gln Leu Leu Trp Arg
        275                 280                 285 gaa ttc ttc tac aca gcg gcc acc aac aac ccc agg ttt gac cga gtg       912
Glu Phe Phe Tyr Thr Ala Ala Thr Asn Asn Pro Arg Phe Asp Arg Val
290                 295                 300 gag ggg aac ccc atc tgc atc cag atc ccc tgg gac cgc aac ccc gaa       960
Glu Gly Asn Pro Ile Cys Ile Gln Ile Pro Trp Asp Arg Asn Pro Glu
305                 310                 315                 320 gcc ctg gcc aag tgg gcc gag ggc aag aca ggc ttc cct tgg att gac      1008
Ala Leu Ala Lys Trp Ala Glu Gly Lys Thr Gly Phe Pro Trp Ile Asp
                325                 330                 335
```

```
gcc atc atg acc caa ctg agg cag gag ggc tgg atc cac cac ctg gcc       1056
Ala Ile Met Thr Gln Leu Arg Gln Glu Gly Trp Ile His His Leu Ala
            340                 345                 350 cgg cac gct gtg gcc tgc ttc ctc acc cgg ggg gac ctc tgg gtc agc       1104
Arg His Ala Val Ala Cys Phe Leu Thr Arg Gly Asp Leu Trp Val Ser
        355                 360                 365 tgg gag agc ggg gtc cgg gta ttt gac gag ctc ctc ctg gat gcc gat       1152
Trp Glu Ser Gly Val Arg Val Phe Asp Glu Leu Leu Leu Asp Ala Asp
    370                 375                 380 ttc agt gtg aat gca ggc agc tgg atg tgg ctg tcc tgc agt gct ttc       1200
Phe Ser Val Asn Ala Gly Ser Trp Met Trp Leu Ser Cys Ser Ala Phe
385                 390                 395                 400 ttc caa caa ttc ttc cac tgc tac tgc cct gtg ggc ttc ggc cga cgt       1248
Phe Gln Gln Phe Phe His Cys Tyr Cys Pro Val Gly Phe Gly Arg Arg
                405                 410                 415 aca gac ccc agt ggg gac tac atc cgg cgg tac ctg ccc aaa ctg aaa       1296
Thr Asp Pro Ser Gly Asp Tyr Ile Arg Arg Tyr Leu Pro Lys Leu Lys
            420                 425                 430 ggc ttc ccc tct cga tac atc tat gag ccc tgg aat gcc ccc gag tca       1344
Gly Phe Pro Ser Arg Tyr Ile Tyr Glu Pro Trp Asn Ala Pro Glu Ser
        435                 440                 445 gtt cag aag gct gcc aag tgc atc att ggc gtg gac tac cca cgg ccc       1392
Val Gln Lys Ala Ala Lys Cys Ile Ile Gly Val Asp Tyr Pro Arg Pro
    450                 455                 460 atc gtc aat cat gca gag act agt cgg ctc aac att gaa cga atg aag       1440
Ile Val Asn His Ala Glu Thr Ser Arg Leu Asn Ile Glu Arg Met Lys
465                 470                 475                 480 cag atc tac caa cag ctg tcg aga tac cgg gga ctc tgt cta ttg gca       1488
Gln Ile Tyr Gln Gln Leu Ser Arg Tyr Arg Gly Leu Cys Leu Leu Ala
                485                 490                 495 tct gtc cct tcc tgt gtg gaa gac ctc agt cac cct gtg gca gag cct       1536
Ser Val Pro Ser Cys Val Glu Asp Leu Ser His Pro Val Ala Glu Pro
            500                 505                 510 ggt tca agc caa gct ggg agc atc agc aac aca ggc ccc aga gca cta       1584
Gly Ser Ser Gln Ala Gly Ser Ile Ser Asn Thr Gly Pro Arg Ala Leu
        515                 520                 525 tcc agt ggc cca gct tcc ccc aaa cgc aag ctg gaa gca gcc gag gaa       1632
Ser Ser Gly Pro Ala Ser Pro Lys Arg Lys Leu Glu Ala Ala Glu Glu
    530                 535                 540 cct cct ggt gaa gaa ctg acc aag cgg gct aga gtg acg gag atg cct       1680
Pro Pro Gly Glu Glu Leu Thr Lys Arg Ala Arg Val Thr Glu Met Pro
545                 550                 555                 560 acc caa gag cca gca agc aag gac tcc tga                               1710
Thr Gln Glu Pro Ala Ser Lys Asp Ser
                565
```

<210> SEQ ID NO 7
<211> LENGTH: 569
<212> TYPE: PRT
<213> ORGANISM: Mus musculus

<400> SEQUENCE: 7

```
Val His Trp Phe Arg Lys Gly Leu Arg Leu His Asp Asn Pro Ala Leu
 1               5                  10                  15

Leu Ala Ala Val Arg Gly Ala Arg Cys Val Arg Cys Val Tyr Ile Leu
            20                  25                  30

Asp Pro Trp Phe Ala Ala Ser Ser Val Gly Ile Asn Arg Trp Arg
        35                  40                  45

Phe Leu Leu Gln Ser Leu Glu Asp Leu Asp Thr Ser Leu Arg Lys Leu
    50                  55                  60
```

```
Asn Ser Arg Leu Phe Val Val Arg Gly Gln Pro Ala Asp Val Phe Pro
 65                  70                  75                  80

Arg Leu Phe Lys Glu Trp Gly Val Thr Arg Leu Thr Phe Glu Tyr Asp
                 85                  90                  95

Ser Glu Pro Phe Gly Lys Glu Arg Asp Ala Ala Ile Met Lys Met Ala
            100                 105                 110

Lys Glu Ala Gly Val Glu Val Thr Glu Asn Ser His Thr Leu Tyr
        115                 120                 125

Asp Leu Asp Arg Ile Ile Glu Leu Asn Gly Gln Lys Pro Pro Leu Thr
    130                 135                 140

Tyr Lys Arg Phe Gln Ala Leu Ile Ser Arg Met Glu Leu Pro Lys Lys
145                 150                 155                 160

Pro Ala Val Ala Val Ser Ser Arg Met Glu Ser Cys Arg Ala Glu
                165                 170                 175

Ile Gln Lys Asn His Asp Asp Thr Tyr Gly Val Pro Ser Leu Glu Glu
            180                 185                 190

Leu Gly Phe Pro Thr Glu Gly Leu Gly Pro Ala Val Trp Gln Gly Gly
        195                 200                 205

Glu Thr Glu Ala Leu Ala Arg Leu Asp Lys His Leu Glu Arg Lys Ala
    210                 215                 220

Trp Val Ala Asn Tyr Glu Arg Pro Arg Met Asn Ala Asn Ser Leu Leu
225                 230                 235                 240

Ala Ser Pro Thr Gly Leu Ser Pro Tyr Leu Arg Phe Gly Cys Leu Ser
                245                 250                 255

Cys Arg Leu Phe Tyr Tyr Arg Leu Trp Asp Leu Tyr Lys Lys Val Lys
            260                 265                 270

Arg Asn Ser Thr Pro Pro Leu Ser Leu Phe Gly Gln Leu Leu Trp Arg
        275                 280                 285

Glu Phe Phe Tyr Thr Ala Ala Thr Asn Asn Pro Arg Phe Asp Arg Val
    290                 295                 300

Glu Gly Asn Pro Ile Cys Ile Gln Ile Pro Trp Asp Arg Asn Pro Glu
305                 310                 315                 320

Ala Leu Ala Lys Trp Ala Glu Gly Lys Thr Gly Phe Pro Trp Ile Asp
                325                 330                 335

Ala Ile Met Thr Gln Leu Arg Gln Glu Gly Trp Ile His His Leu Ala
            340                 345                 350

Arg His Ala Val Ala Cys Phe Leu Thr Arg Gly Asp Leu Trp Val Ser
        355                 360                 365

Trp Glu Ser Gly Val Arg Val Phe Asp Glu Leu Leu Leu Asp Ala Asp
    370                 375                 380

Phe Ser Val Asn Ala Gly Ser Trp Met Trp Leu Ser Cys Ser Ala Phe
385                 390                 395                 400

Phe Gln Gln Phe Phe His Cys Tyr Cys Pro Val Gly Phe Gly Arg Arg
                405                 410                 415

Thr Asp Pro Ser Gly Asp Tyr Ile Arg Arg Tyr Leu Pro Lys Leu Lys
            420                 425                 430

Gly Phe Pro Ser Arg Tyr Ile Tyr Glu Pro Trp Asn Ala Pro Glu Ser
        435                 440                 445

Val Gln Lys Ala Ala Lys Cys Ile Ile Gly Val Asp Tyr Pro Arg Pro
    450                 455                 460

Ile Val Asn His Ala Glu Thr Ser Arg Leu Asn Ile Glu Arg Met Lys
465                 470                 475                 480
```

```
Gln Ile Tyr Gln Gln Leu Ser Arg Tyr Arg Gly Leu Cys Leu Leu Ala
                485                 490                 495
Ser Val Pro Ser Cys Val Glu Asp Leu Ser His Pro Val Ala Glu Pro
            500                 505                 510
Gly Ser Ser Gln Ala Gly Ser Ile Ser Asn Thr Gly Pro Arg Ala Leu
        515                 520                 525
Ser Ser Gly Pro Ala Ser Pro Lys Arg Lys Leu Glu Ala Ala Glu Glu
    530                 535                 540
Pro Pro Gly Glu Glu Leu Thr Lys Arg Ala Arg Val Thr Glu Met Pro
545                 550                 555                 560
Thr Gln Glu Pro Ala Ser Lys Asp Ser
                565

<210> SEQ ID NO 8
<211> LENGTH: 4863
<212> TYPE: DNA
<213> ORGANISM: Mus musculus
<220> FEATURE:
<221> NAME/KEY: CDS
<222> LOCATION: (358)...(3696)
<221> NAME/KEY: misc_feature
<222> LOCATION: (1)...(4863)
<223> OTHER INFORMATION: n = A,T,C or G

<400> SEQUENCE: 8
cccgcacggc cgggcgctgc tgcccctgcc ttctgcctgg tcacgccgga cgttgctctc      60
tgaggtgttt ctcgatgctc gccggcttcc cagcaaggac ggtggaaaag ttgttgcagg     120
ctgaccgcgc tccctgagag ccccgctggt ggtccgtcca gccagcttcc gccatcgagc     180
tgtcgctgta gctcgtcacc ccagcagagt ctgtggaaat gctgaggaga aaagtgcccc     240
tcagatgagc gtggtcggcg accagtcttt cccgaaggcg atggcaggga ccaaaacaag     300
ccgggtttgg ttgctagctg caaactgaga gaagcaggct gagggctgcc aggcggg atg     360
                                                                 Met
                                                                  1 gat ccc tgt gga gac ccg gca gta cct ggt ggc gac tgt ccc cag act       408
Asp Pro Cys Gly Asp Pro Ala Val Pro Gly Gly Asp Cys Pro Gln Thr
             5                  10                  15 agg gga ccg ggg ctc cag ggg gcg tct ggc cag gag ggt cct ctg cag       456
Arg Gly Pro Gly Leu Gln Gly Ala Ser Gly Gln Glu Gly Pro Leu Gln
         20                  25                  30 ggc act tgc gtg gac agc agc cac agt gaa cac gaa gac cga aac aga       504
Gly Thr Cys Val Asp Ser Ser His Ser Glu His Glu Asp Arg Asn Arg
     35                  40                  45 atg tct gaa gag ctt ata atg gtt gtc caa gaa atg aaa aag tat ttc       552
Met Ser Glu Glu Leu Ile Met Val Val Gln Glu Met Lys Lys Tyr Phe
 50                  55                  60                  65 cca gcc gag agg cac act aag ccc agt acc cta gat gct ctt aac tat       600
Pro Ala Glu Arg His Thr Lys Pro Ser Thr Leu Asp Ala Leu Asn Tyr
                 70                  75                  80 gcc ctg cgc tgt gta cac agt gtg caa gca aac agt gac ttt ttc cag       648
Ala Leu Arg Cys Val His Ser Val Gln Ala Asn Ser Asp Phe Phe Gln
             85                  90                  95 agt ctc ggt cca cgc gga gca cac cag gca gat gtg act gta tac agt       696
Ser Leu Gly Pro Arg Gly Ala His Gln Ala Asp Val Thr Val Tyr Ser
        100                 105                 110 ctt gag gac ctc acc gct ctg gct tct gaa cat act tct aag aac aca       744
Leu Glu Asp Leu Thr Ala Leu Ala Ser Glu His Thr Ser Lys Asn Thr
    115                 120                 125 gat acc ttc gcg gcc gtg ttt tcg ttt ctg tct gga agg tta gtg cac       792
```

```
Asp Thr Phe Ala Ala Val Phe Ser Phe Leu Ser Gly Arg Leu Val His
130                 135                 140                 145 att tct gag cag gct gct ttg atc ctg aat tct aag agg ggt ttc ctc        840
Ile Ser Glu Gln Ala Ala Leu Ile Leu Asn Ser Lys Arg Gly Phe Leu
            150                 155                 160 aag agc gtg cac ttt gtc gac ctg ctt gcc cct caa gac gtg agg gcg        888
Lys Ser Val His Phe Val Asp Leu Leu Ala Pro Gln Asp Val Arg Ala
                165                 170                 175 ttc tac gcg cac act gct cca act cag ctt cct ttc tgg aac aac tgg        936
Phe Tyr Ala His Thr Ala Pro Thr Gln Leu Pro Phe Trp Asn Asn Trp
        180                 185                 190 acc caa aga gcc tcg cag tat gaa tgt gca cca gcg aaa ccc ttt ttc        984
Thr Gln Arg Ala Ser Gln Tyr Glu Cys Ala Pro Ala Lys Pro Phe Phe
    195                 200                 205 tgc aga atc tgt gga ggt gga gac aga gag aag agg cat tac tcc cca       1032
Cys Arg Ile Cys Gly Gly Gly Asp Arg Glu Lys Arg His Tyr Ser Pro
210                 215                 220                 225 ttc cgg atc ctc ccc tat ttg gtt cat gta cat agc tct gcc cag cca       1080
Phe Arg Ile Leu Pro Tyr Leu Val His Val His Ser Ser Ala Gln Pro
                230                 235                 240 gaa cca gag cct tgc tgt cta aca ctg gtt gaa aag att cac tct ggt       1128
Glu Pro Glu Pro Cys Cys Leu Thr Leu Val Glu Lys Ile His Ser Gly
            245                 250                 255 tac gaa gct cct cga atc cct gta gat aaa aga att ttt acc aca aca       1176
Tyr Glu Ala Pro Arg Ile Pro Val Asp Lys Arg Ile Phe Thr Thr Thr
        260                 265                 270 cac act cca gga tgt gtg ttt ctt gaa gta gat gaa aga gca gtg cct       1224
His Thr Pro Gly Cys Val Phe Leu Glu Val Asp Glu Arg Ala Val Pro
    275                 280                 285 ttg ctg ggt tac cta cct cag gat ctg att gga aca tcg atc tta aca       1272
Leu Leu Gly Tyr Leu Pro Gln Asp Leu Ile Gly Thr Ser Ile Leu Thr
290                 295                 300                 305 tac ttg cac cca gaa gat cgg cct ctg atg gtt gcc ata cac caa aaa       1320
Tyr Leu His Pro Glu Asp Arg Pro Leu Met Val Ala Ile His Gln Lys
                310                 315                 320 gtt tta aag tat gcc ggc cac cct ccg ttt gaa cac tcg ccc gtc aga       1368
Val Leu Lys Tyr Ala Gly His Pro Pro Phe Glu His Ser Pro Val Arg
            325                 330                 335 ttc tgc act cag aac gga gag tat gtc att ctg gat tcc agc tgg tcc       1416
Phe Cys Thr Gln Asn Gly Glu Tyr Val Ile Leu Asp Ser Ser Trp Ser
        340                 345                 350 agc ttt gtc aac ccc tgg agc cgg aag gtc tcc ttc atc att ggt cga       1464
Ser Phe Val Asn Pro Trp Ser Arg Lys Val Ser Phe Ile Ile Gly Arg
    355                 360                 365 cat aaa gtc cga acg agt cca tta aat gaa gat gtt ttt gcc acc aga       1512
His Lys Val Arg Thr Ser Pro Leu Asn Glu Asp Val Phe Ala Thr Arg
370                 375                 380                 385 ata aaa aag gca gcc agt aac gac aaa gac ata gca gaa tta caa gaa       1560
Ile Lys Lys Ala Ala Ser Asn Asp Lys Asp Ile Ala Glu Leu Gln Glu
                390                 395                 400 caa att cac aaa ctt ctc ttg cag ccg gtt cat gct agt gct tcc agt       1608
Gln Ile His Lys Leu Leu Leu Gln Pro Val His Ala Ser Ala Ser Ser
            405                 410                 415 ggc tac ggg agc ctg ggc agc agc ggc tca cag gag cag cac gtc agc       1656
Gly Tyr Gly Ser Leu Gly Ser Ser Gly Ser Gln Glu Gln His Val Ser
        420                 425                 430 atc acc tct tcg agt gag tcc agc ggg cac tgt ccg gag gaa ggc cag       1704
Ile Thr Ser Ser Ser Glu Ser Ser Gly His Cys Pro Glu Glu Gly Gln
    435                 440                 445
```

-continued

| | |
|---|---|
| cat gag cag atg acc ctg cag cag gtc tat gcc agt gta aac aaa att<br>His Glu Gln Met Thr Leu Gln Gln Val Tyr Ala Ser Val Asn Lys Ile<br>450                         455                  460                  465 | 1752 |
| aag aat gtg ggc caa cag ctc tac atc gag tcc atg gcc aga tca tca<br>Lys Asn Val Gly Gln Gln Leu Tyr Ile Glu Ser Met Ala Arg Ser Ser<br>                  470                  475                  480 | 1800 |
| gtg aag cca gtg gca gag acg tgc gtg gaa ccg cag ggt ggt gat gag<br>Val Lys Pro Val Ala Glu Thr Cys Val Glu Pro Gln Gly Gly Asp Glu<br>485                         490                  495 | 1848 |
| cag aag gac ttt tct tcc tct cag aca ctg aaa aat aaa agc acc acg<br>Gln Lys Asp Phe Ser Ser Ser Gln Thr Leu Lys Asn Lys Ser Thr Thr<br>     500                  505                  510 | 1896 |
| gat act ggc tcc ggt ggc aat ctg cag caa gag cag ccc agc tcg tcc<br>Asp Thr Gly Ser Gly Gly Asn Leu Gln Gln Glu Gln Pro Ser Ser Ser<br>515                         520                  525 | 1944 |
| tat cag cag atg aac tgt atc gac agt gtc atc agg tac ctg aca agc<br>Tyr Gln Gln Met Asn Cys Ile Asp Ser Val Ile Arg Tyr Leu Thr Ser<br>530                         535                  540                  545 | 1992 |
| tac agc ctc ccg gcc ttg aaa aga aag tgc atc tcc tgc aca aac aca<br>Tyr Ser Leu Pro Ala Leu Lys Arg Lys Cys Ile Ser Cys Thr Asn Thr<br>                  550                  555                  560 | 2040 |
| tct tca tcc tca gaa gaa gcc aag cca atc ccg gag gtg gac agc agc<br>Ser Ser Ser Ser Glu Glu Ala Lys Pro Ile Pro Glu Val Asp Ser Ser<br>565                         570                  575 | 2088 |
| cag aga gac acg gaa cag ctc ctg gac ata cgg aaa cag gaa aca act<br>Gln Arg Asp Thr Glu Gln Leu Leu Asp Ile Arg Lys Gln Glu Thr Thr<br>                  580                  585                  590 | 2136 |
| gga cca tcc aca gac atc gaa gga ggt gct gct cgg acc ctg tcc acc<br>Gly Pro Ser Thr Asp Ile Glu Gly Gly Ala Ala Arg Thr Leu Ser Thr<br>595                         600                  605 | 2184 |
| gcc gca ctg agc gtg gcg tct ggc atc agc cag tgc agc tgc agc agc<br>Ala Ala Leu Ser Val Ala Ser Gly Ile Ser Gln Cys Ser Cys Ser Ser<br>610                         615                  620                  625 | 2232 |
| acc tct ggc cac gct ccg ccc cta cag tca gaa agt gtt gcc gtg gcg<br>Thr Ser Gly His Ala Pro Pro Leu Gln Ser Glu Ser Val Ala Val Ala<br>                  630                  635                  640 | 2280 |
| tgt aag ccg tgg gcc ctg aga acg aag gcc tct cac ctg gct gca gga<br>Cys Lys Pro Trp Ala Leu Arg Thr Lys Ala Ser His Leu Ala Ala Gly<br>645                         650                  655 | 2328 |
| gga ttt aag cac gtg ggg ctc aca gca gct gtc ctc tct gca cac aca<br>Gly Phe Lys His Val Gly Leu Thr Ala Ala Val Leu Ser Ala His Thr<br>                  660                  665                  670 | 2376 |
| cag aag gaa gag cag aac tac gtt gac agg ttc cgg gaa aag atc ctg<br>Gln Lys Glu Glu Gln Asn Tyr Val Asp Arg Phe Arg Glu Lys Ile Leu<br>675                         680                  685 | 2424 |
| acc tcg ccc tac ggt tgc tat ctt cag caa gag agc aga aac cgt gct<br>Thr Ser Pro Tyr Gly Cys Tyr Leu Gln Gln Glu Ser Arg Asn Arg Ala<br>690                         695                  700                  705 | 2472 |
| cag tac tcc tgt gtt caa gca ggg tcc act gct aag cac agc aga tgt<br>Gln Tyr Ser Cys Val Gln Ala Gly Ser Thr Ala Lys His Ser Arg Cys<br>                  710                  715                  720 | 2520 |
| gct gga agc gag agg cag aag cac aaa cga aag aag ttg cca gca cct<br>Ala Gly Ser Glu Arg Gln Lys His Lys Arg Lys Lys Leu Pro Ala Pro<br>                    725                  730                  735 | 2568 |
| gtg gac acc agc agc ccc ggt gcc cac ctc tgt ccc cat gtc aca gga<br>Val Asp Thr Ser Ser Pro Gly Ala His Leu Cys Pro His Val Thr Gly<br>740                         745                  750 | 2616 |
| ctc ctc ccg gat gag cag cac tgg ggc cca tcc gct agc ccc tcc ccc<br>Leu Leu Pro Asp Glu Gln His Trp Gly Pro Ser Ala Ser Pro Ser Pro<br>755                         760                  765 | 2664 |

```
ctc ggc gca ggc tta gca ttc ccc tcg gcc ctg gta gtt ccc agc cag    2712
Leu Gly Ala Gly Leu Ala Phe Pro Ser Ala Leu Val Val Pro Ser Gln
770             775                 780                 785 acc cct tat ctc ctc ccc tct ttt ccc ctc caa gat atg gcc tct cag    2760
Thr Pro Tyr Leu Leu Pro Ser Phe Pro Leu Gln Asp Met Ala Ser Gln
                790                 795                 800 gga gtg ggg gtc tcg gca gcc tgg gga gct gca gcc gga tgt cca cct    2808
Gly Val Gly Val Ser Ala Ala Trp Gly Ala Ala Gly Cys Pro Pro
            805                 810                 815 ctg tcc gcc ggc ccc cag gct gtt gcc gcg ttc ccc tcc gct tac gtg    2856
Leu Ser Ala Gly Pro Gln Ala Val Ala Ala Phe Pro Ser Ala Tyr Val
        820                 825                 830 gat act ttg atg acc atc ttc ctg cac aac gcc cct ctc ttc cct ctg    2904
Asp Thr Leu Met Thr Ile Phe Leu His Asn Ala Pro Leu Phe Pro Leu
835                 840                 845 tgg ccg ccc tcg ttc tcc cca tac cca tcc ctg ggg gcc gca ggg tct    2952
Trp Pro Pro Ser Phe Ser Pro Tyr Pro Ser Leu Gly Ala Ala Gly Ser
850                 855                 860                 865 tct gaa ctg gca ccc tta gta cca gca atg gct cca aac ccg gaa cca    3000
Ser Glu Leu Ala Pro Leu Val Pro Ala Met Ala Pro Asn Pro Glu Pro
                870                 875                 880 acc act tca ggc cac agc caa agg aga gtg gag gag aac tgg gag gca    3048
Thr Thr Ser Gly His Ser Gln Arg Arg Val Glu Glu Asn Trp Glu Ala
            885                 890                 895 cac agt gaa gag ctt ccg ttc att agc tca cgg agc agt tca ccg tta    3096
His Ser Glu Glu Leu Pro Phe Ile Ser Ser Arg Ser Ser Ser Pro Leu
        900                 905                 910 cag tta aat tta ctc cag gaa gaa atg cct gcg ccg tca gag tcc gca    3144
Gln Leu Asn Leu Leu Gln Glu Glu Met Pro Ala Pro Ser Glu Ser Ala
915                 920                 925 gac gca gtg aga aga ggc gct ggg cca gac gct aag cat cac tgt gtt    3192
Asp Ala Val Arg Arg Gly Ala Gly Pro Asp Ala Lys His His Cys Val
930                 935                 940                 945 aca ggt ccc agt ggc agt agg agc cgt cac tgc acc tct ggt gag ctg    3240
Thr Gly Pro Ser Gly Ser Arg Ser Arg His Cys Thr Ser Gly Glu Leu
                950                 955                 960 gcc acg gca aca gcg cac cag gag tct gct gct gcc tca gga agc agt    3288
Ala Thr Ala Thr Ala His Gln Glu Ser Ala Ala Ala Ser Gly Ser Ser
            965                 970                 975 gcc agc agt ata tac ttc agt agc act gac tat gct tct gaa gtc tct    3336
Ala Ser Ser Ile Tyr Phe Ser Ser Thr Asp Tyr Ala Ser Glu Val Ser
        980                 985                 990 gaa aac aga cag agg cca cag gat aga cag aga gac gaa gcc ctt ccc    3384
Glu Asn Arg Gln Arg Pro Gln Asp Arg Gln Arg Asp Glu Ala Leu Pro
    995                 1000                1005 ggg gcg gct gaa gag tcc atc tgg aga atg ata gag cgg aca cca gag    3432
Gly Ala Ala Glu Glu Ser Ile Trp Arg Met Ile Glu Arg Thr Pro Glu
1010                1015                1020                1025 tgt gta ctc atg aca tac cag gtg ccc gag agg ggt cga gag gag gtg    3480
Cys Val Leu Met Thr Tyr Gln Val Pro Glu Arg Gly Arg Glu Glu Val
                1030                1035                1040 ctg aag cag gac ctg gag aag ctc cag agc atg gaa cag cag cag ccc    3528
Leu Lys Gln Asp Leu Glu Lys Leu Gln Ser Met Glu Gln Gln Gln Pro
            1045                1050                1055 ctg ttc tct ccc gcg cag agg gag gag ctg gcc aag gtg cgc tcc tgg    3576
Leu Phe Ser Pro Ala Gln Arg Glu Glu Leu Ala Lys Val Arg Ser Trp
        1060                1065                1070 atc cac agc cac aca gcc cct cag gag gga cac ctc cag agc tgt gtc    3624
Ile His Ser His Thr Ala Pro Gln Glu Gly His Leu Gln Ser Cys Val
```

-continued

```
             1075                1080                1085
gcc tgt gaa gac aga ggt tca gtg ggt gac act gca gag gtc ctg gaa      3672
Ala Cys Glu Asp Arg Gly Ser Val Gly Asp Thr Ala Glu Val Leu Glu
1090                1095                1100                1105 cag cgc cca gca gaa gac acc agt tgagcagctg taaagatgtc acacccctc     3726
Gln Arg Pro Ala Glu Asp Thr Ser
            1110 caggtcacgt gggacacaga gccgtgcgtt acctcaccac agtctaactc tgaaacgcca   3786 gtcattgaca ttaaggtctt ccctggcttt gttctggttt ggttttggtg cgctggggga   3846 tcaaacccag ggcctcacat ccactaggct ggcactctcc actgctgacc tgtctcccca   3906 ggtctccctt cttggttttc ccaaaacatg agcagacgtt ggctcttgtt catgatagta   3966 aaacagtcaa caagacgtct tctctaactc atctgtcacc tgaagacatt gggctgtgtc   4026 tgacagcaga tttcagaggt caccctgagt aagttacagt tggaacgagt cgcaggcctt   4086 cgtctcgttt gctttttat gttgttacaa gatcactttc ccactagaat acttgaagaa    4146 cttctgtctg taggttgtgt gtttctcacg gggtgtccgt gaacttacca cattgatcta   4206 ggttttgtac agcatggtgc ttctcttcct gatggtaaga cattccagct ttctctcaga   4266 gcgtcagagc gcatcattcc ccaggaactg tgggactcgt ggctttggtt gtttgacccc   4326 attctcgtcc atgaagttcc tgtggcagct gccttttcaca ggggctcttt ccttaagatc  4386 tgtcagctag ccaggactta ctccttggat gactgaagtt aagccttgca tggcaaaaag   4446 cttcttaccc aaacaatagt gttttcaaca gttttaaata ttacgttaat gttatcatgg   4506 agatgtgtgt gccccggctc accaaaacaa acagttaacc tttccttttc accaaacgac   4566 acgatgacga ccagcggtct gccttttgtt tgcccttgaa gaggggtaag agtttgggag   4626 actacactta agggagctcg ggaccccag ctcggtgaca gcagagtccc atgagtccac    4686 gctctccagg cagtttctgc ctcagaagtg agtgtgattg ttcacgcgtc tgtcctctca   4746 ctgtctggtg ctctggttta aagaagccca agttccttc ttgaactcga gatggcagtg    4806 gagccacccg tgcaggtcag gaaggaactg acggggagga ggtttacagt ggccttt      4863
```

<210> SEQ ID NO 9
<211> LENGTH: 1113
<212> TYPE: PRT
<213> ORGANISM: Mus musculus

<400> SEQUENCE: 9

```
Met Asp Pro Cys Gly Asp Pro Ala Val Pro Gly Gly Asp Cys Pro Gln
1               5                   10                  15

Thr Arg Gly Pro Gly Leu Gln Gly Ala Ser Gly Gln Glu Gly Pro Leu
            20                  25                  30

Gln Gly Thr Cys Val Asp Ser Ser His Ser Glu His Glu Asp Arg Asn
        35                  40                  45

Arg Met Ser Glu Glu Leu Ile Met Val Val Gln Glu Met Lys Lys Tyr
    50                  55                  60

Phe Pro Ala Glu Arg His Thr Lys Pro Ser Thr Leu Asp Ala Leu Asn
65                  70                  75                  80

Tyr Ala Leu Arg Cys Val His Ser Val Gln Ala Asn Ser Asp Phe Phe
                85                  90                  95

Gln Ser Leu Gly Pro Arg Gly Ala His Gln Ala Asp Val Thr Val Tyr
            100                 105                 110

Ser Leu Glu Asp Leu Thr Ala Leu Ala Ser Glu His Thr Ser Lys Asn
        115                 120                 125
```

-continued

```
Thr Asp Thr Phe Ala Ala Val Phe Ser Phe Leu Ser Gly Arg Leu Val
    130                 135                 140
His Ile Ser Glu Gln Ala Ala Leu Ile Leu Asn Ser Lys Arg Gly Phe
145                 150                 155                 160
Leu Lys Ser Val His Phe Val Asp Leu Leu Ala Pro Gln Asp Val Arg
                165                 170                 175
Ala Phe Tyr Ala His Thr Ala Pro Thr Gln Leu Pro Phe Trp Asn Asn
                180                 185                 190
Trp Thr Gln Arg Ala Ser Gln Tyr Glu Cys Ala Pro Ala Lys Pro Phe
            195                 200                 205
Phe Cys Arg Ile Cys Gly Gly Asp Arg Glu Lys Arg His Tyr Ser
210                 215                 220
Pro Phe Arg Ile Leu Pro Tyr Leu Val His Val His Ser Ser Ala Gln
225                 230                 235                 240
Pro Glu Pro Glu Pro Cys Cys Leu Thr Leu Val Glu Lys Ile His Ser
                245                 250                 255
Gly Tyr Glu Ala Pro Arg Ile Pro Val Asp Lys Arg Ile Phe Thr Thr
                260                 265                 270
Thr His Thr Pro Gly Cys Val Phe Leu Glu Val Asp Glu Arg Ala Val
            275                 280                 285
Pro Leu Leu Gly Tyr Leu Pro Gln Asp Leu Ile Gly Thr Ser Ile Leu
290                 295                 300
Thr Tyr Leu His Pro Glu Asp Arg Pro Leu Met Val Ala Ile His Gln
305                 310                 315                 320
Lys Val Leu Lys Tyr Ala Gly His Pro Pro Phe Glu His Ser Pro Val
                325                 330                 335
Arg Phe Cys Thr Gln Asn Gly Glu Tyr Val Ile Leu Asp Ser Ser Trp
                340                 345                 350
Ser Ser Phe Val Asn Pro Trp Ser Arg Lys Val Ser Phe Ile Ile Gly
            355                 360                 365
Arg His Lys Val Arg Thr Ser Pro Leu Asn Glu Asp Val Phe Ala Thr
370                 375                 380
Arg Ile Lys Lys Ala Ala Ser Asn Asp Lys Asp Ile Ala Glu Leu Gln
385                 390                 395                 400
Glu Gln Ile His Lys Leu Leu Leu Gln Pro Val His Ala Ser Ala Ser
                405                 410                 415
Ser Gly Tyr Gly Ser Leu Gly Ser Gly Ser Gln Glu Gln His Val
            420                 425                 430
Ser Ile Thr Ser Ser Ser Glu Ser Ser Gly His Cys Pro Glu Glu Gly
            435                 440                 445
Gln His Glu Gln Met Thr Leu Gln Gln Val Tyr Ala Ser Val Asn Lys
450                 455                 460
Ile Lys Asn Val Gly Gln Gln Leu Tyr Ile Glu Ser Met Ala Arg Ser
465                 470                 475                 480
Ser Val Lys Pro Val Ala Glu Thr Cys Val Glu Pro Gln Gly Gly Asp
                485                 490                 495
Glu Gln Lys Asp Phe Ser Ser Ser Gln Thr Leu Lys Asn Lys Ser Thr
                500                 505                 510
Thr Asp Thr Gly Ser Gly Gly Asn Leu Gln Gln Glu Gln Pro Ser Ser
            515                 520                 525
Ser Tyr Gln Gln Met Asn Cys Ile Asp Ser Val Ile Arg Tyr Leu Thr
530                 535                 540
```

-continued

```
Ser Tyr Ser Leu Pro Ala Leu Lys Arg Lys Cys Ile Ser Cys Thr Asn
545                 550                 555                 560

Thr Ser Ser Ser Glu Glu Ala Lys Pro Ile Pro Glu Val Asp Ser
            565                 570                 575

Ser Gln Arg Asp Thr Glu Gln Leu Leu Asp Ile Arg Lys Gln Glu Thr
            580                 585                 590

Thr Gly Pro Ser Thr Asp Ile Glu Gly Gly Ala Ala Arg Thr Leu Ser
        595                 600                 605

Thr Ala Ala Leu Ser Val Ala Ser Gly Ile Ser Gln Cys Ser Cys Ser
        610                 615                 620

Ser Thr Ser Gly His Ala Pro Pro Leu Gln Ser Glu Ser Val Ala Val
625                 630                 635                 640

Ala Cys Lys Pro Trp Ala Leu Arg Thr Lys Ala Ser His Leu Ala Ala
                645                 650                 655

Gly Gly Phe Lys His Val Gly Leu Thr Ala Ala Val Leu Ser Ala His
                660                 665                 670

Thr Gln Lys Glu Glu Gln Asn Tyr Val Asp Arg Phe Arg Glu Lys Ile
            675                 680                 685

Leu Thr Ser Pro Tyr Gly Cys Tyr Leu Gln Gln Glu Ser Arg Asn Arg
690                 695                 700

Ala Gln Tyr Ser Cys Val Gln Ala Gly Ser Thr Ala Lys His Ser Arg
705                 710                 715                 720

Cys Ala Gly Ser Glu Arg Gln Lys His Lys Arg Lys Leu Pro Ala
                725                 730                 735

Pro Val Asp Thr Ser Ser Pro Gly Ala His Leu Cys Pro His Val Thr
                740                 745                 750

Gly Leu Leu Pro Asp Glu Gln His Trp Gly Pro Ser Ala Ser Pro Ser
            755                 760                 765

Pro Leu Gly Ala Gly Leu Ala Phe Pro Ser Ala Leu Val Val Pro Ser
770                 775                 780

Gln Thr Pro Tyr Leu Leu Pro Ser Phe Pro Leu Gln Asp Met Ala Ser
785                 790                 795                 800

Gln Gly Val Gly Val Ser Ala Ala Trp Gly Ala Ala Ala Gly Cys Pro
                805                 810                 815

Pro Leu Ser Ala Gly Pro Gln Ala Val Ala Ala Phe Pro Ser Ala Tyr
            820                 825                 830

Val Asp Thr Leu Met Thr Ile Phe Leu His Asn Ala Pro Leu Phe Pro
            835                 840                 845

Leu Trp Pro Pro Ser Phe Ser Pro Tyr Pro Ser Leu Gly Ala Ala Gly
850                 855                 860

Ser Ser Glu Leu Ala Pro Leu Val Pro Ala Met Ala Pro Asn Pro Glu
865                 870                 875                 880

Pro Thr Thr Ser Gly His Ser Gln Arg Arg Val Glu Glu Asn Trp Glu
                885                 890                 895

Ala His Ser Glu Glu Leu Pro Phe Ile Ser Ser Arg Ser Ser Ser Pro
            900                 905                 910

Leu Gln Leu Asn Leu Leu Gln Glu Glu Met Pro Ala Pro Ser Glu Ser
            915                 920                 925

Ala Asp Ala Val Arg Arg Gly Ala Gly Pro Asp Ala Lys His His Cys
        930                 935                 940

Val Thr Gly Pro Ser Gly Ser Arg Ser Arg His Cys Thr Ser Gly Glu
945                 950                 955                 960

Leu Ala Thr Ala Thr Ala His Gln Glu Ser Ala Ala Ala Ser Gly Ser
```

|  |  |  |  |  | 965 |  |  |  | 970 |  |  |  | 975 |  |
|---|---|---|---|---|---|---|---|---|---|---|---|---|---|---|

Ser Ala Ser Ser Ile Tyr Phe Ser Ser Thr Asp Tyr Ala Ser Glu Val
                    980                 985                 990

Ser Glu Asn Arg Gln Arg Pro Gln Asp Arg Gln Arg Asp Glu Ala Leu
                995                 1000                1005

Pro Gly Ala Ala Glu Glu Ser Ile Trp Arg Met Ile Glu Arg Thr Pro
1010                1015                1020

Glu Cys Val Leu Met Thr Tyr Gln Val Pro Glu Arg Gly Arg Glu Glu
1025                1030                1035                1040

Val Leu Lys Gln Asp Leu Glu Lys Leu Gln Ser Met Glu Gln Gln Gln
                1045                1050                1055

Pro Leu Phe Ser Pro Ala Gln Arg Glu Glu Leu Ala Lys Val Arg Ser
                1060                1065                1070

Trp Ile His Ser His Thr Ala Pro Gln Glu Gly His Leu Gln Ser Cys
                1075                1080                1085

Val Ala Cys Glu Asp Arg Gly Ser Val Gly Asp Thr Ala Glu Val Leu
                1090                1095                1100

Glu Gln Arg Pro Ala Glu Asp Thr Ser
1105                1110

<210> SEQ ID NO 10
<211> LENGTH: 7478
<212> TYPE: DNA
<213> ORGANISM: Mus musculus
<220> FEATURE:
<221> NAME/KEY: CDS
<222> LOCATION: (389)...(2953)

<400> SEQUENCE: 10
ggggaggagc gcggcggtag cggtgaattt tgaggggtgg gtcgggggcg cgcactcgcc     60 gccctggtg ctgccggctc ccggagccgt ggcgtgtccc tgctgtcgcc gctcggctgt    120
cgcgagccgc cgcgggcaga gtcccgggcg ggggagggag gaagccggag cctcaggcac    180
gtgaaagaaa agcacaagaa gaaacttta caggcgttgt tgattggact agggcaacga    240
ttcccaaaat caccagcaag agttctgatg gtcagtcaca cagaagacgg ccttgcgtct    300
gtgggtgttg gagactccat tctaaagata taaaagtga agaggagaa gtacaaatgt     360 ctaccacaag acgaaaacat aatgtgtt atg gtg ttt acc gta agc tgt agt       412
                                Met Val Phe Thr Val Ser Cys Ser
                                 1               5 aaa atg agc tca att gtt gac aga gat gac agt agt att ttt gat gga    460
Lys Met Ser Ser Ile Val Asp Arg Asp Asp Ser Ser Ile Phe Asp Gly
 10              15                  20 ttg gtg gaa gaa gat gac aag gac aaa gca aaa aga gta tct aga aac    508
Leu Val Glu Glu Asp Asp Lys Asp Lys Ala Lys Arg Val Ser Arg Asn
 25              30                  35              40 aaa tca gaa aag aaa cgt aga gat cag ttc aat gtc ctc att aag gag    556
Lys Ser Glu Lys Lys Arg Arg Asp Gln Phe Asn Val Leu Ile Lys Glu
                 45                  50                  55 ctg ggg tct atg ctt cct ggt aac gcg aga aag atg gac aag tct act    604
Leu Gly Ser Met Leu Pro Gly Asn Ala Arg Lys Met Asp Lys Ser Thr
             60                  65                  70 gtt cta cag aag agc att gat ttt ttg cgc aaa cat aaa gag acc act    652
Val Leu Gln Lys Ser Ile Asp Phe Leu Arg Lys His Lys Glu Thr Thr
         75                  80                  85 gca cag tca gat gct agt gag att cga cag gac tgg aaa ccc aca ttc    700
Ala Gln Ser Asp Ala Ser Glu Ile Arg Gln Asp Trp Lys Pro Thr Phe
     90                  95                 100

```
ctt agt aat gaa gag ttt aca cag tta atg tta gag gct ctt gat ggt      748
Leu Ser Asn Glu Glu Phe Thr Gln Leu Met Leu Glu Ala Leu Asp Gly
105                 110                 115                 120 ttt ttt tta gcg atc atg aca gat gga agt ata ata tat gta tct gag      796
Phe Phe Leu Ala Ile Met Thr Asp Gly Ser Ile Ile Tyr Val Ser Glu
                125                 130                 135 agt gta act tcg tta ctt gaa cat tta cca tct gat ctt gtg gat caa      844
Ser Val Thr Ser Leu Leu Glu His Leu Pro Ser Asp Leu Val Asp Gln
        140                 145                 150 agt ata ttt aat ttt atc cca gag gga gaa cat tca gag gtt tat aag      892
Ser Ile Phe Asn Phe Ile Pro Glu Gly Glu His Ser Glu Val Tyr Lys
    155                 160                 165 ata ctc tct act cat ctg ctg gaa agt gac tca tta acc cct gag tac      940
Ile Leu Ser Thr His Leu Leu Glu Ser Asp Ser Leu Thr Pro Glu Tyr
170                 175                 180 tta aaa tca aaa aat cag tta gaa ttc tgt tgt cac atg ctt cga gga      988
Leu Lys Ser Lys Asn Gln Leu Glu Phe Cys Cys His Met Leu Arg Gly
185                 190                 195                 200 aca ata gac cca aag gag cca tcc acc tat gaa tat gtg aga ttt ata     1036
Thr Ile Asp Pro Lys Glu Pro Ser Thr Tyr Glu Tyr Val Arg Phe Ile
                205                 210                 215 gga aat ttt aaa tct tta acc agt gta tca act tca aca cac aat ggt     1084
Gly Asn Phe Lys Ser Leu Thr Ser Val Ser Thr Ser Thr His Asn Gly
        220                 225                 230 ttt gaa gga act ata caa cgc aca cat agg cct tct tat gaa gat aga     1132
Phe Glu Gly Thr Ile Gln Arg Thr His Arg Pro Ser Tyr Glu Asp Arg
    235                 240                 245 gtt tgt ttt gta gct act gtc aga tta gct aca cct cag ttc atc aag     1180
Val Cys Phe Val Ala Thr Val Arg Leu Ala Thr Pro Gln Phe Ile Lys
250                 255                 260 gaa atg tgt act gtt gaa gaa cca aat gaa gag ttt aca tct aga cac     1228
Glu Met Cys Thr Val Glu Glu Pro Asn Glu Glu Phe Thr Ser Arg His
265                 270                 275                 280 agt tta gaa tgg aag ttt cta ttt tta gat cac agg gca cca cca ata     1276
Ser Leu Glu Trp Lys Phe Leu Phe Leu Asp His Arg Ala Pro Pro Ile
                285                 290                 295 ata ggc tat ttg cca ttt gaa gtc ttg gga aca tca ggc tat gat tac     1324
Ile Gly Tyr Leu Pro Phe Glu Val Leu Gly Thr Ser Gly Tyr Asp Tyr
        300                 305                 310 tat cat gtg gat gac cta gaa aat ctg gca aaa tgt cac gag cac tta     1372
Tyr His Val Asp Asp Leu Glu Asn Leu Ala Lys Cys His Glu His Leu
    315                 320                 325 atg caa tat gga aaa ggc aaa tcg tgt tac tat aga ttc ctg acc aaa     1420
Met Gln Tyr Gly Lys Gly Lys Ser Cys Tyr Tyr Arg Phe Leu Thr Lys
330                 335                 340 ggc cag cag tgg ata tgg ctt cag act cat tat tat att act tac cat     1468
Gly Gln Gln Trp Ile Trp Leu Gln Thr His Tyr Tyr Ile Thr Tyr His
345                 350                 355                 360 cag tgg aat tca agg cca gag ttc att gtt tgt act cac act gta gta     1516
Gln Trp Asn Ser Arg Pro Glu Phe Ile Val Cys Thr His Thr Val Val
                365                 370                 375 agt tat gca gaa gtt agg gct gaa aga cgg cga gaa ctt ggc att gaa     1564
Ser Tyr Ala Glu Val Arg Ala Glu Arg Arg Arg Glu Leu Gly Ile Glu
        380                 385                 390 gag tct ctt cct gag aca gct gct gac aaa agc caa gat tct ggg tct     1612
Glu Ser Leu Pro Glu Thr Ala Ala Asp Lys Ser Gln Asp Ser Gly Ser
    395                 400                 405 gac aat cgt atc aac aca gtg agt ctc aag gaa gca ctg gaa agg ttt     1660
Asp Asn Arg Ile Asn Thr Val Ser Leu Lys Glu Ala Leu Glu Arg Phe
```

```
                        -continued 410                 415                 420
gat cac agc cca act cct tct gcc tcc tct aga agc tca cga aag tca    1708
Asp His Ser Pro Thr Pro Ser Ala Ser Ser Arg Ser Ser Arg Lys Ser
425                 430                 435                 440 tct cac acc gca gtc tca gac cct tcc tcc aca ccg aca aag atc cct    1756
Ser His Thr Ala Val Ser Asp Pro Ser Ser Thr Pro Thr Lys Ile Pro
                445                 450                 455 act gat act agc act cct ccc aga cag cat ttg cca gct cat gaa aag    1804
Thr Asp Thr Ser Thr Pro Pro Arg Gln His Leu Pro Ala His Glu Lys
            460                 465                 470 atg aca cag cgg agg tcg tcc ttc agc agt cag tcc ata aac tcc cag    1852
Met Thr Gln Arg Arg Ser Ser Phe Ser Ser Gln Ser Ile Asn Ser Gln
        475                 480                 485 tca gtt ggt cca tca tta aca cag cca gcg atg tct caa gct gca aat    1900
Ser Val Gly Pro Ser Leu Thr Gln Pro Ala Met Ser Gln Ala Ala Asn
    490                 495                 500 tta cca att cca caa ggc atg tca cag ttt cag ttt tca gct cag tta    1948
Leu Pro Ile Pro Gln Gly Met Ser Gln Phe Gln Phe Ser Ala Gln Leu
505                 510                 515                 520 gga gcc atg cag cat cta aaa gac cag cta gag cag cgg aca cgg atg    1996
Gly Ala Met Gln His Leu Lys Asp Gln Leu Glu Gln Arg Thr Arg Met
                525                 530                 535 ata gag gca aat att cat cgg cag caa gaa gaa cta agg aaa att caa    2044
Ile Glu Ala Asn Ile His Arg Gln Gln Glu Glu Leu Arg Lys Ile Gln
            540                 545                 550 gag caa ctt cag atg gtc cat ggt caa ggg cta cag atg ttt ttg cag    2092
Glu Gln Leu Gln Met Val His Gly Gln Gly Leu Gln Met Phe Leu Gln
        555                 560                 565 caa tca aac cct gga ttg aat ttt ggt tct gtt caa ctt tcc tct gga    2140
Gln Ser Asn Pro Gly Leu Asn Phe Gly Ser Val Gln Leu Ser Ser Gly
    570                 575                 580 aat tct aat atc cag cag ctc aca cct gta aat atg caa ggc cag gtt    2188
Asn Ser Asn Ile Gln Gln Leu Thr Pro Val Asn Met Gln Gly Gln Val
585                 590                 595                 600 gtc cct gct aac cag gtt cag agt gga cat atc agc aca ggc cag cac    2236
Val Pro Ala Asn Gln Val Gln Ser Gly His Ile Ser Thr Gly Gln His
                605                 610                 615 atg ata cag caa cag act tta caa agt aca tca act cag cag agt caa    2284
Met Ile Gln Gln Gln Thr Leu Gln Ser Thr Ser Thr Gln Gln Ser Gln
            620                 625                 630 cag agt gta atg agt gga cac agt cag cag acg tct ctt cca agt cag    2332
Gln Ser Val Met Ser Gly His Ser Gln Gln Thr Ser Leu Pro Ser Gln
        635                 640                 645 aca ccg agc act ctc aca gcc cca ctg tac aat acg atg gtg att tcc    2380
Thr Pro Ser Thr Leu Thr Ala Pro Leu Tyr Asn Thr Met Val Ile Ser
    650                 655                 660 cag cct gca gct ggg agc atg gtc cag att cca tcc agt atg cca cag    2428
Gln Pro Ala Ala Gly Ser Met Val Gln Ile Pro Ser Ser Met Pro Gln
665                 670                 675                 680 aac agt acc cag agt gct aca gtc act acg ttc act cag gac aga cag    2476
Asn Ser Thr Gln Ser Ala Thr Val Thr Thr Phe Thr Gln Asp Arg Gln
                685                 690                 695 ata aga ttt tct caa ggt cag caa ctt gtg acc aaa tta gtg act gct    2524
Ile Arg Phe Ser Gln Gly Gln Gln Leu Val Thr Lys Leu Val Thr Ala
            700                 705                 710 cct gta gct tgt ggg gcc gtc atg gta cca agt acc atg ctt atg ggt    2572
Pro Val Ala Cys Gly Ala Val Met Val Pro Ser Thr Met Leu Met Gly
        715                 720                 725 cag gtg gtg act gcc tat cct acc ttc gcc aca caa cag cag cag gca    2620
```

```
                                                       -continued

Gln Val Val Thr Ala Tyr Pro Thr Phe Ala Thr Gln Gln Gln Ala
        730                 735                 740 cag aca tta tcg gta aca caa cag cag cag cag cag cag cag cca       2668
Gln Thr Leu Ser Val Thr Gln Gln Gln Gln Gln Gln Gln Gln Pro
745                 750                 755                 760 cca cag caa cag caa caa caa cag cag agt tcc cag gaa cag cag ctt   2716
Pro Gln Gln Gln Gln Gln Gln Gln Gln Ser Ser Gln Glu Gln Gln Leu
                    765                 770                 775 cct tca gtt cag cag cca gct cag gcc cag ctg ggc cag cca cca cag   2764
Pro Ser Val Gln Gln Pro Ala Gln Ala Gln Leu Gly Gln Pro Pro Gln
                780                 785                 790 cag ttc tta cag aca tct agg ttg ctc cac ggg aat cct tcg aca cag   2812
Gln Phe Leu Gln Thr Ser Arg Leu Leu His Gly Asn Pro Ser Thr Gln
            795                 800                 805 ctc atc ctc tct gct gcc ttt cca cta caa cag agc act ttc cct cct   2860
Leu Ile Leu Ser Ala Ala Phe Pro Leu Gln Gln Ser Thr Phe Pro Pro
        810                 815                 820 tcg cac cac cag caa cac cag cct cag cag caa cag cag ctt cct cgg   2908
Ser His His Gln Gln His Gln Pro Gln Gln Gln Gln Gln Leu Pro Arg
825                 830                 835                 840 cac agg act gac agc ctg act gac cct tcc aag gtc cag cca cag       2953
His Arg Thr Asp Ser Leu Thr Asp Pro Ser Lys Val Gln Pro Gln
                845                 850                 855 tagcacacac acttcctctc tgacatgcga aggaaggggg atggccagaa agaatcgctc   3013
agttggcatg cggtcagaag ttgaacagtt tcacgagggt ggtcttgagt gttcagtccc   3073
ttgatgagac ggtagggaag tgctgcccag tgcttcagat gtccattaaa taccagccag   3133
tgggaaatgg tcatagggac acagccaatt ctgacagttt cttttgccag gtattttttg   3193
atagaaagag tatattgcca atgctaaca agctcagcta tcaaccagat ctttactgaa     3253
tccgaagagc actaacagtg ttggtagctt tagtgggtct gtgcctgcat caaatattac   3313
agagggcaca ccactgccag gggtttgctt agaatgccat gaagatagtc cagtagttaa   3373
tagtccccac cccaaactcc tctccctgtt cagacaatga tggaaccgtg atgactttga   3433
gaatgttgtg caggtttgaa ttcactgtgt acagatgctg tagtgtctct gtgtctggat   3493
ggaggagaga aagccacttt gatacagaaa gcattatctg tccctcacag gtatgagtgc   3553
atttcattag gtttgacacc atgtacaaac tgataacaac ctctctttt tcattttgtt   3613 tacaacacag tagtgttctc gttacttttc cagggcacaa gtcttttttgt ccgtgctttg   3673 gctgtgatgt cacagtttgt tcagtgaggt aacaatgtgc tgctgggaat ggatttttt    3733 aaggttaaat tattgctaca tttccactta ctcagaaata tcccttattt cattattttt   3793
caattatgtt tgagagaatt gcactgcttt attattttag atggttggtt gagagtttaa   3853
tcacatattt tgatatattt catagttgga atatttatgt aaatggtttt caacaagcct   3913
gaaagtaatt tcaagaatgt ttcagttgta agagtaaagt ttgcacacaa acatttttag   3973 gcacttttttt aacattctca gaggtgggaa ttttaacttt taggatttgt tggaatcttt   4033
ttattatctt taaaaatttc aatgcttctt ttagtcagaa atgattcagg gttatttgag   4093
gggaaaaaac ccatagtgcc ttgattttaa ttcaggtgat aactcaccat cttgaattca   4153
ttgtctggtt tcagtagcag ttttgaaacc ttagtacatt tttagcagca gtgtcattct   4213
caagtcccca tgaggactgc tgcgtctctt gggctgcctg acagcgtcac agctgggaat   4273
gggatcccaa aatcgtttcc tgtttgcatc ttcctctaaa gctaagtaac tcttttagga   4333
attaccagta aatacttgct cagagacaag ggacaagttg tctttaattt tcattgcagc   4393
```

-continued

```
actagaataa tgtaactcac atgcttttta aacattaaga tttcatttgg caatatcatt    4453
ctctacaggt aataaactcc aacaaagcta catacatttt aaaaggcatt tttttagatt    4513
ttatggtact aataatgagt ttttcaatta aagaacaaaa gatcagtagg atatagaata    4573
tcaagtatta ctgagaaaag ggaggataag tgtggcacat tagaattgac cttaaaagga    4633
aagtatgtga tggtgaggtg ctaaactggt ttcagcagtg cagataacct aaggcagagt    4693
tgctagatca gggcttgggg aactcggagt cagctatctg tctctagctt tgctctcatc    4753
atcagtaagt gtgtctttgt tttcctgttt acctgactgc aattaagtta gcaagttagt    4813
gataaaaaga aaacaaccaa agaaaattgg tacctactct tctgcgtaag aagtgtgtct    4873
agataccagt cagtaactca catatcacag aagttcttct agctgacatt catacgaata    4933
ccagaaatag ttgtgagaat acacatttat gcaagtttgt gcacacgtga cgaaatcaat    4993
gtaagtcgag cacccacatt gcttttctcc cttccacatt gccttcttct ctttggccat    5053
tccatgtcct cggagtcgga gctgtgcctc gtttatcttt ttgcatcaca tagcgataag    5113
aatttagcta caggagatac aacatgctag ttatgtaatg cctgctgttc ttcacagttc    5173
atctccctgc ttaaaagtag cagttgataa gaaactctag ctgctaaggc tgctgtccac    5233
acggagatgc atgctgggca acagttgtca gcactagctg cctcttagct ccttaattct    5293
tggttccttt ggatggcaaa ctgtctttgt ctgctcccca cacgactcca gtattctgaa    5353
gaaagttcat cttttgcctg ttcatttctg tagccaaagc tgactgaaac cccaaatcta    5413
aatcatgaaa agataccaaa aagaaacact tctcagcttc ttagaaacct taacttctct    5473
tgctgtattt catggatttg attttctttg aaattttttga ttctgggcag cgccttttaa    5533
ttaagaaatt gttaggatga aggtcaaaca ggttctcatt gccctgcagg taccttgctc    5593
tggactgctt ctgtatgggg tgacttgggg ttgctgaaca cacaggatta gaacagtaaa    5653
cacaaagctg cccttgaggc tggcgttaaa ccagagcctc aatattgaaa atatcaagtc    5713
ctctttcctt ccttagagac gagactgtga gaggaaagca actgtggtag gtgggcttgc    5773
ttgcacatga gcaccaagac cattcccaa gctctatcct cagggtagca tttagagtgc    5833
tgtgttctgc tgtcacatag acatggctta gggatgtagc actaataaaa gaatgcccgt    5893
gcttttgaat agttgtgata gcaaactcta ggctaactag caagtgtttg aattctgtgt    5953
gctgtatagt agttggtcat tgccttaaag cagtctcttg gaagttggga gcactgaagc    6013
agtccaacca tatatgggca tcacgttgag ggagatgagc cttgttcaag ccttagaaag    6073 gaccctagt ctacacaggt agattctttt cacttggata ttactgtgtt taaaatgttt    6133
ccactatgtt gaggcagttt tttaaagtgg aacacagata ggatttttag tatttctttt    6193
tttgtttctt tggtgattaa aggtttgttg gtagacattt gtgtaaagt tgttcaagcc    6253 tatcatcttt ccagtacttg tggtcctgtt cttagtacca gagtccacaa tggaaagtgt    6313
aaacactgga tattaatatt gctgagggtg catagccagg tgtgagctga ctggaacttc    6373
tcagtggtga agaaacagca caacggcact tgccattttc atagtgattg cataaagaga    6433
ccttctaagt ttgtctggat tgagtgaaca ctcttctaag aggagcttct caagtaaatg    6493
caaaggaaaa gagttgacta ttttatagc atatttaata tatttgtata taactatgag    6553
tgtagtagga accctccaca tgcctcccac ttttctaatt ccctcccctt ctgccgtagc    6613
cctagtccag cctcatccgc atgggtaatg tgcctactgt cagcctacct accaaaagat    6673
agtgctgctg ctttctgaga caggtgagat cagactctca tgcctgggga tccttatggg    6733
aggaatagca cacacttaga acaacatacc acagtttaag agcatcattt tgaaaggtaa    6793
```

-continued

```
taagcacttt attgcaatta ttcatttaga taaagtttgt atcttaggca ttaaccgttt       6853
ttaaaggatc cctaatcatc acttaggtga aatgataaac gacacatttc tgagaaatgt       6913
tcaggtccag tgaaccgtag caggtttatg ggaatgattt caaggtagcc aaataaactc       6973
tgacttttgt tttgaatgtg gtggagtcag gagattgtag atgtgtagtt tgatttaaac       7033
actattgtaa acctatcttg cctattgtgt ggacaccaaa agagaccaat gagcctgttt       7093
attttcagag gtctaggaat atgcatctgt ctgagtagat atacagaact aatctataaa       7153
cggttggtag taatatttta ggatacagta acttaaagaa ttattgagtg ttttaaatgt       7213
gccctgaaat gttggcatgt catttcagcg ttcccatttg agttgctctt gtaatatttt       7273
tgcacaaaaa ggactgagaa aagactgctt tggttgaaga aaactataat ttggtcttat       7333
tttaatgtct cctgtggaaa cactggaggt aaatttgttg gcatagttac taattcagga       7393
tatttaaaac agtgttgaac agctcatcag aaattaagca aacttatata tttaaaaatt       7453
aaaaatcttt ttttccatgt gactg                                             7478
```

<210> SEQ ID NO 11
<211> LENGTH: 855
<212> TYPE: PRT
<213> ORGANISM: Mus musculus

<400> SEQUENCE: 11

```
Met Val Phe Thr Val Ser Cys Ser Lys Met Ser Ser Ile Val Asp Arg
 1               5                  10                  15

Asp Asp Ser Ser Ile Phe Asp Gly Leu Val Glu Glu Asp Asp Lys Asp
                20                  25                  30

Lys Ala Lys Arg Val Ser Arg Asn Lys Ser Glu Lys Lys Arg Arg Asp
            35                  40                  45

Gln Phe Asn Val Leu Ile Lys Glu Leu Gly Ser Met Leu Pro Gly Asn
        50                  55                  60

Ala Arg Lys Met Asp Lys Ser Thr Val Leu Gln Lys Ser Ile Asp Phe
65                  70                  75                  80

Leu Arg Lys His Lys Glu Thr Thr Ala Gln Ser Asp Ala Ser Glu Ile
                85                  90                  95

Arg Gln Asp Trp Lys Pro Thr Phe Leu Ser Asn Glu Glu Phe Thr Gln
            100                 105                 110

Leu Met Leu Glu Ala Leu Asp Gly Phe Phe Leu Ala Ile Met Thr Asp
        115                 120                 125

Gly Ser Ile Ile Tyr Val Ser Glu Ser Val Thr Ser Leu Leu Glu His
    130                 135                 140

Leu Pro Ser Asp Leu Val Asp Gln Ser Ile Phe Asn Phe Ile Pro Glu
145                 150                 155                 160

Gly Glu His Ser Glu Val Tyr Lys Ile Leu Ser Thr His Leu Leu Glu
                165                 170                 175

Ser Asp Ser Leu Thr Pro Glu Tyr Leu Lys Ser Lys Asn Gln Leu Glu
            180                 185                 190

Phe Cys Cys His Met Leu Arg Gly Thr Ile Asp Pro Lys Glu Pro Ser
        195                 200                 205

Thr Tyr Glu Tyr Val Arg Phe Ile Gly Asn Phe Lys Ser Leu Thr Ser
    210                 215                 220

Val Ser Thr Ser Thr His Asn Gly Phe Glu Gly Thr Ile Gln Arg Thr
225                 230                 235                 240

His Arg Pro Ser Tyr Glu Asp Arg Val Cys Phe Val Ala Thr Val Arg
```

```
                    245                 250                 255
Leu Ala Thr Pro Gln Phe Ile Lys Glu Met Cys Thr Val Glu Pro
                260                 265                 270

Asn Glu Glu Phe Thr Ser Arg His Ser Leu Glu Trp Lys Phe Leu Phe
            275                 280                 285

Leu Asp His Arg Ala Pro Pro Ile Ile Gly Tyr Leu Pro Phe Glu Val
        290                 295                 300

Leu Gly Thr Ser Gly Tyr Asp Tyr Tyr His Val Asp Asp Leu Glu Asn
305                 310                 315                 320

Leu Ala Lys Cys His Glu His Leu Met Gln Tyr Gly Lys Gly Lys Ser
                325                 330                 335

Cys Tyr Tyr Arg Phe Leu Thr Lys Gly Gln Gln Trp Ile Trp Leu Gln
                340                 345                 350

Thr His Tyr Tyr Ile Thr Tyr His Gln Trp Asn Ser Arg Pro Glu Phe
                355                 360                 365

Ile Val Cys Thr His Thr Val Val Ser Tyr Ala Glu Val Arg Ala Glu
            370                 375                 380

Arg Arg Arg Glu Leu Gly Ile Glu Glu Ser Leu Pro Glu Thr Ala Ala
385                 390                 395                 400

Asp Lys Ser Gln Asp Ser Gly Ser Asp Asn Arg Ile Asn Thr Val Ser
                405                 410                 415

Leu Lys Glu Ala Leu Glu Arg Phe Asp His Ser Pro Thr Pro Ser Ala
                420                 425                 430

Ser Ser Arg Ser Ser Arg Lys Ser Ser His Thr Ala Val Ser Asp Pro
            435                 440                 445

Ser Ser Thr Pro Thr Lys Ile Pro Thr Asp Thr Ser Thr Pro Pro Arg
        450                 455                 460

Gln His Leu Pro Ala His Glu Lys Met Thr Gln Arg Arg Ser Ser Phe
465                 470                 475                 480

Ser Ser Gln Ser Ile Asn Ser Gln Ser Val Gly Pro Ser Leu Thr Gln
                485                 490                 495

Pro Ala Met Ser Gln Ala Ala Asn Leu Pro Ile Pro Gln Gly Met Ser
                500                 505                 510

Gln Phe Gln Phe Ser Ala Gln Leu Gly Ala Met Gln His Leu Lys Asp
            515                 520                 525

Gln Leu Glu Gln Arg Thr Arg Met Ile Glu Ala Asn Ile His Arg Gln
        530                 535                 540

Gln Glu Glu Leu Arg Lys Ile Gln Glu Gln Leu Gln Met Val His Gly
545                 550                 555                 560

Gln Gly Leu Gln Met Phe Leu Gln Gln Ser Asn Pro Gly Leu Asn Phe
                565                 570                 575

Gly Ser Val Gln Leu Ser Ser Gly Asn Ser Asn Ile Gln Gln Leu Thr
            580                 585                 590

Pro Val Asn Met Gln Gly Gln Val Val Pro Ala Asn Gln Val Gln Ser
        595                 600                 605

Gly His Ile Ser Thr Gly His Met Ile Gln Gln Thr Leu Gln
        610                 615                 620

Ser Thr Ser Thr Gln Gln Ser Gln Gln Ser Val Met Ser Gly His Ser
625                 630                 635                 640

Gln Gln Thr Ser Leu Pro Ser Gln Thr Pro Ser Thr Leu Thr Ala Pro
                645                 650                 655

Leu Tyr Asn Thr Met Val Ile Ser Gln Pro Ala Ala Gly Ser Met Val
                660                 665                 670
```

-continued

```
Gln Ile Pro Ser Ser Met Pro Gln Asn Ser Thr Gln Ser Ala Thr Val
            675                 680                 685

Thr Thr Phe Thr Gln Asp Arg Gln Ile Arg Phe Ser Gln Gly Gln Gln
        690                 695                 700

Leu Val Thr Lys Leu Val Thr Ala Pro Val Ala Cys Gly Ala Val Met
705                 710                 715                 720

Val Pro Ser Thr Met Leu Met Gly Gln Val Val Thr Ala Tyr Pro Thr
                725                 730                 735

Phe Ala Thr Gln Gln Gln Gln Ala Gln Thr Leu Ser Val Thr Gln Gln
            740                 745                 750

Gln Gln Gln Gln Gln Gln Pro Pro Gln Gln Gln Gln Gln Gln
        755                 760                 765

Gln Ser Ser Gln Glu Gln Gln Leu Pro Ser Val Gln Gln Pro Ala Gln
770                 775                 780

Ala Gln Leu Gly Gln Pro Gln Gln Phe Leu Gln Thr Ser Arg Leu
785                 790                 795                 800

Leu His Gly Asn Pro Ser Thr Gln Leu Ile Leu Ser Ala Ala Phe Pro
            805                 810                 815

Leu Gln Gln Ser Thr Phe Pro Pro Ser His His Gln His Gln Pro
            820                 825                 830

Gln Gln Gln Gln Gln Leu Pro Arg His Arg Thr Asp Ser Leu Thr Asp
            835                 840                 845

Pro Ser Lys Val Gln Pro Gln
            850                 855
```

<210> SEQ ID NO 12  
<211> LENGTH: 2065  
<212> TYPE: DNA  
<213> ORGANISM: Mus musculus  
<220> FEATURE:  
<221> NAME/KEY: CDS  
<222> LOCATION: (1)...(1875)

<400> SEQUENCE: 12

```
atg gcg gac cag aga atg gac att tcc tca acc atc agc gac ttc atg      48
Met Ala Asp Gln Arg Met Asp Ile Ser Ser Thr Ile Ser Asp Phe Met
 1               5                  10                  15 tct ccg ggc ccc acc gac cta ctc tcc ggt tcc ctg ggc acc agt ggt      96
Ser Pro Gly Pro Thr Asp Leu Leu Ser Gly Ser Leu Gly Thr Ser Gly
            20                  25                  30 gtg gac tgc aat cgc aag agg aaa ggc agt gcc act gac tac caa gaa     144
Val Asp Cys Asn Arg Lys Arg Lys Gly Ser Ala Thr Asp Tyr Gln Glu
        35                  40                  45 agt atg gac aca gac aaa gat gac cct cat gga agg tta gaa tat gca     192
Ser Met Asp Thr Asp Lys Asp Asp Pro His Gly Arg Leu Glu Tyr Ala
    50                  55                  60 gaa cac caa gga agg atc aag aat gca agg gag gcc cac agt cag att     240
Glu His Gln Gly Arg Ile Lys Asn Ala Arg Glu Ala His Ser Gln Ile
65                  70                  75                  80 gaa aag agg cgt cgg gac aaa atg aac agt ttc att gat gaa ttg gct     288
Glu Lys Arg Arg Arg Asp Lys Met Asn Ser Phe Ile Asp Glu Leu Ala
                85                  90                  95 tct ttg gta cca aca tgc aat gca atg tcc agg aag tta gat aaa ctc     336
Ser Leu Val Pro Thr Cys Asn Ala Met Ser Arg Lys Leu Asp Lys Leu
            100                 105                 110 acc gtg cta agg atg gct gtt cag cac atg aaa act ttg aga ggt gcc     384
Thr Val Leu Arg Met Ala Val Gln His Met Lys Thr Leu Arg Gly Ala
        115                 120                 125
```

```
acc aac cca tac aca gaa gca aac tac aag cca aca ttt cta tca gat      432
Thr Asn Pro Tyr Thr Glu Ala Asn Tyr Lys Pro Thr Phe Leu Ser Asp
    130                 135                 140 gac gaa ctg aaa cac cta att ctc agg gca gca gat gga ttt ttg ttt      480
Asp Glu Leu Lys His Leu Ile Leu Arg Ala Ala Asp Gly Phe Leu Phe
145                 150                 155                 160 gtc gta gga tgt gac cga ggg aag atc ctc ttt gtc tcc gag tct gtc      528
Val Val Gly Cys Asp Arg Gly Lys Ile Leu Phe Val Ser Glu Ser Val
                165                 170                 175 ttc aag atc ctc aat tat agc cag aat gac ctt att ggc cag agc ttg      576
Phe Lys Ile Leu Asn Tyr Ser Gln Asn Asp Leu Ile Gly Gln Ser Leu
            180                 185                 190 ttt gac tac ctg cat cca aaa gat att gcc aaa gtt aag gaa cag cta      624
Phe Asp Tyr Leu His Pro Lys Asp Ile Ala Lys Val Lys Glu Gln Leu
        195                 200                 205 tct tcc tcg gac act gcg ccc cgg gag cga ctc att gat gcc aag act      672
Ser Ser Ser Asp Thr Ala Pro Arg Glu Arg Leu Ile Asp Ala Lys Thr
    210                 215                 220 gga ctt ccg gtt aaa acg gat ata acc cct ggg ccc tcc cgg cta tgc      720
Gly Leu Pro Val Lys Thr Asp Ile Thr Pro Gly Pro Ser Arg Leu Cys
225                 230                 235                 240 tct gga gcc cgc cgc tct ctg ttc tgt aga atg aag tgc aac agg cct      768
Ser Gly Ala Arg Arg Ser Leu Phe Cys Arg Met Lys Cys Asn Arg Pro
                245                 250                 255 tca gta aag gtg gaa gat aag gac ttc gcc tct acc tgt tca aag aaa      816
Ser Val Lys Val Glu Asp Lys Asp Phe Ala Ser Thr Cys Ser Lys Lys
            260                 265                 270 aaa gat cga aaa agc ttc tgc aca atc cac agc aca ggc tat ttg aaa      864
Lys Asp Arg Lys Ser Phe Cys Thr Ile His Ser Thr Gly Tyr Leu Lys
        275                 280                 285 agc tgg cca ccc acg aag atg ggg ctg gac gaa gac aat gag cca gac      912
Ser Trp Pro Pro Thr Lys Met Gly Leu Asp Glu Asp Asn Glu Pro Asp
    290                 295                 300 aac gag ggc tgc aac ctc agc tgc ctc gtt gca atc ggg cgc ctg cac      960
Asn Glu Gly Cys Asn Leu Ser Cys Leu Val Ala Ile Gly Arg Leu His
305                 310                 315                 320 tcg cac atg gtt cca caa cca gcg aac ggg gaa ata cgg gtg aaa tct     1008
Ser His Met Val Pro Gln Pro Ala Asn Gly Glu Ile Arg Val Lys Ser
                325                 330                 335 atg gag tac gtt tct cga cac gca ata gat ggg aaa ttt gtt ttt gta     1056
Met Glu Tyr Val Ser Arg His Ala Ile Asp Gly Lys Phe Val Phe Val
            340                 345                 350 gat cag agg gcg aca gct att ttg gcg tat cta cca cag gaa ctt cta     1104
Asp Gln Arg Ala Thr Ala Ile Leu Ala Tyr Leu Pro Gln Glu Leu Leu
        355                 360                 365 ggt aca tca tgt tat gag tat ttt cat caa gac gac ata gga cac ctc     1152
Gly Thr Ser Cys Tyr Glu Tyr Phe His Gln Asp Asp Ile Gly His Leu
    370                 375                 380 gca gaa tgt cac agg caa gtt tta cag aca aga gaa aag atc aca act     1200
Ala Glu Cys His Arg Gln Val Leu Gln Thr Arg Glu Lys Ile Thr Thr
385                 390                 395                 400 aat tgc tat aag ttt aag atc aaa gat ggt tct ttt atc acg cta cga     1248
Asn Cys Tyr Lys Phe Lys Ile Lys Asp Gly Ser Phe Ile Thr Leu Arg
                405                 410                 415 agt cga tgg ttc agt ttc atg aac ccg tgg acc aag gaa gtt gaa tac     1296
Ser Arg Trp Phe Ser Phe Met Asn Pro Trp Thr Lys Glu Val Glu Tyr
            420                 425                 430 att gtc tca acc aac act gtt gtt tta gcc aat gtc ctg gaa ggc ggg     1344
Ile Val Ser Thr Asn Thr Val Val Leu Ala Asn Val Leu Glu Gly Gly
```

```
                435                 440                 445
gac cca acc ttc ccg cag cta aca gca ccc ccc cac agc atg gac agc     1392
Asp Pro Thr Phe Pro Gln Leu Thr Ala Pro Pro His Ser Met Asp Ser
    450                 455                 460 atg ctg ccc tct gga gaa ggt ggc cca aag agg act cat ccc act gtt     1440
Met Leu Pro Ser Gly Glu Gly Gly Pro Lys Arg Thr His Pro Thr Val
465                 470                 475                 480 cca ggc att cca ggg gga acc aga gcc gga gca gga aaa ata ggt cga     1488
Pro Gly Ile Pro Gly Gly Thr Arg Ala Gly Ala Gly Lys Ile Gly Arg
                485                 490                 495 atg att gcc gag gaa atc atg gaa atc cac agg ata aga ggg tca tcg     1536
Met Ile Ala Glu Glu Ile Met Glu Ile His Arg Ile Arg Gly Ser Ser
            500                 505                 510 cct tcc agc tgt ggc tcc agc ccg ctg aac atc aca agt acg cct ccc     1584
Pro Ser Ser Cys Gly Ser Ser Pro Leu Asn Ile Thr Ser Thr Pro Pro
        515                 520                 525 cct gat gcc tct tct cca gga ggc aag aag att cta aat gga ggg act     1632
Pro Asp Ala Ser Ser Pro Gly Gly Lys Lys Ile Leu Asn Gly Gly Thr
    530                 535                 540 cca gac att cct tcc act gga cta tta cca ggg cag gct cag gag acc     1680
Pro Asp Ile Pro Ser Thr Gly Leu Leu Pro Gly Gln Ala Gln Glu Thr
545                 550                 555                 560 cca ggg tat ccc tat tct gat agt tct tct att ctt ggt gag aac ccc     1728
Pro Gly Tyr Pro Tyr Ser Asp Ser Ser Ser Ile Leu Gly Glu Asn Pro
                565                 570                 575 cac ata ggc atc gat atg ata gat aac gac caa gga tca agt agt ccc     1776
His Ile Gly Ile Asp Met Ile Asp Asn Asp Gln Gly Ser Ser Ser Pro
            580                 585                 590 agt aac gat gag gca gca atg gct gtc atc atg agc ctc ttg gaa gca     1824
Ser Asn Asp Glu Ala Ala Met Ala Val Ile Met Ser Leu Leu Glu Ala
        595                 600                 605 gat gcg ggg ctg ggt ggc ccc gtt gac ttt agt gac ttg cca tgg ccg     1872
Asp Ala Gly Leu Gly Gly Pro Val Asp Phe Ser Asp Leu Pro Trp Pro
    610                 615                 620 ctg tagacactac atttgctttg gcaacagctg cagtatcaaa gtgcattaat          1925
Leu
625 ggtgaagttt tacagtctgt gaagcttact ggatagagag agaacagctt ttatgtactg   1985 actccataaa agccacctca gagccattga tacaagtcaa tctaccatgt gtaacttcag   2045 acaaagtgga actaaacctg                                               2065

<210> SEQ ID NO 13
<211> LENGTH: 625
<212> TYPE: PRT
<213> ORGANISM: Mus musculus

<400> SEQUENCE: 13

Met Ala Asp Gln Arg Met Asp Ile Ser Ser Thr Ile Ser Asp Phe Met
1               5                   10                  15

Ser Pro Gly Pro Thr Asp Leu Leu Ser Gly Ser Leu Gly Thr Ser Gly
            20                  25                  30

Val Asp Cys Asn Arg Lys Arg Lys Gly Ser Ala Thr Asp Tyr Gln Glu
        35                  40                  45

Ser Met Asp Thr Asp Lys Asp Asp Pro His Gly Arg Leu Glu Tyr Ala
    50                  55                  60

Glu His Gln Gly Arg Ile Lys Asn Ala Arg Glu Ala His Ser Gln Ile
65                  70                  75                  80
```

-continued

```
Glu Lys Arg Arg Arg Asp Lys Met Asn Ser Phe Ile Asp Glu Leu Ala
             85                  90                  95
Ser Leu Val Pro Thr Cys Asn Ala Met Ser Arg Lys Leu Asp Lys Leu
            100                 105                 110
Thr Val Leu Arg Met Ala Val Gln His Met Lys Thr Leu Arg Gly Ala
        115                 120                 125
Thr Asn Pro Tyr Thr Glu Ala Asn Tyr Lys Pro Thr Phe Leu Ser Asp
    130                 135                 140
Asp Glu Leu Lys His Leu Ile Leu Arg Ala Ala Asp Gly Phe Leu Phe
145                 150                 155                 160
Val Val Gly Cys Asp Arg Gly Lys Ile Leu Phe Val Ser Glu Ser Val
                165                 170                 175
Phe Lys Ile Leu Asn Tyr Ser Gln Asn Asp Leu Ile Gly Gln Ser Leu
            180                 185                 190
Phe Asp Tyr Leu His Pro Lys Asp Ile Ala Lys Val Lys Glu Gln Leu
        195                 200                 205
Ser Ser Ser Asp Thr Ala Pro Arg Glu Arg Leu Ile Asp Ala Lys Thr
    210                 215                 220
Gly Leu Pro Val Lys Thr Asp Ile Thr Pro Gly Pro Ser Arg Leu Cys
225                 230                 235                 240
Ser Gly Ala Arg Arg Ser Leu Phe Cys Arg Met Lys Cys Asn Arg Pro
                245                 250                 255
Ser Val Lys Val Glu Asp Lys Asp Phe Ala Ser Thr Cys Ser Lys Lys
            260                 265                 270
Lys Asp Arg Lys Ser Phe Cys Thr Ile His Ser Thr Gly Tyr Leu Lys
        275                 280                 285
Ser Trp Pro Pro Thr Lys Met Gly Leu Asp Glu Asp Asn Glu Pro Asp
    290                 295                 300
Asn Glu Gly Cys Asn Leu Ser Cys Leu Val Ala Ile Gly Arg Leu His
305                 310                 315                 320
Ser His Met Val Pro Gln Pro Ala Asn Gly Glu Ile Arg Val Lys Ser
                325                 330                 335
Met Glu Tyr Val Ser Arg His Ala Ile Asp Gly Lys Phe Val Phe Val
            340                 345                 350
Asp Gln Arg Ala Thr Ala Ile Leu Ala Tyr Leu Pro Gln Glu Leu Leu
        355                 360                 365
Gly Thr Ser Cys Tyr Glu Tyr Phe His Gln Asp Asp Ile Gly His Leu
    370                 375                 380
Ala Glu Cys His Arg Gln Val Leu Gln Thr Arg Glu Lys Ile Thr Thr
385                 390                 395                 400
Asn Cys Tyr Lys Phe Lys Ile Lys Asp Gly Ser Phe Ile Thr Leu Arg
                405                 410                 415
Ser Arg Trp Phe Ser Phe Met Asn Pro Trp Thr Lys Glu Val Glu Tyr
            420                 425                 430
Ile Val Ser Thr Asn Thr Val Leu Ala Asn Val Leu Glu Gly Gly
        435                 440                 445
Asp Pro Thr Phe Pro Gln Leu Thr Ala Pro His Ser Met Asp Ser
    450                 455                 460
Met Leu Pro Ser Gly Glu Gly Gly Pro Lys Arg Thr His Pro Thr Val
465                 470                 475                 480
Pro Gly Ile Pro Gly Gly Thr Arg Ala Gly Ala Gly Lys Ile Gly Arg
                485                 490                 495
Met Ile Ala Glu Glu Ile Met Glu Ile His Arg Ile Arg Gly Ser Ser
```

-continued

```
                    500                     505                     510
Pro Ser Ser Cys Gly Ser Ser Pro Leu Asn Ile Thr Ser Thr Pro Pro
        515                     520                     525

Pro Asp Ala Ser Ser Pro Gly Gly Lys Lys Ile Leu Asn Gly Gly Thr
    530                     535                     540

Pro Asp Ile Pro Ser Thr Gly Leu Leu Pro Gly Gln Ala Gln Glu Thr
545                     550                     555                     560

Pro Gly Tyr Pro Tyr Ser Asp Ser Ser Ser Ile Leu Gly Glu Asn Pro
                565                     570                     575

His Ile Gly Ile Asp Met Ile Asp Asn Asp Gln Gly Ser Ser Ser Pro
                580                     585                     590

Ser Asn Asp Glu Ala Ala Met Ala Val Ile Met Ser Leu Leu Glu Ala
        595                     600                     605

Asp Ala Gly Leu Gly Gly Pro Val Asp Phe Ser Asp Leu Pro Trp Pro
    610                     615                     620

Leu
625
```